United States Patent [19]

Holzrichter

[11] Patent Number: 6,006,175
[45] Date of Patent: Dec. 21, 1999

[54] METHODS AND APPARATUS FOR NON-ACOUSTIC SPEECH CHARACTERIZATION AND RECOGNITION

[75] Inventor: John F. Holzrichter, Berkeley, Calif.

[73] Assignee: The Regents of the University of California, Oakland, Calif.

[21] Appl. No.: 08/597,596

[22] Filed: Feb. 6, 1996

[51] Int. Cl.$^6$ ..................................................... G10L 3/02
[52] U.S. Cl. ........................ 704/208; 704/205; 704/206; 704/207
[58] Field of Search .................................. 395/2.1, 2.16, 395/2.27, 2.37, 2.67, 2.17, 2.15, 2.14; 704/205–208, 201, 218, 228, 258

[56] References Cited

U.S. PATENT DOCUMENTS

| | | | |
|---|---|---|---|
| 2,193,102 | 3/1940 | Koch | 250/6 |
| 2,539,594 | 1/1951 | Rines et al. | 250/17 |
| 2,823,365 | 2/1958 | Rines | 340/6 |
| 3,555,188 | 1/1971 | Meacham | 381/115 |
| 3,699,856 | 10/1972 | Chabot et al. | 95/1.1 |
| 3,925,774 | 12/1975 | Amlung | 340/258 |
| 4,027,303 | 5/1977 | Neuwirth et al. | 340/258 |
| 4,092,493 | 5/1978 | Rabiner et al. | 179/1 |
| 4,260,229 | 4/1981 | Bloomstein | 352/50 |
| 4,461,025 | 7/1984 | Franklin | 381/56 |
| 4,621,348 | 11/1986 | Tender | 367/116 |
| 4,769,845 | 9/1988 | Nakamura | 381/43 |
| 4,783,803 | 11/1988 | Baker et al. | 381/42 |
| 4,803,729 | 2/1989 | Baker | 381/43 |
| 4,882,746 | 11/1989 | Shimada | 455/462 |
| 4,903,305 | 2/1990 | Gillick et al. | 381/41 |
| 4,914,703 | 4/1990 | Gillick | 381/43 |
| 5,008,941 | 4/1991 | Sejnoha | 3881/43 |
| 5,027,406 | 6/1991 | Roberts et al. | 381/43 |
| 5,030,956 | 7/1991 | Murphy | 342/22 |
| 5,127,055 | 6/1992 | Larkey | 381/43 |
| 5,202,952 | 4/1993 | Gillick et al. | 395/2 |
| 5,227,797 | 7/1993 | Murphy | 342/22 |
| 5,280,563 | 1/1994 | Ganong | 395/2 |
| 5,337,394 | 8/1994 | Sejnoha | 395/2.5 |
| 5,345,471 | 9/1994 | McEwan | 375/1 |
| 5,361,070 | 11/1994 | McEwan | 342/21 |
| 5,386,492 | 1/1995 | Wilson et al. | 395/2.61 |
| 5,388,183 | 2/1995 | Lynch | 395/2.51 |
| 5,390,278 | 2/1995 | Gupta et al. | 395/2.52 |
| 5,428,707 | 6/1995 | Gould et al. | 395/2.4 |
| 5,573,012 | 11/1996 | McEwan | 128/782 |

OTHER PUBLICATIONS

Rabiner, L. R. "Applications of Voice Processing to Telecommunications", Proc. of the IEEE, 82(2), 199–228 (Feb. 1994).

Skolnik, M.I. (ed.) "Radar Handbook 2nd ed." McGraw Hill, page v (1990).

Waynant, R. W. and Ediger, M. N. (eds.) "Electro–Optics Handbook", McGraw–Hill, p. 24.22 (1994).

Flanagan, J. L. "Speech Analysis Synthesis, and Perception", Academic Press NY, pp. 8, 16–20, 154–156 (1965).

Coker, C.H. "A Model of Articulatory Dynamics and Control", Proc. IEEE, 64(4), 452–459 (1976).

Javkin, H. et al "Multi–Parameter Speech Training System" Speech and Language Technology for Disabled Persons, Proceedings of a European Speech Communication Association (ESCA) Workshop, Stockholm, Sweden, 137–140 (May 31, 1993).

(List continued on next page.)

*Primary Examiner*—Tariq R. Hafiz
*Attorney, Agent, or Firm*—John P. Wooldridge

[57] ABSTRACT

By simultaneously recording EM wave reflections and acoustic speech information, the positions and velocities of the speech organs as speech is articulated can be defined for each acoustic speech unit. Well defined time frames and feature vectors describing the speech, to the degree required, can be formed. Such feature vectors can uniquely characterize the speech unit being articulated each time frame. The onset of speech, rejection of external noise, vocalized pitch periods, articulator conditions, accurate timing, the identification of the speaker, acoustic speech unit recognition, and organ mechanical parameters can be determined.

48 Claims, 31 Drawing Sheets

OTHER PUBLICATIONS

Papcun, G. et. al. "Inferring articulation and recognizing gestures from acoustics with a neural network trained on x–ray microbeam data", J. Acoustic Soc. Am. 92(2), 688–700 (Aug. 1992).

Olive, J.P. et al. "Acoustics of American Engliish Speech", Springer–Verlag, pp. 79–80 (1993).

Hirose, H. and Gay, T. "The Activity of the Intrinsic Laryngeal Muscles in Voicing Control", Phonetica 25, 140–164 (1972).

Tuller, B. et al. "An evaluation of an alternating magnetic field device for monitoring tongue movements", J. Acoust. Soc. Am. 88(2), 674–679 (Aug. 1990).

Gersho, A. "Advances in Speech and Audio Compression" Proceeding of IEEE 82(6), 900–918 (1994).

Schroeter, J. and Sondhi, M. M. "Techniques for Estimating Vocal–Tract Shapes from the Speech Signal", IEEE Trans. on Speech and Audio Proceeding 2(1), Part II, 133–150 (Jan. 1994).

Atal, B. S. and Hanauer, S. L. "Speech Analysis and Synthesis by Linear Prediction of the Speech Wave", J. Acoustic Soc. Am. 50(2) Part II, 637–655 (1971).

Furui, S. "Cepstral Analysis Technique for Automatic Speaker Verification", IEEE Trans. on Acoustics, Speech, and Signal Processing, ASSP 29(2), 254–272 (1981).

Rabiner, L. and Juang, B.–H. "Fundamentals of Speech Recognition", Prentice Hall, pp. 436–438, 494 (1993).

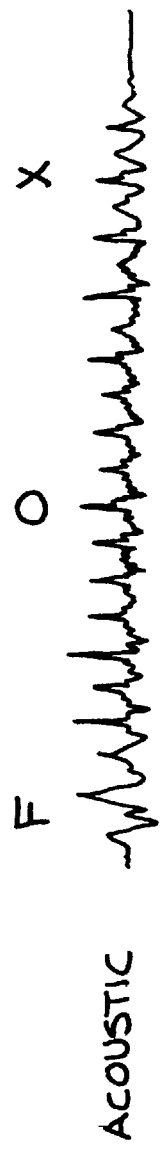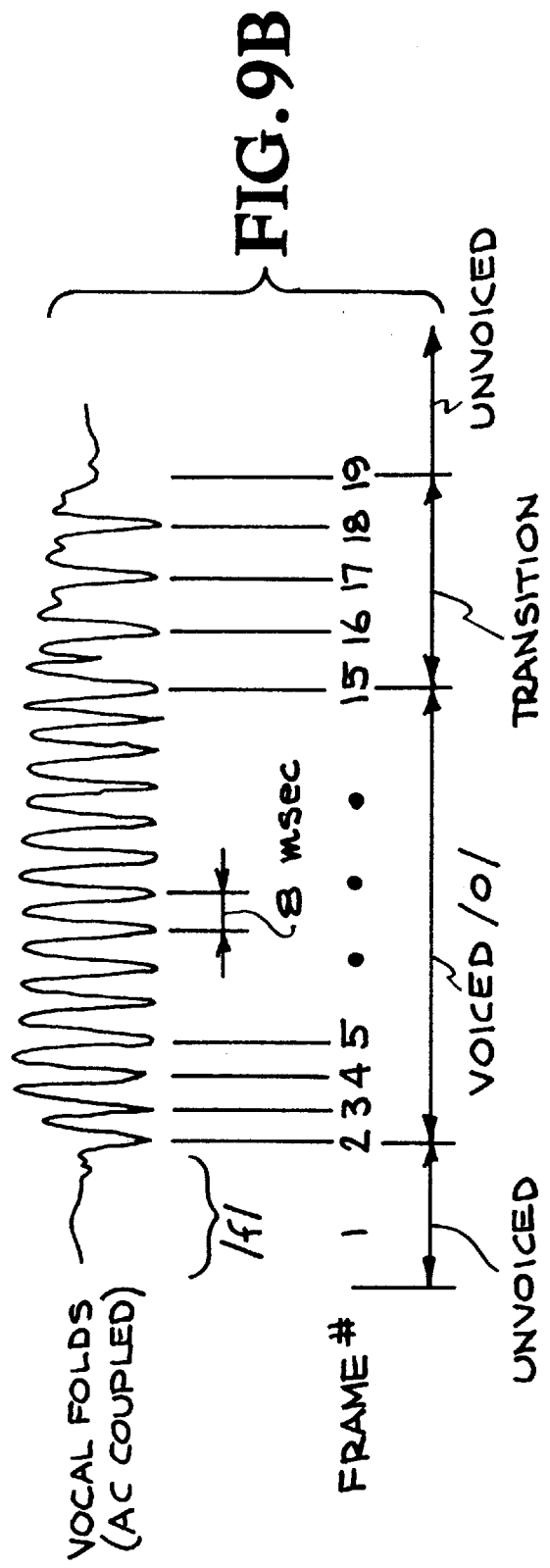
FIG. 9A
FIG. 9B

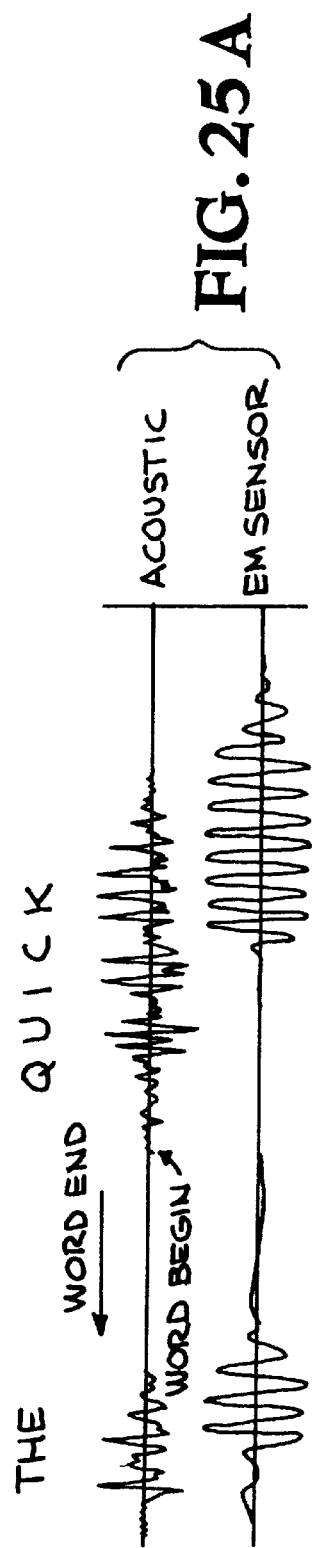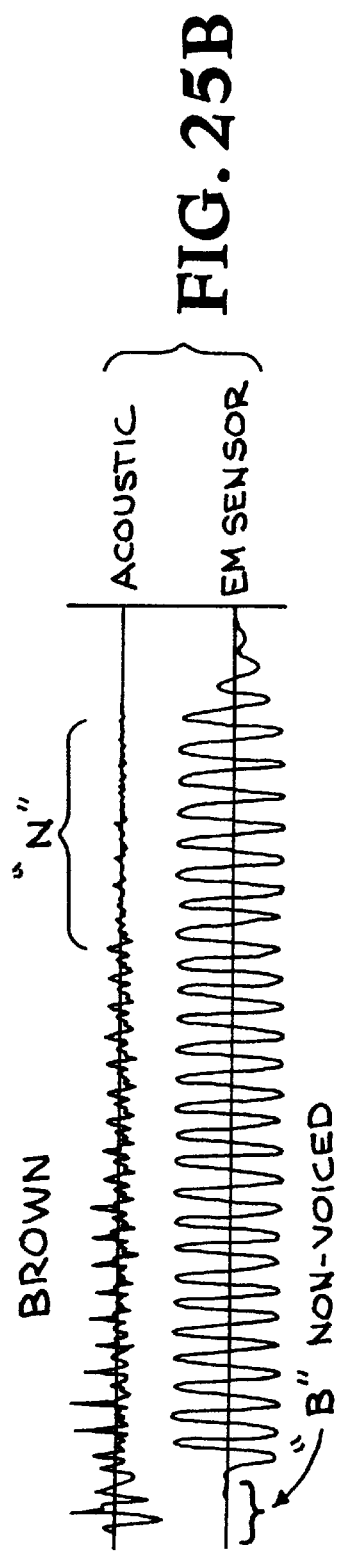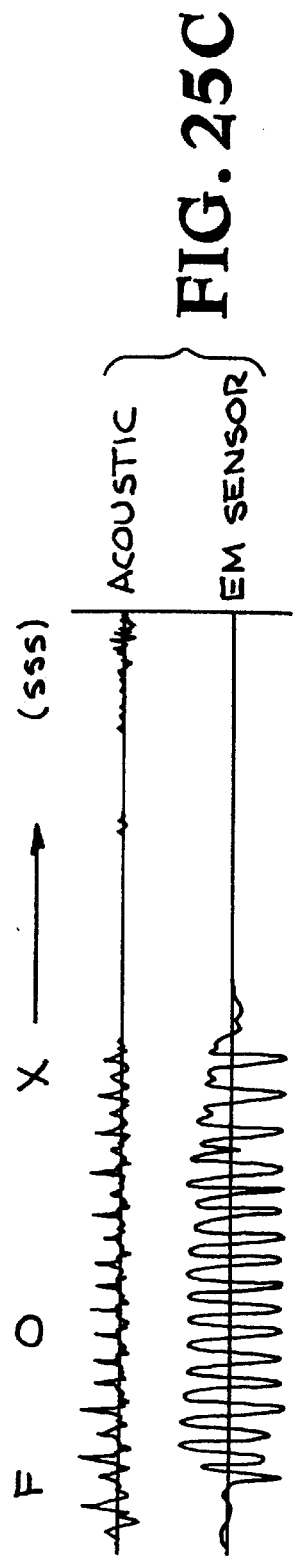

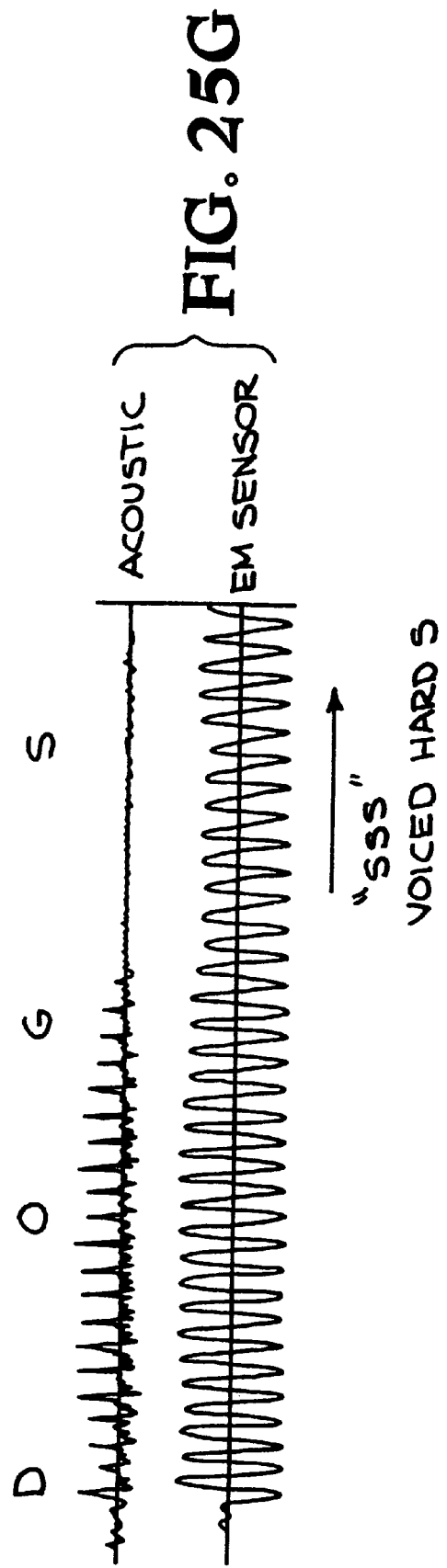
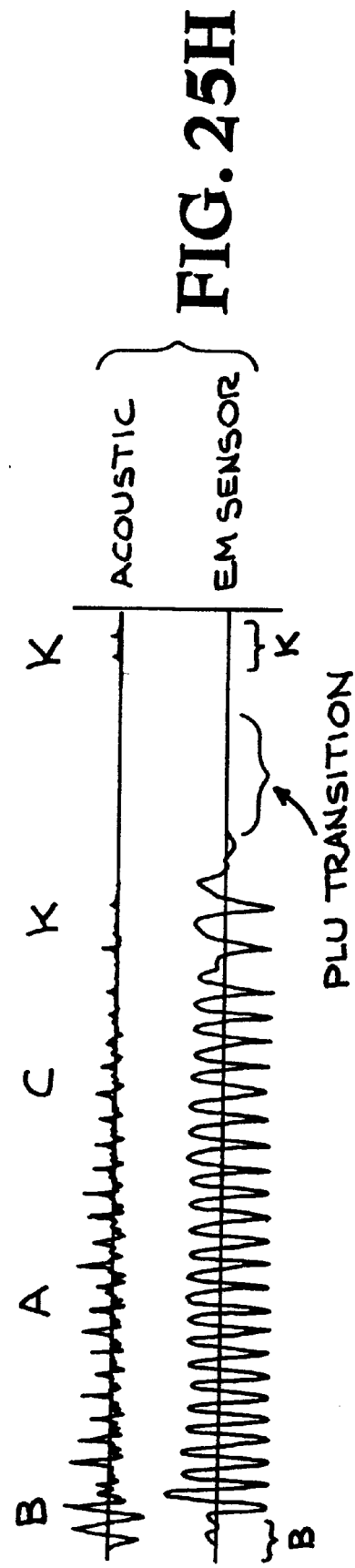

METHODS AND APPARATUS FOR NON-ACOUSTIC SPEECH CHARACTERIZATION AND RECOGNITION

The United States Government has rights in this invention pursuant to Contract No. W-7405-ENG-48 between the United States Department of Energy and the University of California for the operation of Lawrence Livermore National Laboratory.

BACKGROUND OF THE INVENTION

The invention relates generally to speech recognition and more particularly to the use of nonacoustic information in combination with acoustic information for speech recognition and related speech technologies.

Speech Recognition

The development history of speech recognition (SR) technology has spanned four decades of intensive research. In the '50s, SR research was focused on isolated digits, monosyllabic words, speaker dependence, and phonetic-based attributes. Feature descriptions included a set of attributes like formants, pitch, voiced/unvoiced, energy, nasality, and frication, associated with each distinct phoneme. The numerical attributes of a set of such phonetic descriptions is called a feature vector. In the '60s, researchers addressed the problem that time intervals spanned by units like phonemes, syllables, or words are not maintained at fixed proportions of utterance duration, from one speaker to another or from one speaking rate to another. No adequate solution was found for aligning the sounds in time in such a way that statistical analysis could be used. Variability in phonetic articulation due to changes in speaker vocal organ positioning was found to be a key problem in speech recognition. Variability was in part due to sounds running together (often causing incomplete articulation), or half-way organ positioning between two sounds (often called coarticulation). Variability due to speaker differences were also very difficult to deal with. By the early '70s, the phonetic based approach was virtually abandoned because of the limited ability to solve the above problems. A much more efficient way to extract and store acoustic feature vectors, and relate acoustic patterns to underlying phonemic units and words, was needed.

In the 1970s, workers in the field showed that short "frames" (e.g., 10 ms intervals) of the time waveform could be well approximated by an all poles (but no zeros) analytic representation, using numerical "linear predictive coding" (LPC) coefficients found by solving covariance equations. Specific procedures are described in B. S. Atal and S. L. Hanauer, "Speech analysis and synthesis by linear prediction of the speech wave," J. Acoust. Soc. Am. 50(2), 637 (1971) and L. Rabiner, U.S. Pat. No. 4,092,493. Better coefficients for achieving accurate speech recognition were shown to be the Cepstral coefficients, e.g., S. Furui, "Cepstral analysis technique for automatic speaker verification," IEEE Trans. on Acoust. Speech and Signal Processing, ASSP-29 (2), 254, (1981). They are Fourier coefficients of the expansion of the logarithm of the absolute value of the corresponding short time interval power spectrum. Cepstral coefficients effectively separate excitation effects of the vocal cords from resonant transfer functions of the vocal tract. They also capture the characteristic that human hearing responds to the logarithm of changes in the acoustic power, and not to linear changes. Cepstral coefficients are related directly to LPC coefficients. They provide a mathematically accurate method of approximation requiring only a small number of values. For example, 12 to 24 numbers are used as the component values of the feature vector for the measured speech time interval or "frame" of speech.

The extraction of acoustic feature vectors based on the LPC approach has been successful, but it has serious limitations. Its success relies on being able to simply find the best match of the unknown waveform feature vector to one stored in a library (also called a codebook) for a known sound or word. This process circumvented the need for a specific detailed description of phonetic attributes. The LPC-described waveform could represent a speech phoneme, where a phoneme is an elementary word-sound unit. There are 40 to 50 phonemes in American English, depending upon whose definition is used. However, the LPC information does not allow unambiguous determination of physiological conditions for vocal tract model constraints. For example it does not allow accurate, unambiguous vocal fold on/off period measurements or pitch. Alternatively, the LPC representation could represent longer time intervals such as the entire period over which a word was articulated. Vector "quantization" (VQ) techniques assisted in handling large variations in articulation of the same sound from a potentially large speaker population. This helped provide speaker independent recognition capability, but the speaker normalization problem was not completely solved, and remains an issue today. Automatic methods were developed to time align the same sound units when spoken at a different rate by the same or different speaker. One successful techniques was the Dynamic Time Warping algorithm which did a nonlinear time scaling of the feature coefficients. This provided a partial solution to the problem identified in the '60s as the nonuniform rate of speech.

For medium size vocabularies (e.g., about 500 words), it is acceptable to use the feature vectors for the several speech units in a single word as basic matching units. During the late 1970s, many commercial products became available on the market, permitting limited vocabulary recognition. However, word matching also required the knowledge of the beginning and the end of the word. Thus sophisticated end-point (and onset) detection algorithms were developed. In addition, purposeful insertion of pauses by the user between words simplified the problem for many applications. This approach is known as discrete speech. However, for a larger vocabulary (e.g., >1000 words), the matching library becomes large and unwieldy. In addition, discrete speech is unnatural for human communications, but continuous speech makes end-point detection difficult. Overcoming the difficulties of continuous speech with a large size vocabulary was a primary focus of speech recognition (SR) research in the '80s. To accomplish this, designers of SR systems found that the use of shorter sound units such as phonemes or PLUs (phone-like units) was preferable, because of the smaller number of units needed to describe human speech.

In the '80s, a statistical pattern matching technique known as the Hidden Markov Model (HMM) was applied successfully in solving the problems associated with continuous speech and large vocabulary size. HMMs were constructed to first recognize the 50 phonemes, and to then recognize the words and word phrases based upon the pattern of phonemes. For each phoneme, a probability model is built during a learning phase, indicating the likelihood that a particular acoustic feature vector represents each particular phoneme. The acoustic system measures the qualities of each speaker during each time frame (e.g. 10 ms), software corrects for speaker rates, and forms Cepstral coefficients. In specific systems, other values such as total acoustic energy, differential Cepstral coefficients, pitch, and zero crossings are measured and added as components with the Cepstral coefficients, to make a longer feature vector. By example, assume 10 Cepstral coefficients are extracted from a continuous speech utterance every 10 ms. Since phonemes last about 100 ms on average, the HMM phonemic model would contain 10 states (i.e., ten 10 ms segments) with 10 symbols (i.e., Cepstral values) per state. The value of each symbol changes from state to state for each phoneme because the acoustic signal in each 10 ms time frame is characterized by a different set of acoustic features captured by the Cepstral coefficients. The HMM approach is to compute the statistics of frequencies of occurrence of the symbols in one state related to those in the next state from a large training set of speakers saying the same phonemes in the same and differing word series. For example, a set of state transitional probabilities and the accompanying array of 10 symbols by 10 state array values that best describes each phoneme are obtained. To recognize an unknown phoneme, the user computes the 10 by 10 array and matches it to the precomputed probabilistic phonemic model using the maximum likelihood detection approach. The HMM statistical approach makes use of the fact that the probability of observing a given set of 10 states in a time sequence is high for only one set of phonemes.

The best laboratory performance of a highly trained, single user HMM based recognizer today is about 99% correct recognition of words. In a normal work place with ambient office noise, with average training, on large vocabulary natural speech, the accuracy drops well below 90%. For almost all applications, this is not adequate; for high value applications, a >10% error rate is intolerable. A typical error performance specification of a reliable human communication system is usually in the range from 1 error in 1000 to as low as 1 error in 10,000, depending upon how much error correction communication between speaker and listener is used or allowed.

Thus, to reach this goal, factors of 100 to 1000 improvement in speech recognition accuracy are required. HMM based recognizers, or variants thereon, have been in intense development for more than 15 years, and are unlikely to deliver such a major breakthrough in accuracy. One major reason for this is that the acoustic signal contains insufficient information to accurately represent all of the sound units used in a given human language. In particular, variability of these speech units through incomplete articulation or through coarticulation makes for great difficulty in dealing with day to day variations in a given speaker's speech. Yet, even greater problems occur with different speakers and with the inability to do complete speaker normalization, and finally with the problems of human speakers who like to use large vocabularies with rapid, run together speech. Even as computer processors and memories drop in price and size, the complexity of processing to supply all of the missing acoustic information, to correct mistakes in articulation, and to deal with noise and speaker variability will be difficult or impossible to handle. They will not be able to supply real time recognition meeting the demands of the market place for accuracy, cost, and speed.

Present Example of Speech Recognition

J. L. Flanagan, "Technologies of Multimedia Communications", Proc. of IEEE 82, 590, April 1994 on p. 592 states: "The research frontier in speech recognition is large vocabularies and language models that are more representative of natural language . . . Systems for vocabularies greater than 1000 words are being demonstrated. But word error rate is typically around 5% or more, and hence sentence error rate is substantially higher."

A current speech signal processing model with the characteristics described by Flanagan uses a microphone to detect acoustic speech information. The acoustic signals are processed by LPC algorithms to produce a feature vector which is compared to a stored feature vector library and further processed for word and sentence assembly. The details of estimating the feature vector are that it uses an open loop, 10th order, short time stationary model for the vocal tract. The excitation signal $X(t)$ is assumed to be random broadband white noise. A fast Linear Predictive Coding (LPC) algorithm is used to compute the model coefficients. A direct mapping of LPC coefficients to the Cepstral coefficients provides a robust and compact representation of the short time power spectrum which is the basis for statistical matching. FIG. 1 shows the essential processes of a modern prior art speech recognition system.

The open loop speech processing model has many drawbacks. First, the unknown excitation signal is not really spectrally white, but it is a pattern of air bursts (for vocalized speech) that take place at a rate of 70 to 200 times per second. Second, the complexity of the vocal tract model changes as a function of voice patterns with the lips opening and closing, the nasal tract opening, the tongue touching the palate, and several other important organ configurations. Third, there is an inherent limitation in estimating both the tract model coefficients and the excitation source with an all pole LPC model from one acoustic signal. The reason is that zeros in the excitation function (i.e., zero air flow) and anti-resonances in the tract model (i.e., zeros in the transfer function) cannot be mathematically modeled with LPC, and their presence can not be measured unambiguously using a microphone. As a result, the presently estimated Cepstral (i.e., LPC derived) coefficients representing the transfer function which characterize the vocal system of a speaker are inaccurate and not uniquely correlated with only one specific articulator configuration. Such errors in the feature vector coefficients directly limit the statistical pattern matching performance. Thus searching for a better matching algorithm or using more computer processing power to enhance performance may be futile. In addition, artifacts associated with ambient noise, speaker articulation variations from day to day, and speaker to speaker variability add difficulty and also training expense. Finally, developing large vocabulary systems for multiple, natural speakers, in many languages, is very expensive, because automated techniques for this process can not be well defined. It has been estimated (Rabiner and Juang, "Fundamentals of Speech Recognition", p. 493, Prentice Hall, 1993) that using the best models, it will take 10 CRAY YMP-16 equivalents to do the highest desired quality speech recognition.

It has been long recognized by linguists and phoneticians that human speech organ motions and positions are associated with the speech sound. Olive et al. "Acoustics of American English Speech", Springer 1993, describe the vocal system for almost all singles, pairs, and triplets of phonemes in American English, and their associated sonograms. Many decades ago, workers at Bell Laboratories (see J. L. Flanagan "Speech Analysis, Synthesis, and Perception" Academic Press, 1965) used x-ray images of the vocal organs and detailed modeling to determine organ shapes for given sounds. These workers and others described how optical devices were used to measure the glottal area (i.e., vocal fold positions) vs. time for voiced speech, and published detailed models of the speech system based upon well understood acoustic principles.

All of these physical measurement techniques suffer from not being usable in real time, and the detailed models that connect the organ information into phoneme identification don't work because the primary organ measurements are not available in real time. Therefore the models can not be accurately or easily fit to the speaker's macroscopic characteristics such as vocal tract size, compliance, and speed of speech organs. In addition, very idiosyncratic physiological details of the vocal tract, such as sinus cavity structure, cross sectional pharynx areas, and similar details, are not possible to fit into present model structures. However, they are needed to quantify more exactly individual speech sounds. Nevertheless, the above studies all show that associated with any given speech phonetic unit (i.e., syllable, phoneme or PLU) the speech organ motions and positions are well defined. In contrast, however, these workers (e.g., J. Schroeter and M. M. Sondhi, IEEE ASSP, 2(1) 133 (1994) and references therein) also have shown that acoustic information alone is insufficient to do the inverse identification of the speech tract organ configuration used to produce a sound. It is this incapacity, using acoustic speech alone, that leads to many of the difficulties experienced with present speech recognizer systems.

Researchers have searched for methods to measure the positions and shapes of the vocal tract elements during speech, but have found no effective way of doing this in real time. Papcun of Los Alamos National Laboratory described a vocal-tract-constrained speech recognition system, in the Journal of the Acoustic Society of America, 22 (2) August 1992, pp. 688–700, "Inferring Articulation and Recognizing Gestures from Acoustics with a Neural Network Trained on X-Ray Microbeam Data" and in PCT/US91/00529 titled "Time Series Association Learning." He measured vocal organ motions and their constrained patterns and locations, by using low power x-ray images of gold balls glued to a subject speaker's tongue and other vocal organs. He used this information to improve recognition algorithms based upon conventional mathematical techniques, but with additional phoneme pattern constraints imposed by the measurements obtaining using x-ray data. His algorithms are based upon allowed vocal tract motions, but do not use the motions in real time to enhance the word recognition reliability. He also showed that vocal organ positions and sequences of positions were uniquely associated with many speech sounds. However, it is both dangerous and impractical to consider using small x-ray machines or real time speech recognition.

U.S. Pat. No. 4,769,845 by H. Nakamura, issued Sep. 6, 1988, describes a "Method of Recognizing Speech Using a Lip Image". Several such patents describe electro-mechanical-optical devices that measure speech organ motion simultaneously with acoustic speech, e.g., U.S. Pat. No. 4,975,960. In this case, the formation of the lips helps define the identification of a phoneme in a given speech period, by the degree to which the acoustic identification agrees with the lip image shape. Such devices are helpful, but sufficiently expensive and limited in the information they provide, that they are not widely used for speech recognition. They have been proposed for the purpose of synchronization of lip motions to movie or video frames for the purpose of automatically synchronizing speech to images.

U.S. Pat. No. 4,783,803, 1988 "Speech Recognition Apparatus and Method" by Baker et al. assigned to Dragon Inc. (a prominent U.S. speech recognition company) lays out the details of a modern all acoustic speech recognition system, followed by six more patents, the latest being U.S. Pat. No. 5,428,707, 1995 "Apparatus and Method for Training Speech Recognition . . . " by Gould et al. Similarly Kurzweil Applied Intelligence, Inc. has patented several ideas. In particular, U.S. Pat. No. 5,280,563 by Ganong in 1994 describes a method of a composite speech recognition expert (system). This patent describes how to use two separate sets of constraining rules for enhancing speech recognition—an acoustic set of rules and a linguistic set of rules. The probabilities of accuracy (i.e., "scores") from each system are combined into a joint probability (i.e., "score") and a multi-word hypothesis is selected. This method of joining constraining rule sets is common in speech recognition.

EM SENSORS

U.S. Pat. Nos. 5,345,471 and 5,361,070 by Thomas E. McEwan at LLNL describe a micropower impulse radar (MIR) receiver and motion sensor based on very simple, low cost electronic send-and-receive modules that have millimeter resolution over measuring distances of 10's of centimeters to meters. These devices can be used for wood or metal "stud-finders" in building walls (U.S. Pat. No. 5,457,394), for automobile collision or obstacle avoidance radars, and for many other applications. In addition, McEwan, and others, have shown that the EM waves emitted from these devices at frequencies near 2 GHz (and at other frequencies) can propagate through human body tissue. He has also shown, Ser. No. 08/287,746, that such a propagating wave experiences enough of a dielectric (or more complex) discontinuity between human tissue and blood (e.g., heart) or human tissue and air (e.g., lungs), that the time varying reflected signal from a beating heart or other body organ motion can be detected and has value.

Professor Neville Luhmann, Director of the Department of Applied Science of the University of California at Davis, has described how low cost, solid state millimeter wave generators similar to the designs of McEwan and others can be made using microelectronics fabrication techniques. These can be fabricated into transmit-receive modules which provide millimeter resolution, and which can be tuned to optimize body transmission and minimize body tissue heating, or body chemical resonances.

U.S. Pat. Nos. 5,030,956 and 5,227,797 to Murphy describe a radar tomography system for examining a patient for medical purposes. A radar transmitter capable of transmitting rf or microwave frequencies is used with multiple receivers and time of flight timing units. The locations of body organs are measured from multiple depths into the patient and from multiple directions using both a multiplicity of receiver units (multistatic system), and by moving the transmitting unit to view the patient from multiple directions. A reflection tomography device uses EM wave reflections to build up an image of the interior of a patient's body for medical imaging applications. There is no description of the importance of time varying organ interface information, nor of the value of single directional, non-imaging systems. Murphy provided no experimental data on image formation that show his ideas can be reduced to practice, and several of the proposed embodiments in the Murphy patent are not expected to be technically realizable in any commercially important imaging system.

U.S. Pat. Nos. 3,925,774 to Amlung and 4,027,303 to Neuwirth et al. describe small radar units generating frequencies that can pass through human body tissue. Amlung describes a printed circuit board sized radar device made from discrete components that project rf waves in a particular direction at a frequency of about 0.9 GHz. The principle of operation is that as long as there is no change in the reflected rf signal to the receiver unit from any objects in the line of sight of EM wave propagation within a defined time unit, appropriate filtering in the receiver provides a null signal to an alarm device. If an object moves into the field of the transmitting device at an appropriate rate, greater than the filter time, a signal is detected and an alarm can be made to drive a sounding unit. This device is called a field disturbance motion detection device. It and several other devices referenced by Amlung as prior art could have been used to detect vocal fold and other vocal organ motions as early or earlier than 1975 in a fashion similar to the present invention. Neuwirth et al. describe similar devices.

Although it has been recognized for many decades in the field of speech recognition that speech organ position and motion information could be useful, and radar units were available to do the measurements for several decades, no one has previously suggested a speech recognition system using transmitted and reflected EM waves to detect motions and locations of speech organs and to use the information in an algorithm to identify speech.

SUMMARY OF THE INVENTION

Accordingly it is an object of the invention to provide method and apparatus for speech recognition using nonacoustic information in combination with acoustic information.

It is also an object of the invention to provide method and apparatus for speech recognition using electromagnetic (EM) generating, transmitting and detecting modules.

It is also an object of the invention to provide method and apparatus for speech recognition using radar.

It is another object of the invention to use micropower impulse radar for speech recognition.

It is another object of the invention to use the methods and apparatus provided for speech recognition for the purposes of speech quantification, mathematical approximation, and information storage for other speech related applications.

The invention is method and apparatus for nonacoustic speech recognition (NASR) in which nonacoustic information obtained by RF wave, microwave, millimeter wave, infrared, or optical wave electromagnetic (EM) measurements of speech organs is combined with conventional acoustic information measured with a microphone. The EM wave requirement is that it reach the speech organ being measured. The nonacoustic and acoustic signals are combined using an algorithm to produce more accurate speech recognition than obtainable only from acoustic information. The NASR information and the acoustic information, as needed, is also available for use in other speech technology applications, such as speaker recognition, speech synthesis, and speech telephony.

The nonacoustic speech recognition system includes EM generator-detector systems that can operate in the nonradiating near field, the intermediate (i.e., both radiating and nonradiating) field, and the radiating far field of the antenna structure(s). Radars are normally considered to use radiating EM waves that "leave" the antenna and propagate into the far field. However, because of the close positioning of EM sensor systems to the vocal organs described herein, all three types of EM wave field systems can be used for the methods and apparatus described herein. When the word transmission is used herein it is meant to describe the propagation of EM waves after they are generated and as they reach an antenna-like-structure where they develop a time varying near-field, intermediate, or far-field (e.g., radiating) pattern of electromagnetic fields. Human tissue is transparent, to the degree needed for the methods herein, in many EM wave-bands—from <$10^8$ Hz to >$10^{14}$ Hz.

1) EM wave generator—All configurations of EM wave generator modules that meet the frequency, timing, pulse format, position, tissue transmission, and power (and safety) requirements can be used. EM wave generators which operate in the (nonradiating) near field, the intermediate field where the wave is both nonradiating and radiating, and the far field radiating (i.e., radar) condition of the antenna may be used. In particular microwave radar modules operating at 2.5 GHz and with a 2 MHz pulse repetition rate have been used, and these units have been shown to be safe for routine human use. They have also been shown to be portable and very economical. The speech recognition experiments have been conducted using radar transmit/receive units in 4 different configurations. Speech organ motions have been measured simultaneously with a variety of sensor configurations ranging from three radar units and one microphone and as simple as one radar unit and one acoustic microphone signal. Improved methods of directing the transmitted EM radar wave into the head and neck have been developed, as well as several antenna designs and beam polarization options for speech recognition and other related applications. Methods to use varying phases, varying wavelengths have been considered, and multiple simultaneous wavelengths (e.g., impulse radars) have been used.

2) EM wave detectors—Four different EM wave detector or receiver modes have been demonstrated for speech recognition, i.e., CW reception, single pulse moving range gate reception, multiple pulse fixed range gate reception, and homodyne reception, and other receiver modes have been identified. Each specific receiver type is matched to a transmitter type, and is usually mounted on the same circuit board (or chip) as the transmitter. The receiver can be fed by an antenna separate from the transmitter or it can be connected, using a transmit/receive switch, to the transmitter antenna if timing allows. In one demonstrated mode, a circuit in the transmitter/receiver module compares the phase of the returned received wave from the speech organ to the initial transmitted wave, thus making a "homodyne" system which works well in obtaining organ motion information. This is known as a type of "coherent" radar when the object detected is in the far field, and can be viewed as a type of an interferometric device when the object is in the near or intermediate EM antenna field. The timing of the receiver "range gate" (when used) is controlled by a control unit, and has been demonstrated by placing the range gate circuit on the transmit/receive board. Received signal information can be due to reflections from interfaces and from attenuation due to losses in the propagation path and from multiple reflections.

3) Configuration structures, antennas, and control system—Five different methods of holding and supporting, simultaneously, several EM sensor units and microphones against the human face and neck have been considered (front, side, top, and back of head and neck, and under the jaw), including a harness such as a telephone operator uses, a covered enclosure such as used by a court reporter, a hand held unit such as a calculator, a telephone receiver with modification for under chin EM sensor modules, and a laboratory structure for carefully positioning such units for instrumentation purposes to a specific body shape. It is not necessary that the transmitter and the receiver be attached to each other or to the user, but can be mounted in any convenient place nearby such as on the dashboard of an automobile. This positioning at a distance from the speech organs requires proper focusing of the generated wave and/or tracking of the user. For the purposes of focusing, phased array transmitters or receivers, multi-element antennas, and other techniques well-known to the radar community, may be used for the purposes of focusing and tracking.

A control system is used to start the system upon acoustic or other input, to set the timing of the range gate of the receiver switch, to set the pulse repetition rate of the pulsed transmitting EM sensor units, that control the acquisition of the received EM wave information in a sample and hold unit, and to averages the data to improve statistics, that directs the held data into a memory, and that resets the system for another cycle. In other designs for nonacoustic speech recognition systems, the control unit would set the desired frequency of each transmitted pulse, the phases of the transmitted waves in the transmit gate, and other similar functions. Such a control unit is a vital part of the system, but it is relatively straight forward in its construction (it can be on one chip or several chips). Simple versions of such a control system have been implemented using timing circuits on the presently used transmit/receive chips (circuit boards), and the sample holding and display is done in conjunction with laboratory equipment, such as storage oscilloscopes and computer A/D conversion boards and readouts.

4) Processing units and algorithms—For each set of received EM wave signals there is a need to process and obtain the information on organ motions (or their new positions) that can be used to associate the unknown speech with the intended speech sound or word sound. For example, information on the position of the lips, jaw, teeth, tongue, and vellum can be obtained by transmitting in a horizontal direction from a range gated EM sensor (i.e., radar) system, as well as from other types of EM sensors each of which view a human subject's speech organs from different directions. The received signals from the speech organs are stored in a memory and processed every speech time frame, 10 ms (nominally), the time taken for a speech organ position to change to a new position for the next new word. The actual speech frame can be adapted to optimize the data processing system. The user can measure the vocal organ condition changes which determine when the speaker has altered the vocal system to make a new sound by using simple threshold tests, and thus the user can automatically define the beginning of a new speech time frame. The use of vocal organ information for adaptively determining the speech time frame permits the user, for the first time, to automatically associate the speech output with a constant excitation function and time independent vocal tract condition to obtain the clearest data set possible. In addition, the user may wish to associate the feature vectors from a sequence of time frames together into a multi-time frame feature vector. Finally, system control information can be added as additional coefficients to any feature vector, to identify trained feature vectors with acoustic speech units (e.g., PLUs, etc.), to optimize the search speeds, to keep track of pauses and memory locations, and similar housekeeping activities.

The algorithms normalize and digitize the EM sensor signal intensities and identify one of a few EM signal structures with known reference locations such as the skin under the jaw or the face front. The algorithms then take raw vectorized data, and normalize, quantize, time align, time compact, and construct a normalized vector for each series of signals, with control information, that correspond to a given organ's configuration at each frame of simultaneously measure acoustic speech. Then a comparison can be made against standardized numerical feature vectors in libraries using well-known comparison systems (used often in acoustic speech recognition processors). An example of such a comparison is to make it against a known organ motion or location data set for each of the 50 American English speech PLUs (or similar acoustic units). A positive match of the unknown feature vector against the appropriate coefficients of a known feature vector associated with a recognized word-sound in a library yields a recognized sound unit, which are often defined as syllables, phonemes, or phone like units (PLU), other acoustic speech units, words, or phrases. This method of feature vector description for each time frame can be extended to sets of sequential time frames such as diphones, triphones, whole words, and phrases for more complex sound unit identification. In addition, this method makes possible automatic library generation from spoken feature vectors associated with known acoustic speech units.

While the examples herein are for American English speech, the methods are applicable to all natural human languages, to other human sounds, to certain animal communications caused by structures measurable by the methods herein, and to human vocal organ motions associated with synthetic communication techniques such as moving of the tongue to direct a wheelchair, to move a cursor on a CRT screen, or to turn on a cellular telephone.

The bases of the following algorithms rely on two primary factors:

i) The techniques of nonacoustic, EM sensor derived speech organ position and motion measurement are statistically independent of acoustical speech measurement using a microphone. Thus, the two sets of information complement each other in a statistical measurement sense. In particular, the EM signal can show articulator and thus phonetic conditions directly, in contrast to the acoustic signal which contains a great deal of superfluous information in addition to the phonetic specific information.

ii) The EM sensor signals provide explicit evidence of specific articulator activities which are very difficult to reliably extract from the acoustic signal. Many speech organ motions are "hidden" and are not extractable from acoustic signals using mathematical techniques, or the moving organ does not affect the speech sound, or important organ motions often occur before or after the speech unit is sounded. Thus, the nonacoustic organ measurements provide important additional information heretofore unavailable for use in increasing the accuracy of speech recognition, coding of speech information, speaker identification, and measuring physiological properties of great importance to the speech technology community.

Illustrative algorithms used to implement the nonacoustic speech recognition information include:

4A) Location algorithms: Reflected EM wave signal amplitudes from known organs are measured from one or several locations on each organ every 10 ms (nominal measurement times), except for vocal cords which are measured nominally every 1 ms, or more often for higher resolution. Time of flight range gating is often used to determine the locations along a propagation direction. The data from many EM wave transmission pulses is averaged, corrected, normalized, quantized, time aligned (to a reference position) and stored in a series of (about 100) memory locations. A whole speech organ condition can be measured all at once or parts of an individual organ can be measured, such as measuring the motions and positions of the front of the tongue, body (i.e., blade), and the back of the tongue every 10 ms. In another example, the reflection conditions of the glottal tissues (especially the vocal folds) are measured every 1 ms, using a real-time algorithm, and these signals are normalized and formed into a feature vector. Often the feature vectors from sequential time frames are joined together to form a multi-frame, time dependent, feature vector. These feature vectors are compared against pre-measured tables of stored vectors of known acoustic speech units (e.g., code books or libraries) to allow association of the unknown measured organ data with a known organ condition. Such information can be measured, averaged, normalized, and/or preprocessed in several ways to reflect the linguistic information being matched For example, such feature vectors can be transformed using Fourier or other transforms in order to obtain more unique signatures or patterns. Other techniques include stretching the time or frequency scale, and taking the logarithm of the amplitudes for improved table (or other statistical) comparisons. By using data from several speech organs at once, one can resolve problems that occur when one of the organs is used by the body in the same way for several different sounds caused by another speech organ.

Normalization of specific organ reflection characteristics and the extent of organ travel (both in distance and in velocity) of an individual can be obtained by asking the speaker to speak series of known words and phrases that exercise the speaker's vocal system to the extremes needed (i.e., a training sequence). Thereafter, in each speech time frame, the feature vector coefficients describing the condition of each organ (or part of organ) relative to the full range of the speaking individual can be mapped against the known full travel or full velocity condition of a reference speaker or speakers. Similarly the highest and lowest pitch period extensions, as well as intermediate pitch values, of the speaker can be measured using several training words or phrases, and mapped to the pitch period range of a referenced speaker. These methods remove much of the individuality of speech from each feature vector making possible a more precise code book lookup process.

The above described associations of feature vectors can be done using phonetic association (i.e., pattern matching), HMM, neural networks or other well-known statistical techniques. Several of these techniques have been demonstrated on individual words. Similarly, using standard acoustic sound unit recognition techniques, acoustic feature vectors and identification data can be generated. These can then be combined with the EM sensor data to generate a combined feature vectors which can be compared against known tables of the combined data vectors for known sounds, using standard statistical and speech recognition techniques.

4B) Motion pattern algorithms: This algorithm works by using the speech organ location signals described above, sequential pairs of which are (for example) subtracted from each other every speech frame period, e.g., 10 ms. These changes as new words are formed, are divided by the time between measurements. The resulting velocities are compared to libraries of predefined acoustic pairs and of the "moving" sound units such as glides, diphthongs, and plosives. There are about 1000 normally used sound pairs in English (i.e., diphones). To search this relatively small number of sound pairs, takes much less than the nominal 10 ms time-scale between new acoustic time frames. These velocity algorithms are very important because the organ motion patterns for each PLU (or similar acoustic sound unit), or for patterns for sequences of PLUs are very unique. In addition, sequences of feature vectors of PLUs with associated timing information is very idiosyncratic to each individual and forms the basis for speaker identification algorithms.

4C) Sound cue algorithms: Unique speech unit indications, "cues", can be obtained by using one or more simplified versions of the EM sensor systems measuring one or a few speech organs, in conjunction with acoustic speech information. By using a single EM sensor to measure the presence or absence of vocal fold motions, one can provide valuable information to a speech recognition system to determine if voiced speech is occurring. Similarly a single jaw motion EM sensor can detect jaw and tongue motions in anticipation of speech, and tongue motions during speech can indicate certain phonetic conditions. Rapid tongue tip motions can confirm the sound /th/, or a Spanish trilled /r/, and rapid jaw drops can indicate plosives such as /b/ or /p/.

Vocal fold motions are particularly valuable because they enable the user of these methods to obtain pitch periods and define voiced time frames, all of which can be used in a post-processing mode to validate the presence of speech to detect noise, to validate voicing or no voicing of the sound, to measure rates of phoneme articulation, to distinguish between similar sounding PLUs ("ing" vs. "ine"), and other useful cueing information to supply missing information to conventional acoustic recognition systems (CASRs).

4D) Word signature algorithms: A series of EM wave signals transmitted and received during the articulation of one or more words can be collected, and processed during the total time of word articulation. Simultaneously an acoustic signal is obtained and processed into sequential frame feature vectors as well. For example, a multi-time frame, multi-sensor feature vector of 20 single frame vectors (each 10 ms describing 200 ms of speech) are articulator and time frame normalized. Then they are processed further if needed, for example transformed into time or spatial frequencies by typical transforms (e.g. Fourier, Z-transform). They are formed into vectors as normalized, multi-sensor, multi-time frame descriptors of a whole word. Such a vector can be compared, in a preprocessor or post-processor mode, to known vectors of identical construction formed during training periods of normalized words in limited vocabularies of several 1000 words.

Another simpler method is to use a conventional acoustic speech recognition system (i.e., CASR) to make a best decision on the word being spoken by the user. This identification decision is compared to similar decisions using EM sensor obtained word feature vectors. The EM sensor obtained data is used to validate the decision or choose between several alternative decisions made by the CASR. If the CASR selected word is validated, then the word is accepted as recognized with joint probability; if not, then a best guess among a small set of words confusing to the CASR system is made using data from the EM sensor generated data set. EM sensor data has been used experimentally to resolve the ambiguity in the words "sailing" vs. "saline" and "sixteen" vs. "sixty". This concept can be used on small and medium sized word sets, and can be extended to very large word sets of 20,000 to over 40,000 as computer memory and processor speeds improve.

4E) Model based algorithms: It is common practice in acoustic speech analysis to use models of the human speech organ system. These models are generally of the nature where an excitation source is known to drive an acoustic resonator tract, from whence the sound pressure wave radiates to a listener or to a microphone. There are two major types of speech, "voiced" where the vocal folds open and close rapidly providing periodic bursts of air into the vocal tract, and "unvoiced" where constrictions in the vocal tract cause air turbulence and associated "modified-white" air flow noise. (A few sounds are made by both processes at the same time). The human vocal tract is a complex linear acousto-mechanical filter that transforms the excitation noise source into recognizable sounds. Physically the acoustic tract is a series of tubes of different lengths, different areal shapes, with side branch resonator structures, nasal passage connections, and end point constrictions. As the excitation pressure wave proceeds from the source to the mouth (and/or nose) it is constantly being transmitted and reflected by changes in the tract structure. Research at Bell Laboratories (J. Schroeter and M. M. Sondhi, IEEE ASSP, 2(1) 133 (1994) and references therein) and elsewhere, studying the relationship of given speech sounds to the shape of human vocal tracts resonators, has shown that accurate knowledge of the excitation source characteristics and the associated vocal tract configuration can uniquely characterize a given elemental acoustic speech unit such as a PLU. This accuracy of these organ configurations can be conveyed by a small set of numbers formed as coefficients of a feature vector. It is also known that if a change in a speech sound occurs, the speaker has moved one or more speech organs to produce the change. Conversely, it is also known that using acoustic information alone, it is not possible to work backwards to uniquely determine the vocal tract condition and thereby uniquely define the acoustic unit intended for a given time frame of acoustic speech.

The use of EM sensor information makes it possible to define speech frames uniquely and to determine which type of excitation function occurs during each speech frame, and what its characteristics are. Transfer function information can be obtained by measuring the locations and dimensions of the speech organs, which in turn can be associated with many types of models. One model describes the mechanical and acoustic structure of the vocal tract that is general in nature. A simpler model uses EM sensor information that describes the constrictions and condition of the various resonators in an individual to determine the type of vocal tract in use during the speech time frame. Such models can be based upon general electrical circuit analogies for which extensive procedures have been developed to obtain transfer function values from measured data and whose coefficients can be used for feature vector formation. Finally, simple curve fitting models, such as polynomials or the LPC procedure, can be used. They are computationally easy to use and require relatively few parameters for an acceptable fit of the transfer function during the given speech time frame and over several sequential epics. The process for using a sound model is to use the EM sensor information to determine selected organ motions and positions, to obtain actual physical updating of the excitation function and vocal tract models for each speech time frame or sequence of time frames. A feature vector comprised of a relatively few correct excitation function and transfer function fitting parameters for each speech time frame will lead to a very high probability of correct word-sound identification.

A PLU that lasts for several speech frame periods (e.g., 100 ms with 10 ms per frame) yields multiple (e.g. 10) opportunities to construct feature vectors. If the feature vectors do not change by more than a user defined value, then a multiple time frame feature vector can be formed to minimize computing and storage. In addition, multi time-frame feature vectors can be used in the same way as just described for single, or slowly changing feature vectors. Because of the direct relationship between speech organ motion and sound, the model approaches provide a more fundamental parametrization of vocal system condition during speech than has been possible in the past. They also make possible, because of the capability of defining sequential speech frames, simplified descriptions of connected word sounds such as diphones, triphones, and whole words.

Once defined, and once libraries are constructed for the formats chosen, measured and formed feature vectors can then be used for subsequent word sound identification using many statistical techniques including phonetic-template pattern matching, Hidden Markov Models and others.

5) Post processing units:

5A) Comparison: Post-processors are used where identification information from an acoustic processor is joined with word sound identification information from the EM sensor speech recognition system (from one or several EM sensors). A joint decision using statistical techniques is then made using information from both systems. This post processing is necessary for algorithms 4C and 4D above.

5B) Spelling and grammar: Post processing computer units are used to further analyze the first level of identified speech. This first level of identification using the above described algorithms associates PLUs with speech sounds and speech organ motion, but does not provide perfect spelling or perfect grammar. These post-processing activities are presently used commonly in acoustic speech recognition systems.

5C) Security: As part of the post processing, the idiosyncratic characteristics of each speaker can be analyzed and compared (in real time) to a known record of the speaker's physical speech organ motion and shape properties, as well as the way the speaker uses his organs to say key sounds, such as passwords, his own name, etc. The EM sensor information makes it possible to add a very sophisticated identification process for security systems that is not possible with speech alone, because each person's speech organs have unique mechanical properties and the way they are used in concert—position vs. time—is unique for each individual as he speaks a known set of words or phrases.

6) Display units—Computer rendered speech recognition must be made available to the user for a variety of applications. A computer CRT screen is used to show the written word rendition of the spoken words, a speech synthesizer can be used to play back to the user the speech he just said so the speaker can validate his control instructions or the stream of words spoken into the machine. The data can be printed, placed on portable or fixed storage units, and sent via communication links as faxes, e-mail, and similar applications.

7) Keyboard or hand control units—Hand control units can assist in the instruction of the system being spoken to. The advantage of a hand control unit (similar to a "mouse") is to assist in communicating the type of speech being inputted such as control instructions versus data inputting, to assist in editing by directing a combined speech-hand-directed cursor to increase the speed and the certainty of control by the user.

8) Foreign language identification and translation unit— The statistics of organ motions and relative organ motions, together with simultaneous acoustic sounds, can be used to identify the speaker's language. If the speaker is asked to repeat a known sequence of words or phrases, then convergence on the speaker's language is more rapid because the test set is chosen to illustrate language distinctions. In addition, the same unit can be used to translate speech recognized text from one language, via a text to speech synthesizer into another language for transmitting to another person.

9) Auxilliary input unit—Other instrumentation that aids in recognition or requires synchronization, e.g., video, can be attached to the system with this unit. A transmission unit is also needed to communicate with other systems.

BRIEF DESCRIPTION OF THE DRAWINGS

FIGS. 8A,B are radiating systems and FIG. 8C is a near field system.

FIGS. 9A,B show simultaneous acoustic and EM sensor obtained vocal fold open/close data for the word "fox".

FIGS. 25A–H show the acoustic and EM vocal fold signal for the sentence "the quick brown fox jumped over the lazy dog's back."

DETAILED DESCRIPTION OF THE PREFERRED EMBODIMENTS

General Principles

Figure 1:
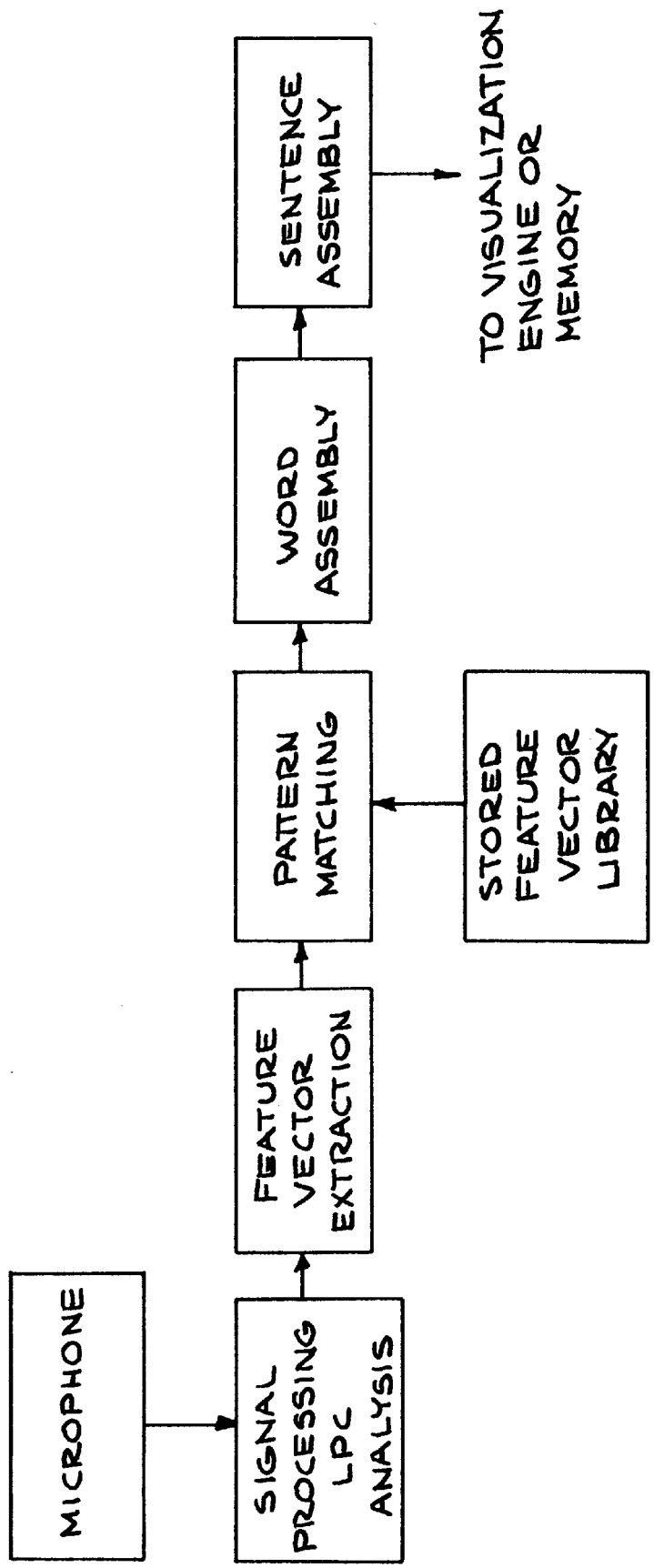
FIG. 1 is a schematic diagram of a prior art open loop acoustic speech recognition system.
Figure 2:
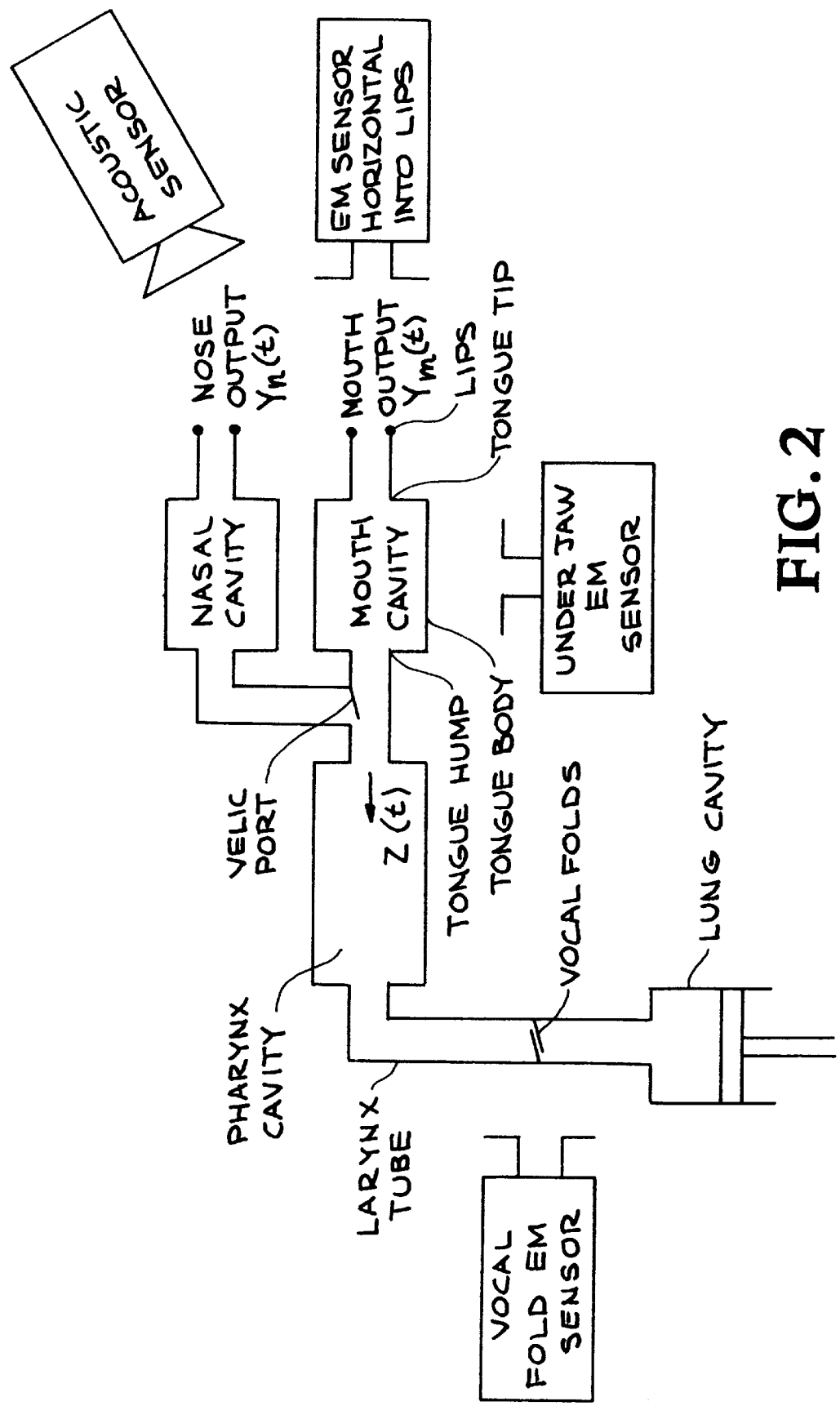
FIG. 2 is a schematic diagram of a vocal tract model with a combined non acoustic/acoustic speech recognition system using EM sensors and an acoustic sensor.

FIG. 2 shows a nonacoustic-acoustic speech recognition (NASR) system which is to be compared to a conventional acoustic speech recognition (CASR) system as shown in FIG. 1. By comparison, a prior art CASR system forms a feature vector solely from acoustic information, while the NASR system of FIG. 2 makes EM sensor measurements of a number of speech organs (vocal fold, velum, tongue and lips are shown) and then combines feature vectors describing these signals with feature vectors describing acoustic information to produce a more complex, more information-rich feature vector describing the speech unit time frame.

The generation of a sound really starts at the lungs which provide a source of pressurized air. The vocal folds, in voiced speech mode, modulate the air stream by opening and snapping shut to generate a stream of air bursts as excitation pulses. The on-off pulse shapes together with the resonating of the vocal tract structure, determines the speech sounds heard by a listener. The tract shape is governed by the position of many speech organs. The velum controls the fraction of the air flow diverted to the nasal cavity, and out the nose. The tongue positions specify resonant responses of the oral cavity, and most of the air constrictions, for turbulent air sounds called frication. Finally the lips act as both the acoustic aperture (and acoustic antenna)—controlling the end of the acoustic resonator, the air flow rate and thus sound intensity, as well as a turbulence generating frication constriction. The vocal folds (glottis) and lips (and nose sometimes) form two ends of a series of acoustic resonant chambers. Acoustic energy radiates both outward through the mouth (and nose) producing a signal $Y_n(t)$ from the nose and $Y_m(t)$ from the mouth, and some low level feedback $Z(t)$ propagages inward from acoustic impedance discontinuities.

Figure 3:
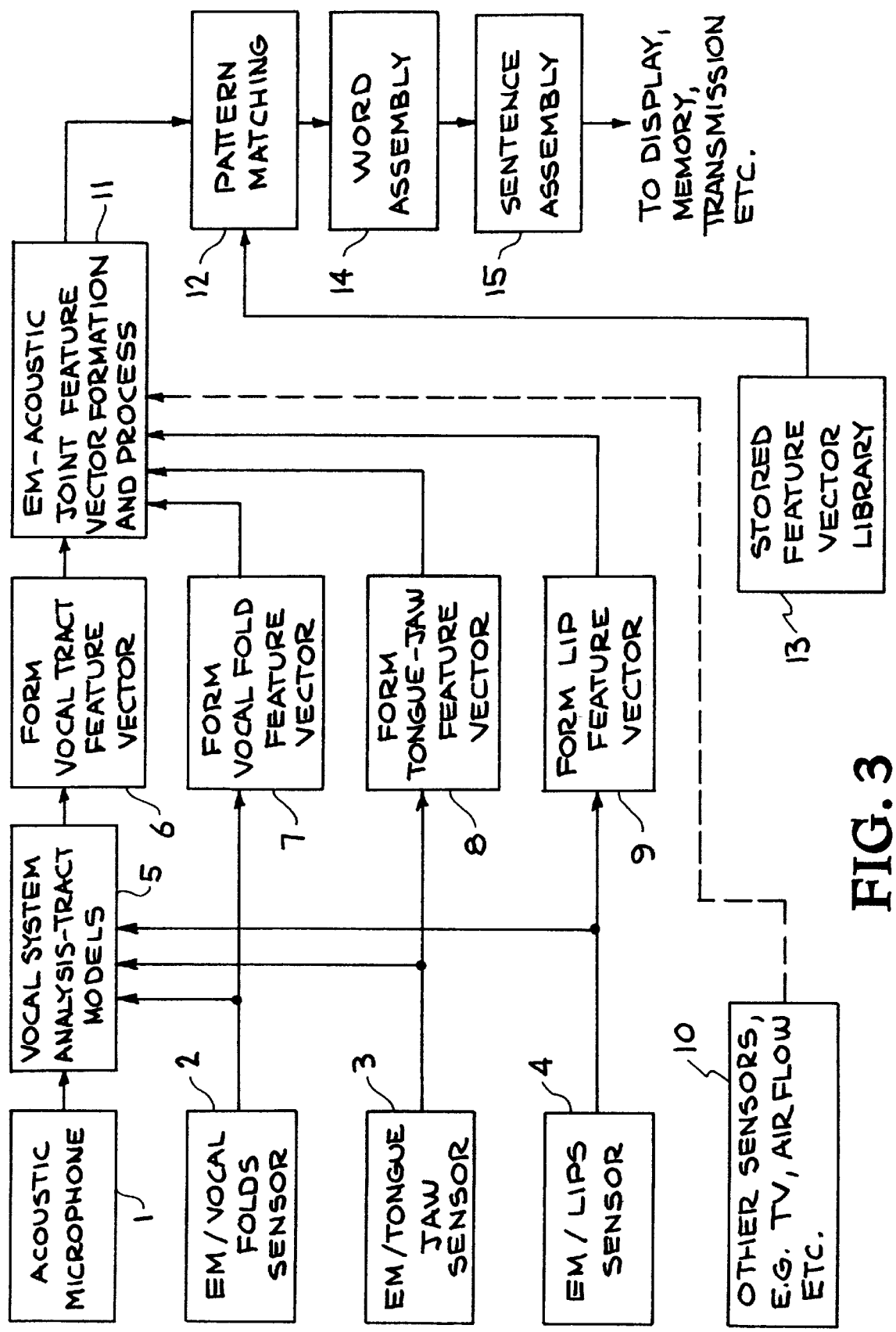
FIG. 3 is a schematic diagram of a speech recognition system using acoustic, plus several EM sensors whose data are combined in a joint feature vector.

FIG. 3 (multiple organ flow chart) shows a speech processing model based on the availability of RF sensors that sense the location of key organ positions. The extension to one or to a different suite of several sensors is similar and discussed later. The vocal cord sensor output signal is related to the true excitation signal of the vocal tract for which real time signals have never been available before. The speech processing model derived from knowing the action of the excitation source, together with the locations and degree of vocal tract areal change (including nasal opening via the velum) allows a much better and more accurate model of the vocal organ positions and motions during the speech time frame under measurement, and therefore a significantly better and more accurate representation of the feature vector coefficients. Similar measurements of the positions of other organs which participate in the definition of the vocal tract during a given speech time frame are associated with the PLU being spoken and provide a significantly better and more accurate representation of the feature vector coefficients.

In FIG. 2, signals from an acoustic microphone 1, and from three EM sensors 2, 3, 4 for vocal folds, tongue-jaw, and lips, are combined using vocal tract model 5 to form a vocal tract feature vector 6. The signals from sensors 2, 3, 4 can also be used to generate individual feature vectors 7, 8, 9. The feature vectors 6, 7, 8, 9 can be combined, with optional information from other sensors 10, to form a joint feature vector 11 which is further processed and normalized. By pattern matching 12 the feature vector 11 against a stored feature vector library 13 a sound identification is made. Finally, word assembly 14 and sentence assembly 15 can be performed and tested by word spellers, grammar and syntax correcting systems, and sent to where the user wishes.

Operational Modes and Control

There are many operational modes for the use of the EM plus acoustic detectors. In order to keep the EM irradiation of the human body low and within federal guidelines, and to minimize system power usage, especially for wireless systems, several techniques are used to control the ontime of the EM wave transmission module. Acoustic microphones can trigger "on time" to be coincident with speech sound generation; similarly, one can use infrequent EM sensor sampling to test for vocalization, and/or the use of a finger or other body part to actuate a button or similar sensor device to start the operation of the EM sensor system. In addition, the user selects EM sensor frequencies, pulse formats, and pulse format repetition rates to minimize EM interaction with the human body and to meet the needs of the speech recognition or related speech technology user.

Figure 4:
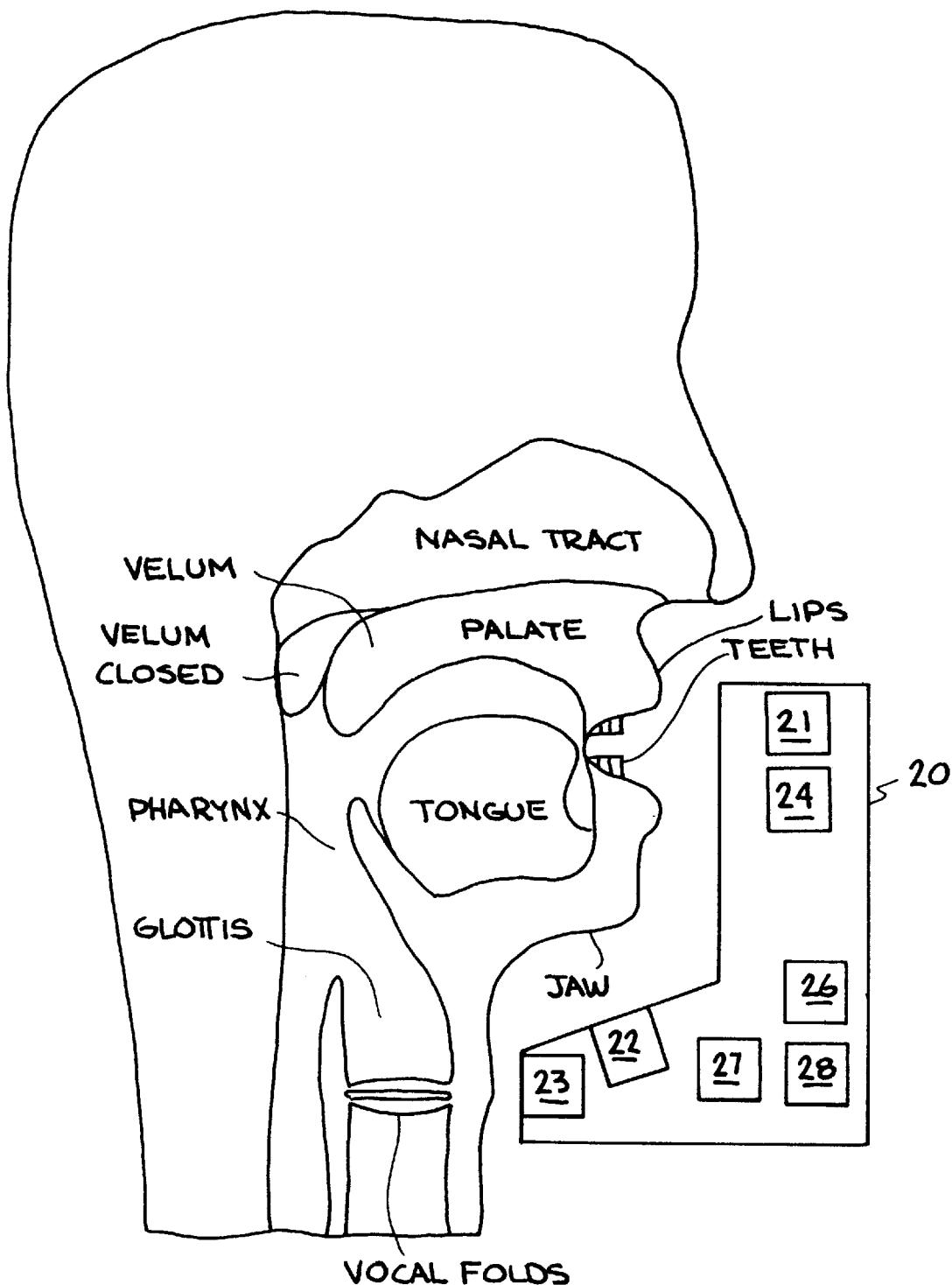
FIG. 4 is a cross sectional view of a head showing speech organs and position of a speech recognition module with three EM sensors and an acoustic sensor.

FIG. 4 shows a view of a head with relevant speech organs and an illustrative NASR sensor 20. Three EM sensor transmit/receive modules 21, 22, 23 are shown although there can be as few as one or more than three. Also a microphone 24 is used to obtain simultaneous acoustic information. Sensor 20 includes the necessary electronics, e.g. timing and range gate chip 26 and memory chip 27, as well as means to transfer the data over a wire or wireless, e.g. driver chip 28. Module 21 shows RF waves sent toward and back from the lips, teeth and tongue tip. Module 23 is directed at the vocal folds and glottis.

Module 22 shows a wave being launched upward toward the lower jaw, and into the lip palate organ region. The reflection of this wave back to the detector in module 22 would provide information on the "openness" or closed nature of the lower jaw with respect to the upper jaw, and the tongue with respect to the palate as a function of time. The measurement of lower jaw position is aided if the transmit-receive module is referenced to the upper jaw. This can be done by attaching the module to a head harness similar to that used for holding small microphones in front of the lips. A second approach is to measure the relative position of the lower jaw air-skin interface relative to the upper jaw palate or nasal cavity structures. Another approach to obtaining the reference position measurement is for the transmitter-receiver range-gate control computer to integrate (i.e., track) cumulative motions, of the relatively slow lower-jaw motions as time elapses (assuming that the jaw is moving slowly with general head motion), and to then measure, and form feature vectors from the rapid lower jaw movements associated with speech. The sensor used to track the slow motions and other EM sensor modules can measure the needed organ locations as a function of time during the vocalization process: such as glottal tissues (or simply vocal fold) open-close motions; tongue up and down motion; tongue fore and aft position; lips open and closed, and lower jaw up and down position. These examples are not meant to be an exclusive list of all such module positions, organ types, wiring arrangements, etc.

These processors are not shown with the necessary supports to hold them in place against or near the appropriate parts of the body. A variety of techniques can be used ranging from taped-on sensors, to a telephone operator-like microphone harness, to court stenographer-like mouth covers. Such mouth covers are especially well suited to hold EM sensors, microphones, and other specialized sensors (e.g., air motion sensors) if needed. The modules could also be held by a support unit(s) that is located further from the body. They might be on a steering wheel or visor in a car, attached to a microphone which is used by a person speaking, etc. The locations of the EM sensor generator and receiver modules (either separate or together) vs. head position will depend upon the value of the application, the additional cost of the modules due to the need for accurate speech-organ location as the distance from the speech-organ to the module increases, and the additional costs associated with tracking the speech organ/air interface as the module and body are increasingly less connected together. EM sensor ranging speech detection modules may be located against, near, separate from the body, and attached to or near microphones (either hand held, attached to harnesses, or as normally used on microphone stands), or included in head helmets (partial or full head covering), in mouth covers, and in other devices attached to or on parts of the body near to the head.

Figure 5:
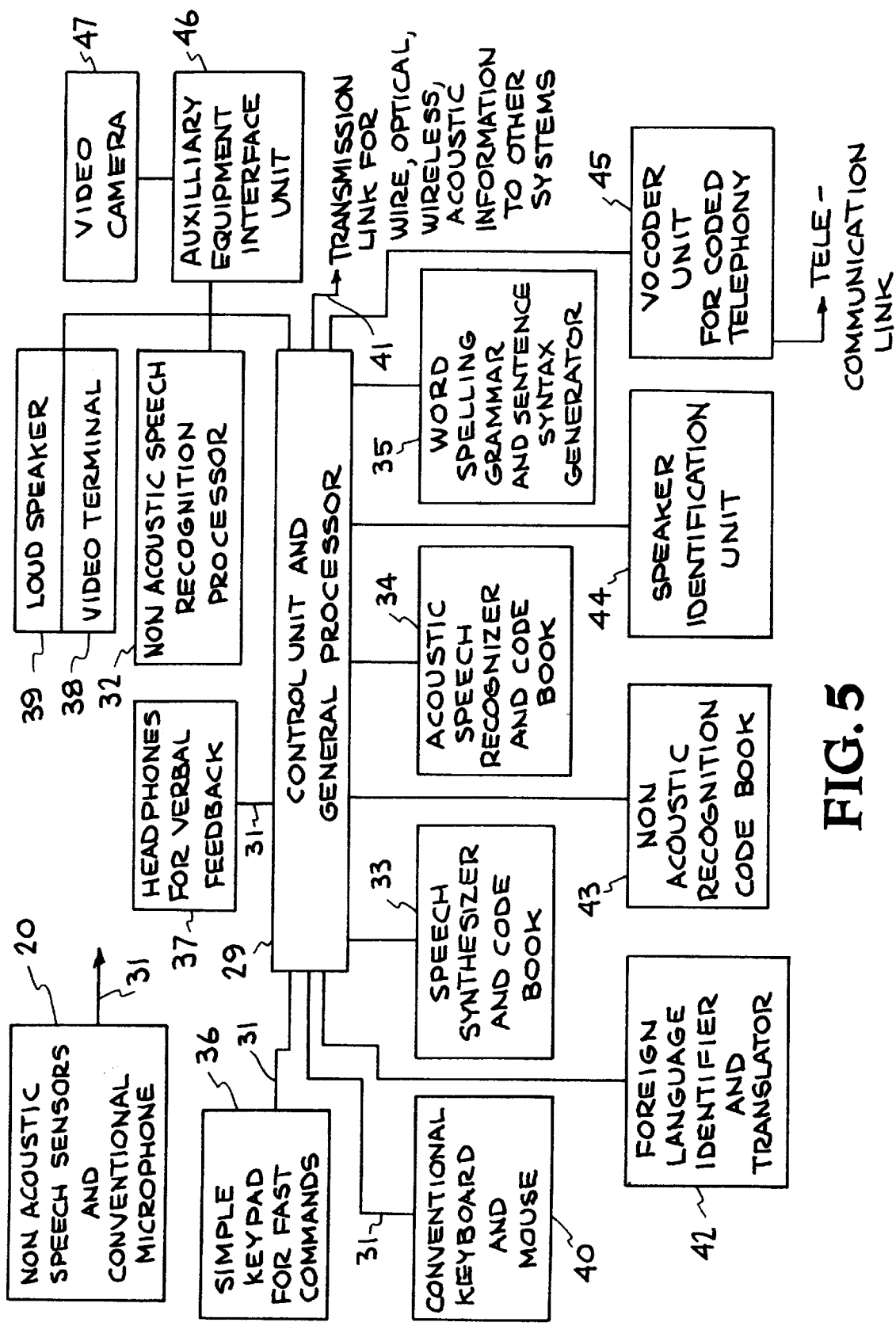
FIG. 5 is a schematic diagram of a NASR (nonacoustic speech recognition) system, with post processors, video input, and transmission line output.

FIG. 5 schematically illustrates a NASR system 30 using sensor 20 of FIG. 4, which includes both EM sensor and acoustic detectors. Sensor 20 is connected by a wireless (RF or optical) link or cable communication link 31 with a processor 32 and its associated peripheral equipment. Other equipment, e.g., video camera 47, can be interfaced to processor 32 through unit 46 for purposes of synchronization or added information. NASR processor 32 is connected to a control unit and general processor 29. Speech synthesizer unit 33, acoustic speech recognizer 34, word spelling and sentence syntax generator 35, foreign language identifier/translator 42, NASR code book 43, speaker identification unit 44, and vocoder unit 45, may be connected to processor 29. An input keypad 36, a keyboard or mouse 40, headphones 37 for verbal feedback, and video terminal 38 with acoustic loudspeaker 39 can also be connected to processor 29. Recognized letters and words, and acoustic signals can be outputed on wireless or cable links 41. The system is controlled and set up by control unit 29.

Figure 6:
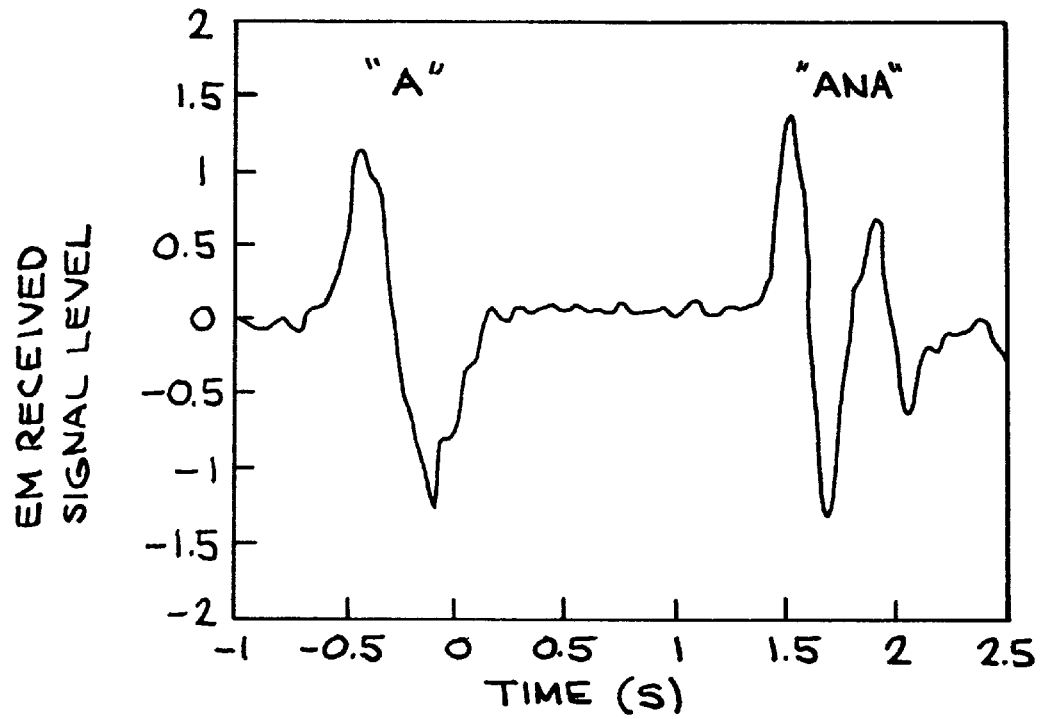
FIG. 6 shows an EM sensor response to jaw and tongue tip motion for the speech series "aaa" and "ana".
Figure 7:
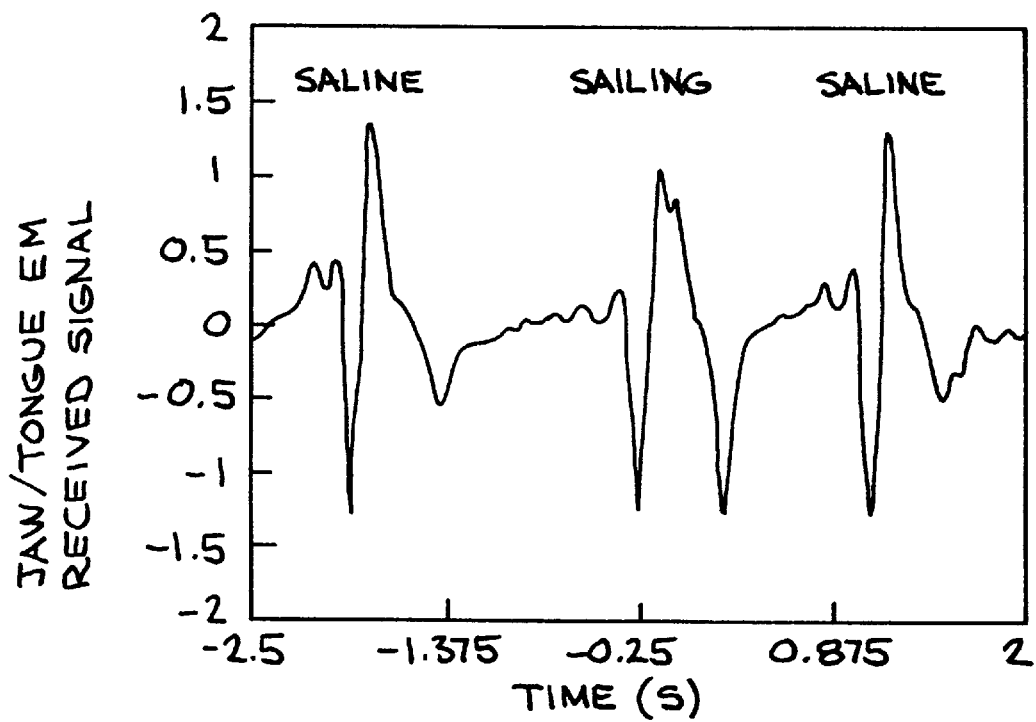
FIG. 7 shows an EM sensor responding to jaw/tongue tip motion for "sailing" and "saline".

An example of EM sensor response data is shown in FIGS. 6 and 7. An EM sensor (sensor 22 in FIG. 4) responds to tongue tip motion as a speaker says the sounds "a" and "ana". The EM sensor data in FIG. 6 clearly shows several major stages of speaking an open vowel, starting with opening of the jaw (upward signal), and closing the jaw/tongue after the sound /a/, downward signal, the tongue plays little role. For /ana/, the /n/ is accompanied by a fast, often poorly articulated, tongue lift between /a/ sounds, and the sequence is terminated by dropping the tongue and closing the jaw. FIG. 7 shows a field disturbance mode of EM sensor response to tongue locations for the similar sounds "sailing" and "saline", which are difficult to differentiate using conventional CASR approaches. In these two cases the different tongue positions associated with "ing" and "ine" are clearly shown by different reflectivities versus time. The movement of the tongue from the /l/ position to a back position for /ing/ causes a double bump in the positive signal portion and a much larger negative reflected signal as the tongue drops to say /ing/ compared to the waveform when the tongue makes the transition from /l/ to /ine/.

Non-Acoustic EM Sensor Principles

Generation, Transmission, and Reflection of EM Waves

Figure 8A:
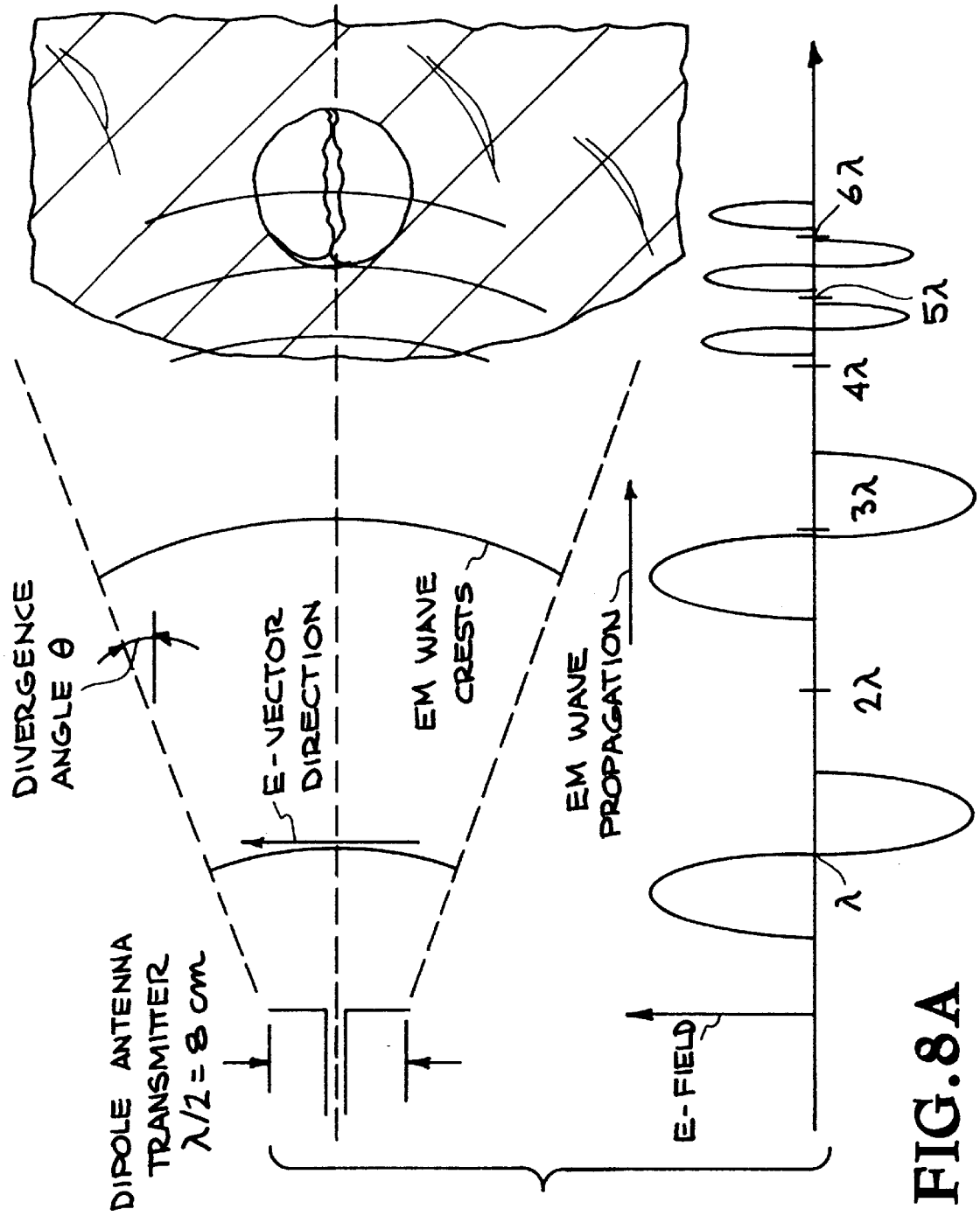
FIGS. 8A–C are schematics of EM pulses being transmitted to and reflected from the vocal folds in the neck of a speaker.
Figure 8B:
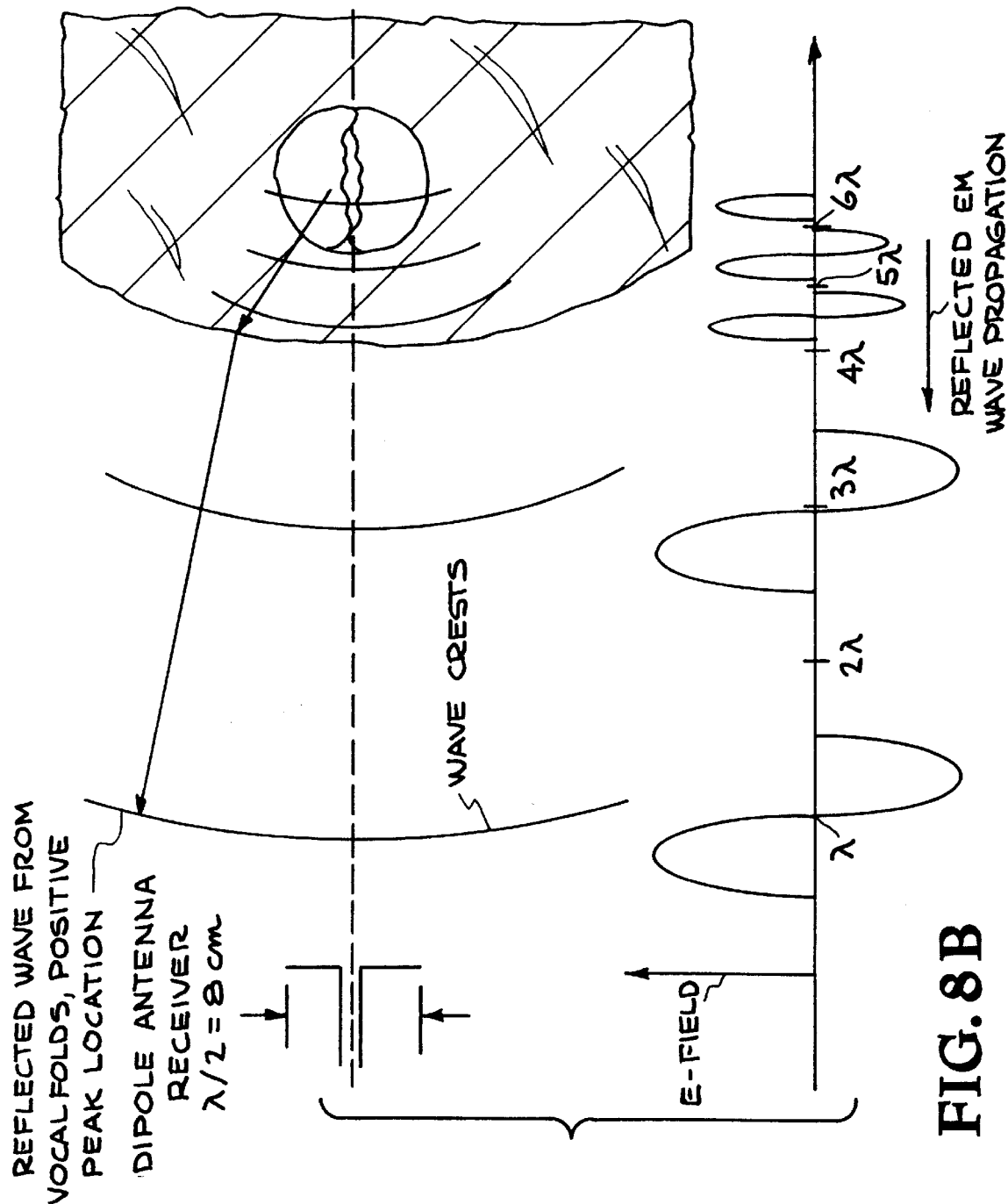
Figure 8C:
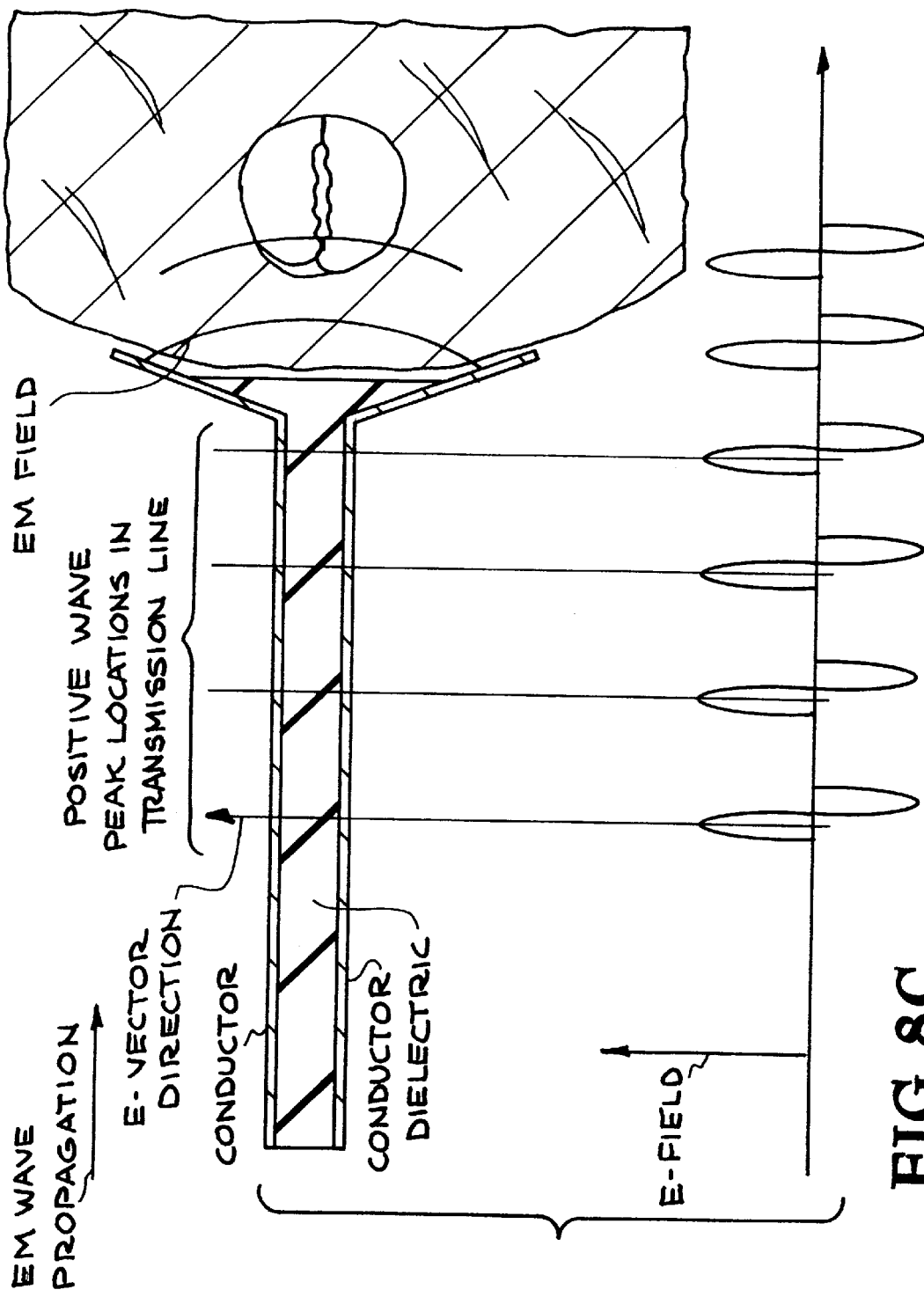

FIGS. 8A,B illustrate the transmission, radiation, and reflection of a single linearly polarized EM wave pulse from two illustrative locations along the propagation path. FIG. 8C illustrates a different arrangement where the EM wave is non-radiating and measures "near field" reflectivity variations. In the cases shown in FIG. 8A,B, the EM wave sensor system is a type of radar. The wavelength of the wave shortens as it enters the neck and the propagation speed "c" slows to c times $1/\epsilon^{1/2}$, because the tissue is a material with dielectric constant $\epsilon$ greater than $\epsilon_0=1$ for air. In addition, the amplitude of the electric field drops for two reasons. A significant fraction of the forward propagating EM wave reflects at the first surface, the air skin interface, and in a dielectric medium, the E field drops because of the high dielectric constant, $\epsilon$. The shortening and slowing of the wave makes it possible to measure the size and location of structures internal to the head that are a small fraction of each radar pulse length in air. Since it is common practice to measure distances to less than 1/10th of the EM pulse length dimension, one can detect structure interfaces that are 1/10 of a half wave pulse of 1.5 cm of the wavelength in the tissue, or 1.5 mm. More importantly, it is easy to detect changes in vocal organ interfaces, of less than 0.15 cm distance, as speech organ motion occurs between one set of EM sampling pulses to another set of pulses. In FIGS. 8A,B position changes are associated with motions of the glottal tissue motions (e.g.,vocal folds as they open and close) and change the interface locations and the degree of EM wave reflection. Experiments have shown position change detectability of less than 0.001 cm.

In addition to the single wave packet of a sinusoidal wave shown in several positions during its propagation in FIGS. 8A,B, other wave formats can be used for EM wave transmission, including using more wave cycles to improve the information obtained through reflection from vocal organ tissue each transmit/receive period. Different propagation directions can be used, and different orientations of the generator relative to the receiver can be used to determine reflections and attenuations of one or more EM waves as they sample the speech organs (including opposing orientations measuring transmission through the body). The transmitted waves can be composed of differing wavelengths or programmed series of waves with varying wavelengths, of wave packets ranging from partial to many wave periods, of step or spike pulse packets ("impulse transmissions"), of waves with randomly varying pulses (e.g., "noise" radar), and many others described in Skolnik "Radar Handbook", McGraw Hill, 2nd ed. 1990 and elsewhere. The EM sensor transmission packets can be optimized for the purposes of speech organ detection by enhancing resonance effects, by eliminating "speckle" (e.g., using quadrature techniques), by optimizing interferometric (e.g., homodyne) detection, and similar techniques.

EM Wave Detection and Processing

After an EM pulse (or pulse train) is received it must be processed, correlated with other pulses from other organs and correlated with acoustic data and fed to an algorithm which automatically selects a word-unit (e.g. PLU), and displays it to the user or customer. Because EM sensors easily generate over one million pulses per second (experiments have been done at 2 MHz pulse repetition rates), one can average 1000 pulses for each reflected range position, or for the purpose of interrogating with a different wavelength, etc. Then one can change to a new range, or wavelength, etc. and then average another 1000 pulses. Thereby, the user is able, for example, to measure up to 20 parameters during a typical speech time frame of 10 ms. (The speech time frame can be fixed or it can adapt to the changes in speech rate on the organ, e.g. vocal folds open and close each 5–15 milliseconds). FIG. 4 also shows a straight forward way of measuring the locations of many of the important speech organ interfaces from the front of a face through the back of the throat, up through the lower jaw, and into the neck. The interface locations at a given time can be associated with a given speech unit, e.g. PLU, and by knowing, in advance, a sufficient number of distinctive vocal organ locations for each speech unit one can identify the sound being spoken using NASR information alone.

However a less complete suite of EM sensors can strongly limit the number of phonemes consistent with the NASR statistics. By comparing this limited set with the small set of similar sounding phonemes identified by conventional acoustic techniques (i.e., CASR system), one obtains an increased probability of identifying the correct acoustic speech unit, i.e., syllable, phoneme, PLU. This approach works because the EM and acoustic sensors measure the properties associated with speech in entirely different ways (i.e., physically and statistically). Data obtained and calculations indicate a greater than 95% accuracy for all NASR organ measurements (and >99% for certain measurements). Experiments at the Lawrence Livermore Laboratory and elsewhere indicate 90% accuracy for CASR identification. Experiments show that such CASR errors are usually caused by a lack of distinguishing acoustic features often caused by incomplete or coarticulation. However the associated articulator motions are easily measured by the NASR system (see FIG. 6). Joint recognition statistics of both systems together will lead to speech recognition error rates of less than 1% in normal environments. Estimates indicate that the acoustic unit detection error rate will approach 1 phoneme in $10^4$ when sufficiently accurate EM sensors plus a microphone are used with advanced algorithms. This is highly accurate word recognition, approaching human hearing standards.

There are many situations where complete speech recognition knowledge of organ location and motion is unnecessary to improve the condition of present speech recognition technology. Such conditions are described herein in several of the algorithmic descriptions. In addition, several algorithms use the special information available from the EM sensors to provide new ways of recognizing speech in both specialized and generalized situations, e.g. word signature algorithms and motion pattern algorithms. They make use of the fact that PLU pairs (i.e., diphones) and PLU triplets (i.e., triphones), or larger PLU units (e.g., words) are known to adequately describe many of the coarticulation and incomplete articulation conditions in speech, and knowledge of these multi-phone units and their rates of delivery are known to be very useful for enhanced speech recognition accuracy. EM sensor data is especially useful in describing such PLU sets in a superior way to acoustics because, in contrast to acoustics, partial organ motions and positioning can be easily measured.

Types of EM Sensor Systems

Two general modes of radar operation for speech organ motion, in conjunction with acoustic speech detection, have been demonstrated:

(1) scanned range gating of short pulses demonstrated with radar modules (including the special conditions of no-gate, or one fixed gate condition), and (2) heterodyne (including homodyne as an often used special case) whereby detection of the phase change vs. time of the reflected waves is used. These two generalized modes, together with well known variations (see Skolnik "Radar Handbook" ibid.) and combinations of them, provide very convenient configurations for vocal organ measurements. In particular, 2 GHz frequency EM transmission modules were used to measure speech organ motion and to provide positions of interfaces and whole organs as a function of time. The 2 GHz wavelength (about 2 cm) propagates well in tissue (at least 20 cm) and reflects well off of the 25–80 to 1 dielectric discontinuities. The wave period of 0.5 ns lends itself to being used in a pulse format of several waves for whole organs (1–3 ns), down to a single wave or ½ wave pulse period (about 0.25 to 0.5 ns) for measuring specific interfaces in a range gate mode. While this example is based on one EM sensor module and one antenna, multiple modules and multiple antenna configurations can be used to obtain information from the organs from other "viewing" directions and can examine many specific organ interface locations for more descriptive feature vector construction in each given speech time frame. Interferences between modules are avoided by proper triggering control or because the actual wave transmission duty cycle per module is very low and therefore the chances of interference between modules is very low.

EM Field Disturbance Sensor

The simplest speech analysis system used to measure speech and speech organ motion is the field disturbance sensor together with a microphone and recording oscilloscope. The sensor works by processing changes in reflected EM signal levels from organs when compared to a time "average" reflection level. To measure a change occurring in a 1 ms time interval, the typical system will measure and average the organ conditions 2000 times Time filtering of such received and averaged EM signals allows very small reflection changes, in a given frequency or time band, to be detected in the presence of the very strong average background, which is characterized by slowly changing signals. Examples include measuring tissue distance changes, smaller than 0.001 cm, associated with acoustic pressure waves. Since the many interfaces in the vocal system and the head/neck structures are located at different ranges, and move at very different rates, the wave packet transmitted in the field disturbance configuration reflects off all the structures within the range gate time (and thus distance gate). As subsequent pulses are transmitted and as time progresses, one integrates and processes the returns from the sequence of pulses with one time constant, and by time filtering with a different time constant, the method allows the user to obtain information on many organ interface conditions as long as they move at different rates.

Figure 25D:
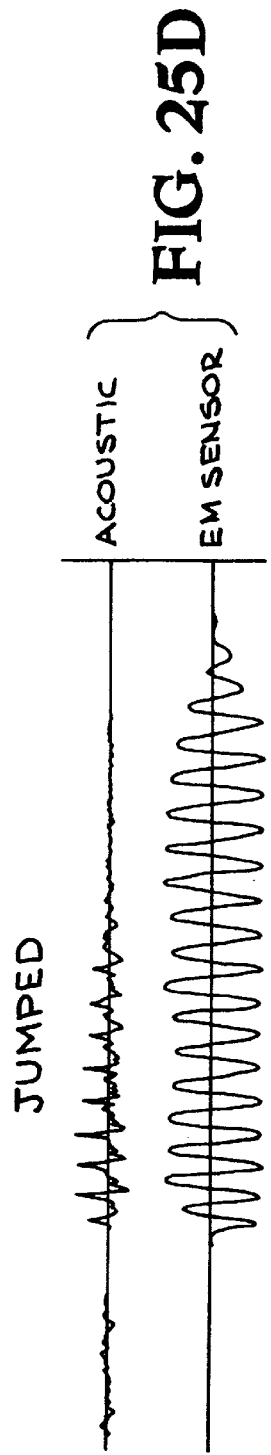
Figure 25E:
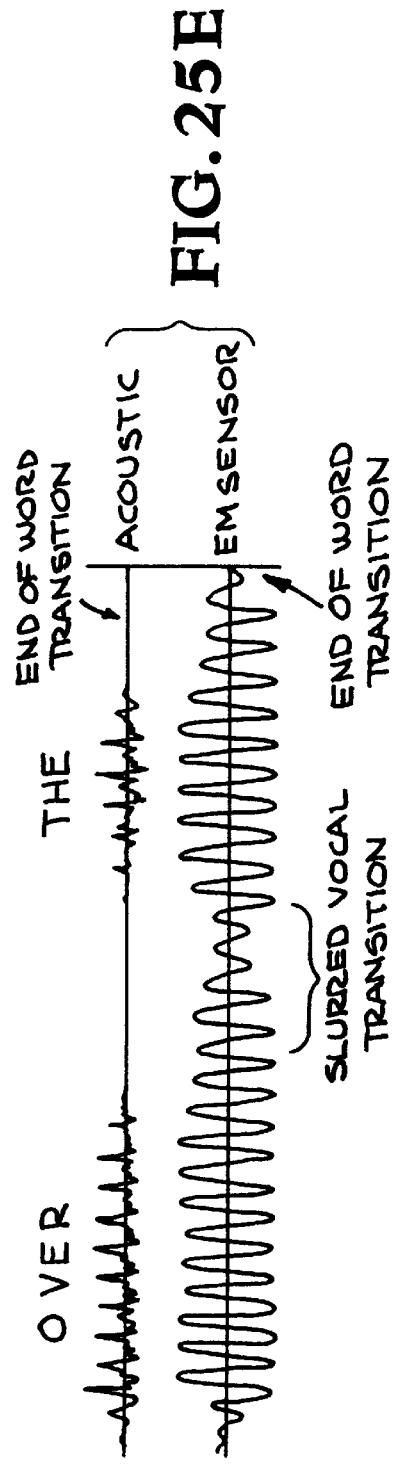
Figure 25F:
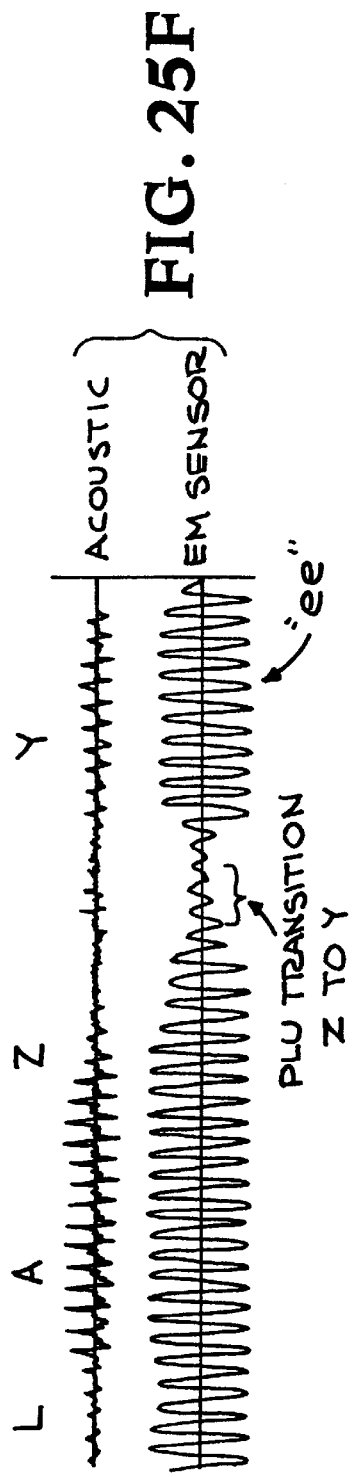
Figure 26A:
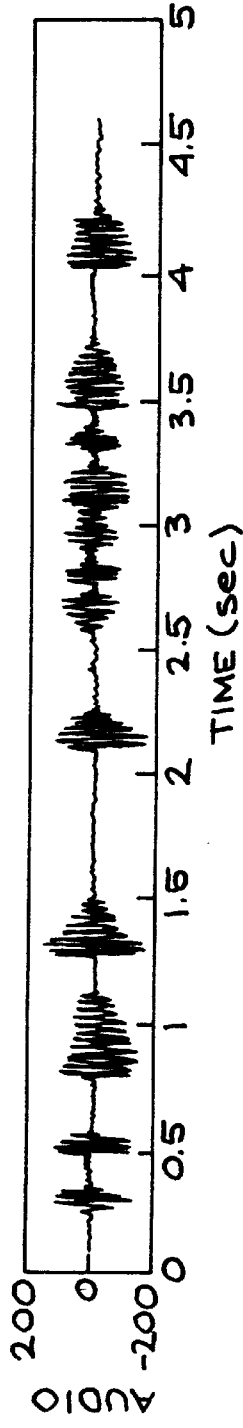
FIGS. 26A–D show the outputs of four sensors (positions shown in FIG. 4) for the sentence "the quick brown fox jumped over the lazy dogs back."
Figure 26B:
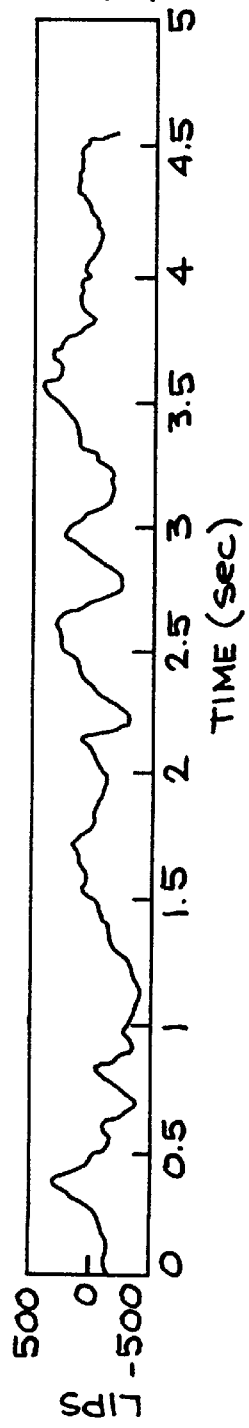
Figure 26C:
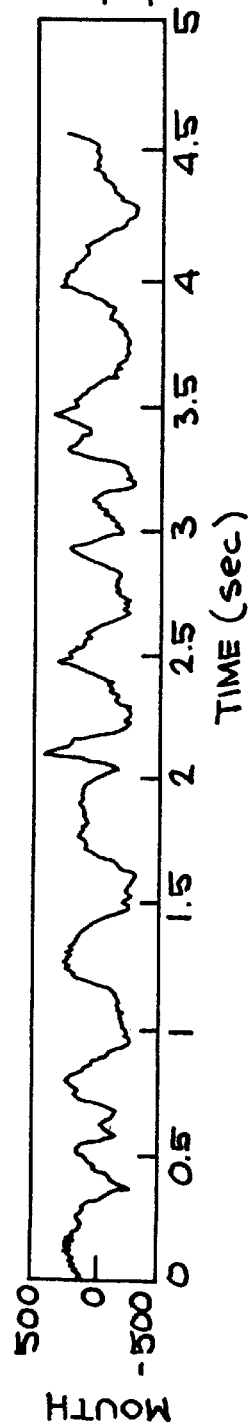
Figure 26D:
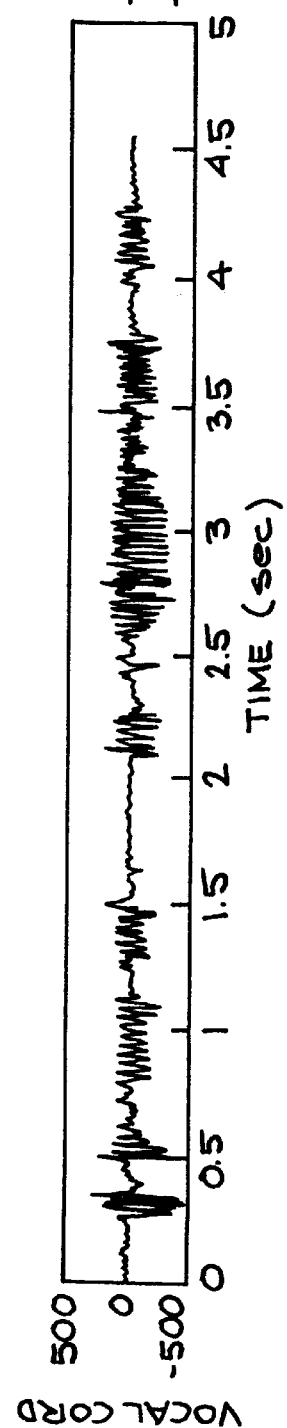

For example, the method can discriminate rapidly changing signals from normal, slow head motions. In particular, glottal tissue motions (which herein include vocal fold motions) are associated with vocal fold opening and closing. They are easily detected by frequency (or time) filtering such that signals in the 50 to 2000 Hz band are detected in the presence of strong, but slow moving skin/air reflections from the neck and head. Simultaneously acoustic speech signals, corrected for differences in time of flight, are also measured and recorded. FIG. 9A shows the acoustic signal and FIG. 9B shows glottal tissue motion signals for the word "fox." The /f/ in "fox" is an unvoiced first phoneme, and the "x" is a phonetic /k/ that shows a vocal fold "fry" transition sound to the end of the "x", which is an unvoiced /s/ sound. The /s/ sound extends beyond the range of the x-axis in FIG. 9A, but is shown more completely in FIG. 25C. FIG. 9B also shows how speech frames can be defined by changes in glottal tissue motion patterns; it demonstrates the simplicity and effectiveness of determining whether or not voiced (vocal folds moving) or unvoiced (vocal folds not moving) has occurred in each speech frame. One sees clearly, and it is easily discriminated algorithmically, the unvoiced /f/ and then the voiced /o/ and the transition /x/ in "fox".

Range Gated Operation

The user measures the presence of tissue interfaces by setting a fast electronic switch in the receive section of the radar module, called the range gate. This allows a sample to be taken from a received wave after a specified time, i.e., the round trip time from the transmitter to a reflecting interface and then back to the receiver. By conducting this measurement again, with a different time passage, one can measure the change in location of the speech organ interface as time (and as a spoken message) progresses. For example, the tongue tissue to air interface can be measured as the tongue is raised to say the sound /n/. By changing the time delay of the receiver sample time (called the sample gate or range gate) with respect to the transmitted pulse, one can determine the time delay to the tongue-air interface and back. It may happen that the round trip time corresponds to a location where there is no discontinuity and thus no reflected signal will be present. However, if the time gate is set such that a reflected wave is detected, the user then knows that an interface or discontinuity was present. It is clear that the user can direct the radar to change the timing on the receive gate in order to follow the motion of the interface as time evolves. This is done by transmitting successive pulses and by finding the location of the interface by changing the timing of the received pulses ("moving the range gate") until a received signal is noted. Such timing changes can be accomplished by using digital controllers or by using analog circuits such as timing generators. Since modern solid state EM sensor modules can transmit pulses at rates of a million times per second, and since the velocities of speech organs are relatively slow, requiring only 100 to 1000 samples per second to keep track of their interfaces, the scanned receiver gate (or range gate) mode of EM sensor (i.e., radar) operation can easily resolve and follow the location of the speech organ interfaces.

Figure 10A:
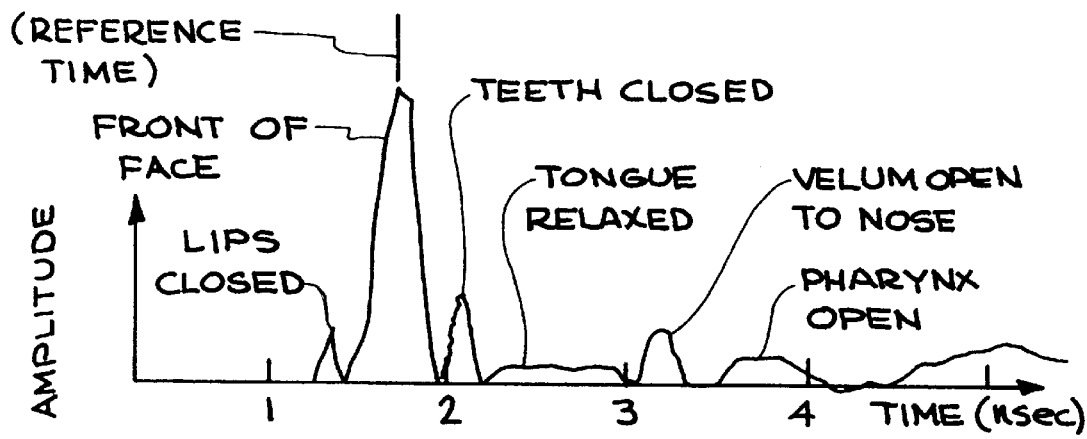
FIGS. 10A,B,C are illustrative representations of the received voltage signals from a single transmitted pulse reflecting from a series of speech organs as the organs move from rest to articulate the phonemes /t/ and then /o/.
Figure 10B:
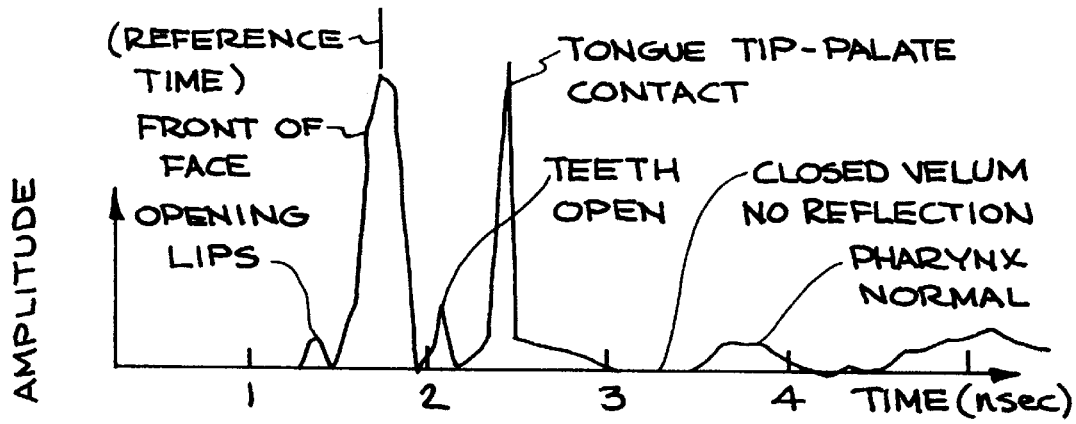
Figure 10C:
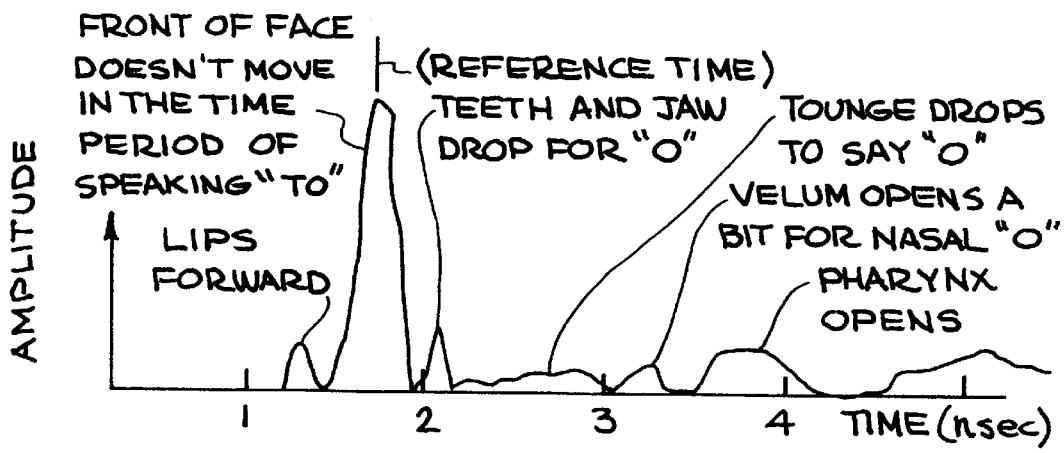
Figure 11A:
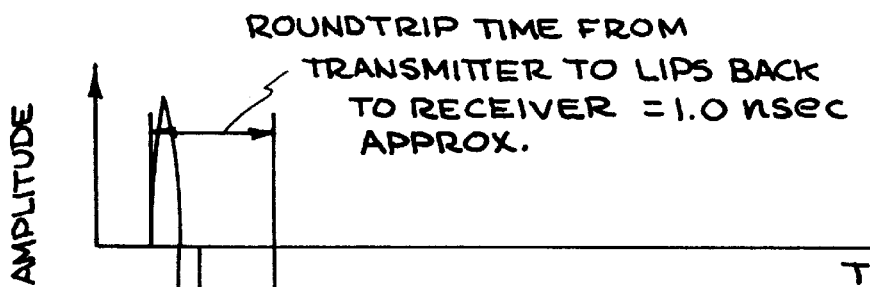
FIGS. 11A–D show a transmitted EM pulse, the reflected EM signal analog voltage from all organs in line with the pulse propagation direction, the location of the range gate, and the memory locations (i.e., bins) into which the digitized signal from the range gate switch is stored.
Figure 11B:
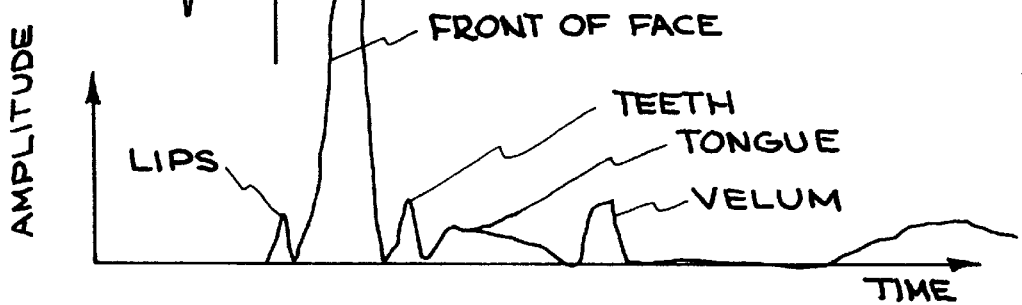
Figure 11C:
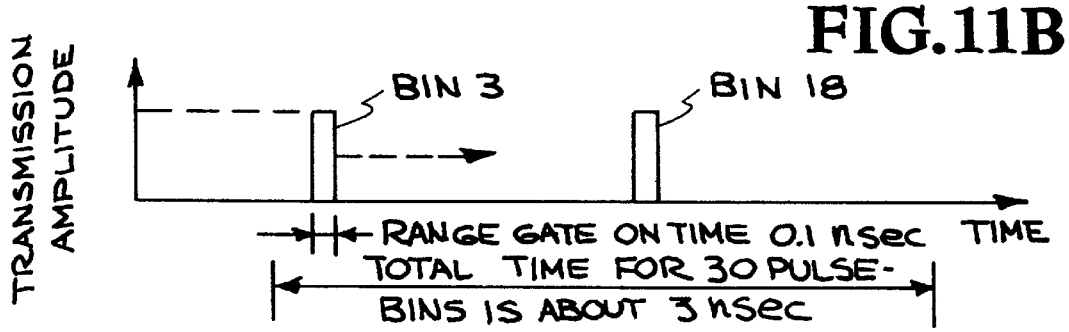
Figure 11D:
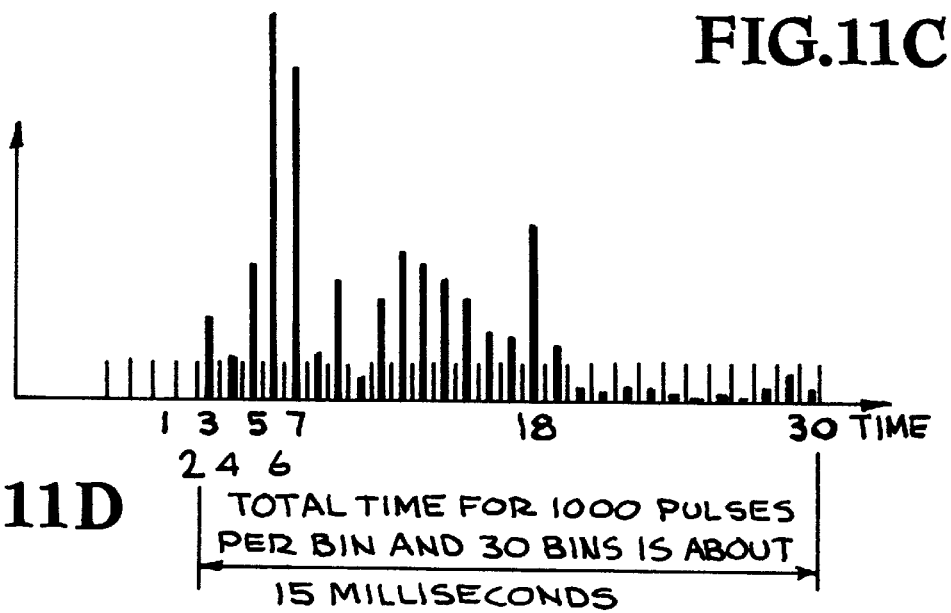
Figures 24A, 24B:
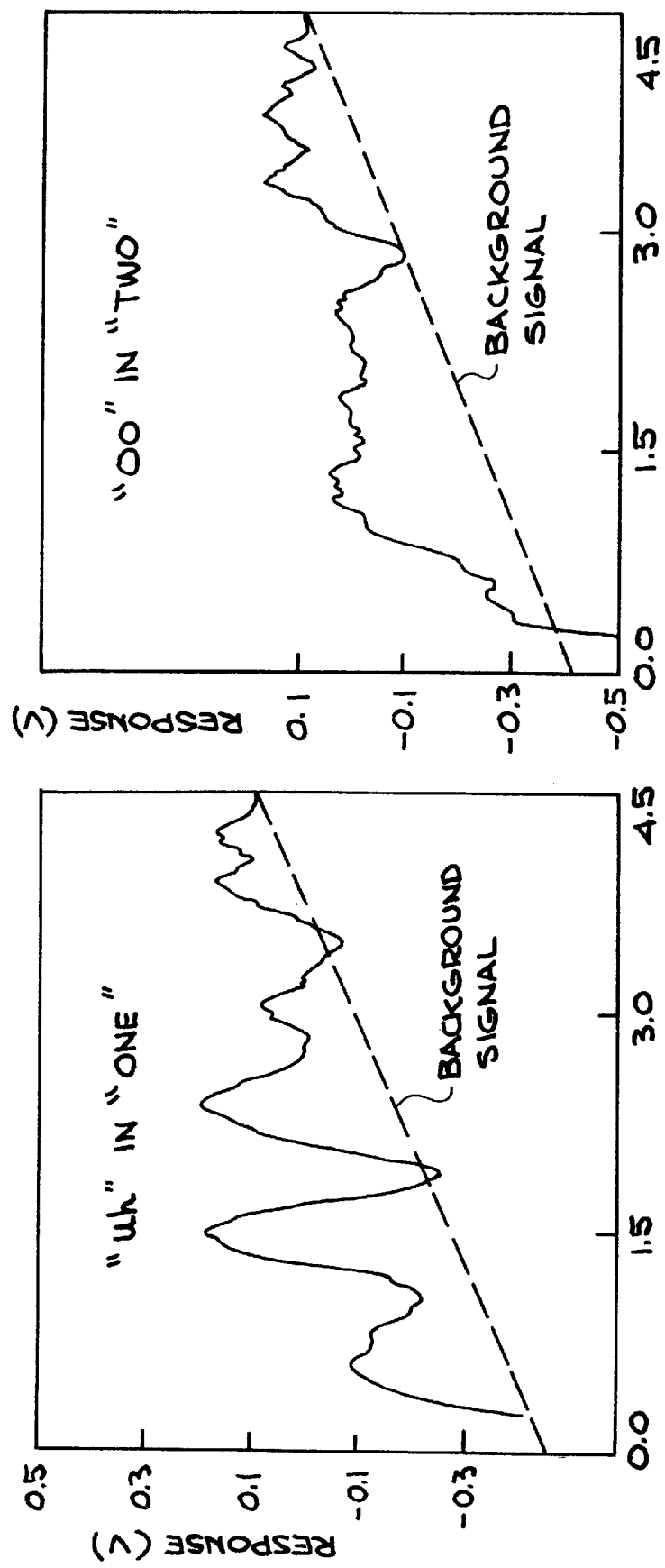
FIGS. 24A,B show an EM sensor (i.e. radar) range sweep of the sounds "uh" and "oo" by a sensor looking up from under the chin.

FIGS. 10A–C illustrate the operation of a short transmit pulse and scanned range gate system as a function of time through the PLU sequence of /silence/, /t/ and /o/. FIG. 11A shows the one half wave transmit pulse. FIG. 11B shows all the received pulses from the single transmitted pulse of FIG. 11A which reflects off all the interfaces it passes through in the path of the pulse. FIG. 11C shows the range gate pulse which directs the received pulse sample through a switch into a bin. The range gate is set for the round-trip time to a particular interface, e.g., lips. Thus only the reflection from the lips is sampled, in the fixed range gate example. However, in a swept range gate system, the range gate is successively "swept through" the whole range, measuring reflections from each position. The result is the digitized, cumulatively received pulses (about 50 to 100) added into each bin at a fixed time in the range gate as shown in FIG. 11D. The gate is then increased by one time unit and 50 to 100 more pulses are directed into the next bin. (An experiment of this nature is shown in FIGS. 24A and C.)

In a modified EM sensing mode, called whole organ sensing, the gate in FIG. 11C is widened from 0.1 ns to 5 to 10 ns and all the reflected signals from all the organs in the propagation path are received and the signal is stored. This is repeated many times to obtain a suitable signal to noise ratio. Then at a suitable time later, e.g., 1 ms, the process is repeated again, but the averaged data is stored in the next bin (e.g., bin 2), etc. until a profile of the complete organ system condition versus time is built up. There is a very large static, average background that is usually subtracted away. When this background is subtracted away, the differences in signal versus time bin can be amplified and processed using real time operations such as time filtering. Such a software embodiment of field disturbance is especially valuable for rapid motions where the background signals remain relatively constant, allowing the algorithm to remove slow body motions from rapid vocal articulator motions. Examples are measuring rapid tongue tip motions or vocal fold motions.

For simple or low cost speech recognition enhancement, one or two organ interface measurements may suffice. For increasingly accurate speech recognition, the user will measure the locations and velocities of many speech organ interfaces, will measure them with increasing locational accuracy, will measure them at multiple locations on a given organ (e.g., tongue tip and back), and will measure them using higher sampling rates in order to obtain the benefits of averaging and also to measure positions vs. time in smaller distance motion increments. In addition the user will measure patterns of organ conditions over several sound change periods to obtain multi-phone and multi-PLU information patterns.

The absolute location of the desired speech organ interface with respect to the head, the jaw, and other organs can be determined, even if the head, jaw, etc. are moving, e.g. by attaching the EM sensor module(s) to the head or neck so head or jaw motion is canceled out. An additional approach is to use the scanning property of the range gate to detect a known reference location, such as the lower jaw skin-to-air interface or the location of the front lip-to-air interface. In this fashion, all other interface locations can be referenced to this "first" interface, and the absolute distances can be easily extracted knowing the relative time of flights. An example of an experiment that illustrates how the range gated EM sensor speech information would be used to define speech phonemes is given by Papcun ibid, p. 697, FIG. 9. He used x-ray microbeams to determine the positions of gold balls glued to the tongue and lips. The position versus time data allowed him to determine those organ articulations (tongue and lip motions) of the pairs of English consonant phonemes /b/&/p/, /t/&/d/, and /k/&/g/. This position information, together with the simultaneously measured acoustic information, allowed him to uniquely identify the consonants being spoken by the speaker. This use of organ positions to identify acoustic speech units is consistent with the vocal organ location vs. sonogram data categorized and explained in Olive et al. "Acoustics of American English Speech" Springer, 1993. Thus, EM sensor measurements of organ location and motion provide the information required for accurate speech recognition.

The measuring of organ interface position for two separate times gives a velocity, and is obtained by dividing the position change by the time interval between two measurements. Organ velocity information can be especially useful for determining the presence of PLUs which are very fast such as "plosives", or those that are not completely articulated or which are coarticulated. The velocity information is especially valuable for rapidly, but incompletely articulated diphones and triphones. An example is the use of an EM sensor to describe the rapidly, and often incompletely articulated /n/ in the triphone /ana/ (shown in FIG. 6).

The measuring of velocity of an organ interface over two separate times provides organ interface acceleration information. This is valuable for use in defining the mechanical parameters needed for speech organ trajectory models based upon, or constrained by organ motions.

Homodyne Mode of EM Sensor Operation

The homodyne mode of EM sensor detection (e.g., coherent radar mode) can also be used to obtain the velocity of the referenced speech organ interface. If needed, by integration over time, one can obtain the change in position within each measurement interval from the velocity information. Velocity and movement information can be used for the resolution of the "run-together", "incomplete articulation", and the "variability of speaker" problem, as well as simplifying other speech recognition problems, because the beginning of "gestures", not their completion, provides much of the needed information. In the simplest version of the homodyne mode, a short pulse (one wave) is transmitted toward the speech organs, i.e., toward the mouth, throat, etc. Using a 2 GHz EM wave transmitter, the EM wave length is 15 cm in air and, consequently, the module would most likely be located a fraction of a wave distance from the head, throat, or upper chest (although other distances from 0 waves to several waves are possible). Once the wave enters the organ tissue (such as the jaw skin, jaw bone, and tongue muscle) the EM wavelength shortens by about a factor of 8 (the square root of the dielectric constant) to a wavelength in tissue of about 2 cm. For example, between the transmitter and the tongue-air interface there may be one or two wavelengths in air plus one to three additional wavelengths in tissue. Upon reflection from an interface, a similar wave path of two to four wavelengths back to the radar antenna is traversed. Upon entering the antenna and the receiver part of the module, the receiver detector compares the wave height of the returning reflected wave to an internal reference wave height. This procedure measures the coherent interference between the returned wave and an internal wave of the same frequency which is frequency stabilized (for only a few waves) to the initial transmitted wave.

As the organ interface causing the reflection moves during speech articulation, the reflected wave will have a longer or shorter path length compared to the path which was used for the initial observation. As an organ moves to a new location, during the articulation of a word, the reflected (return) wave will be added to the reference wave in the module with a different phase. A different voltage will be observed out of the voltage summer in the transmit-receive module, and, by calibrating the phase change with distance, one can find the distance moved from one transmit-receive cycle to the next and thus obtain the velocity. As this send-and-compare homodyne process continues with a fixed time between each send and compare, the phase change will continue to be measured as the interface moves and the velocity will be obtained.

In near field and mixed modes of EM sensor operation, an EM wave can be generated using technology much like that described above for the experimental versions of the impulse radar, and the wave(s) propagate down a transmission line to the antenna structure. The EM wave does not radiate from the antenna structure; however, phase changes associated with organ motions nearby the antenna (within about one wavelength) will change the phase and amplitude of reflected near field waves.

The homodyne technique can be modified for various measurement conditions for speech recognition and related technologies, by using one or more of the following techniques, together or separately:

(1) One wave in the transmitted beam but more than one wave cycle in the received range gate which allows reception of a continuum of reflections from as many interfaces as desired as the outgoing wave passes through the head or upper body. Thus as time passes in the receiver channel, one sees the EM wave reflections from all interfaces in the range gate window which provides a signature of the position of many organs in a time stream of information from the receiver.

(2) A scanning range gate, with fixed width $\Delta t$, but variable range gate delay from transmit pulse to transmit pulse. This obtains information from multiple moving (or stationary) interfaces located at different distances from the module and presents them as received signals (or absence of signal) after each transmit pulse. In this way, the signal from each cycle can be stored in a sequential memory location by the controller; thus, the algorithm can construct a pattern of interface reflection intensities versus delay time. This approach is applicable to radiated and non-radiating systems.

(3) By transmitting a relatively long EM wave (many cycles) that scatters off one or off several interfaces. This implementation is easy to use because the wave train is so long that one or more of the cycles in the pulse train are always reflecting off one of the many interfaces in the head. It can be made easy to interpret by using a fixed range gate which records only the reflection from one of the waves (of the many waves in the single transmit cycle) which is received in the range gate timing window and is measured by the "homodyne" technique. This configuration can provide a unique reflection signature as time passes and as subsequent trains of pulses are transmitted. No matter how the organ interfaces move, there is always a wave being reflected at a time which will be received through the fixed range gate. These scattered waves make a pattern associated with a unique combination of several vocal organ interface motions that evolve in time and the time patterns can be associated with a unique identification of a given sound, word, or phrase. This multiwave EM sensor configuration can also be modified by adding moving range gates, variable range gate widths, and variable frequencies. These approaches are applicable to radiated and non-radiating systems.

Signal Processing

Figure 12:
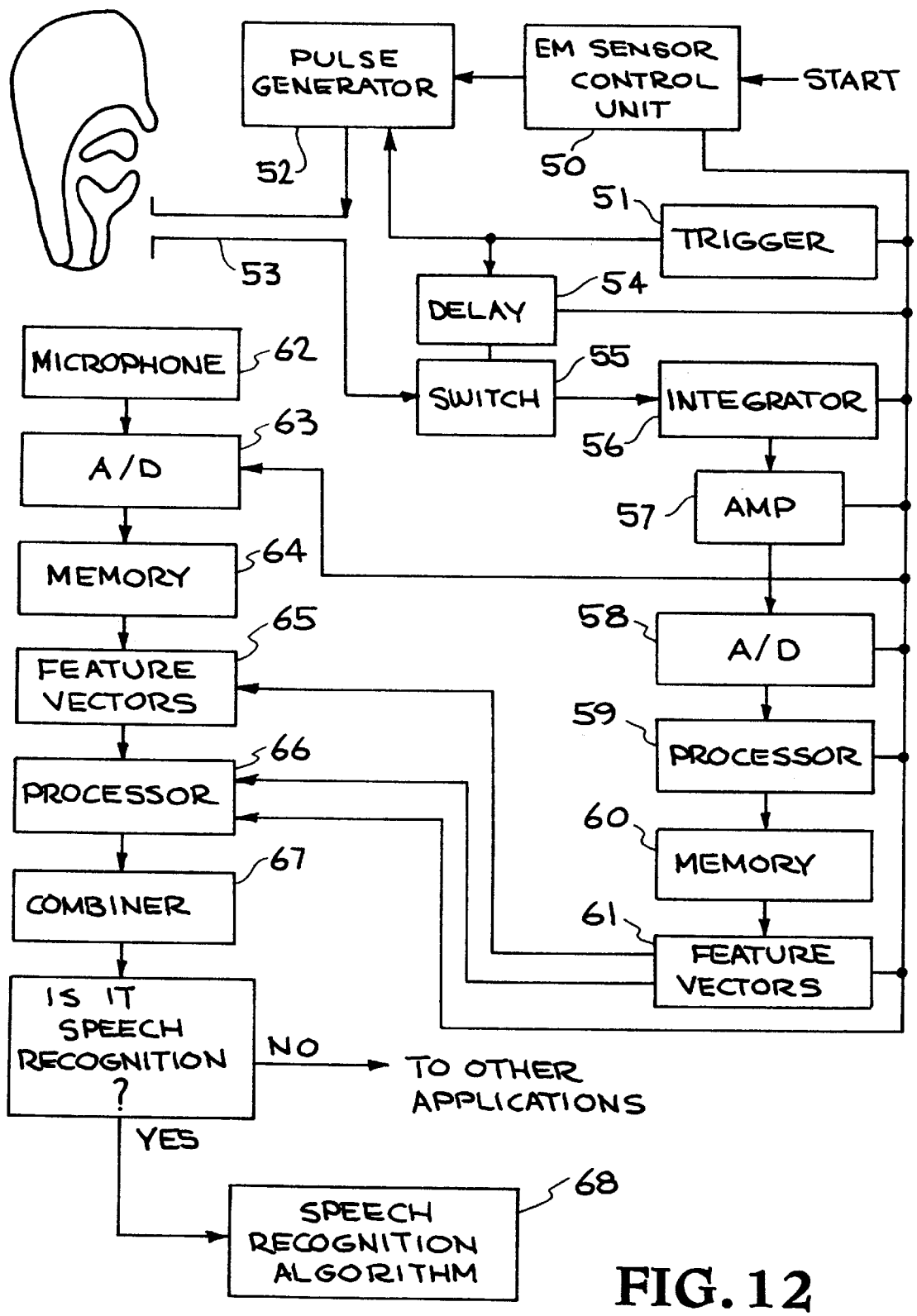
FIG. 12 is a flow chart of joint EM-sensor (e.g., field disturbance mode) glottal tissue (e.g., vocal fold) detection with acoustic-sensor signal detection including preliminary processing, feature vector formation, and a joint decision making algorithm.

As shown in FIG. 12 EM sensor control unit 50 drives a repetition rate trigger 51 which drives pulse generator 52 which transmits one or more pulses from antenna 53. Control unit 50 and trigger 51 also actuate switch 55 through delay 54 to range gate the received pulses. The received pulses from antenna 53 pass through switch 55 and are integrated by integrator 56, then amplified by amplifier 57, and passed through AD converter 58 and processor 59. Processor 59 can include gain setting, speaker normalization, time adjustment, background removal, comparison to data from previous frames, and other well know procedures. The digitized and processed data is stored in memory bins 60 from which feature vectors 61 are formed. Simultaneously, signals from microphone 62 are digitized by AD converter 63 and the digitized data is processed, formed into feature vectors, start of speech is noted as applicable, and the information is stored in memory bins 64 from which feature vectors 65 are formed. The two feature vectors 61, 65 are further processed and combined in steps 66, 67 and if the result is speech recognition, a speech recognition algorithm 68 is applied.

Figure 13:
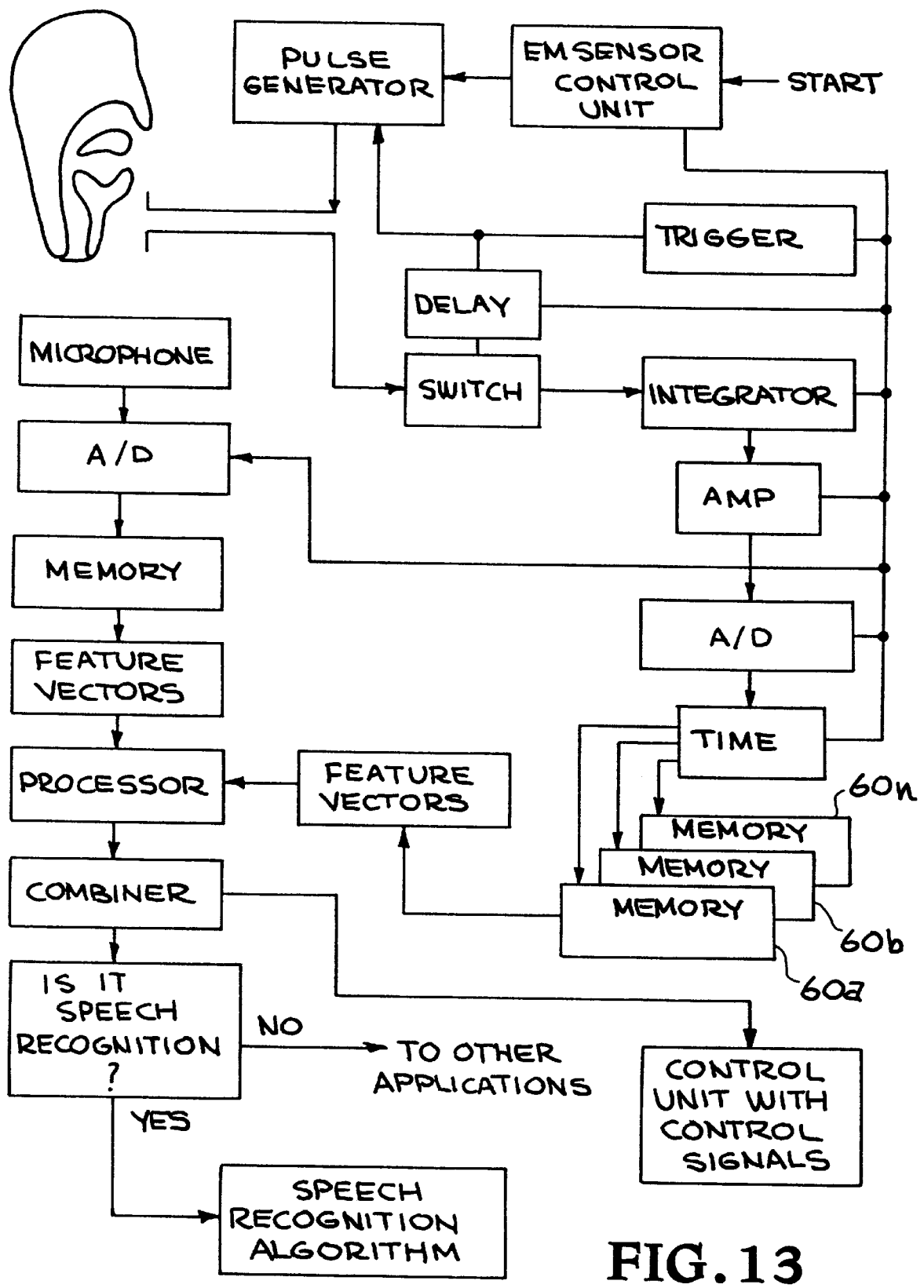
FIG. 13 is a flow chart of joint EM-sensor (e.g., scanned range gate) detection of many organs in horizontal view with acoustic-sensor signal detection including preliminary processing, feature vector formation, and joint decision making.

A similar processing system is shown in FIG. 13 except that it is for multi-location vocal organ signatures. Each single horizontal bin of the nonacoustic patterns describe a single organ location, and the value in that same bin changes as time progresses, the organs move and new patterns are formed as shown. Such a single organ location bin evolves in time, as shown in FIG. 12, as the EM sensor graph 60 and feature vector 61 of a single organ. The system in FIG. 13 is essentially the same as shown in FIG. 12 through A/D converters 58, 63. However, in FIG. 13 a plurality (n) of memory bins 60a, 60b, . . . 60n are illustrated being produced by sequentially range gating to measure different organs or different organ parts. Data in memory bins 60a, 60b, . . . 60n are used to generate feature vectors. The rest of the processing is as in FIG. 12.

Joining of Nonacoustic Sensor and Conventional Acoustic Information

Figure 14:
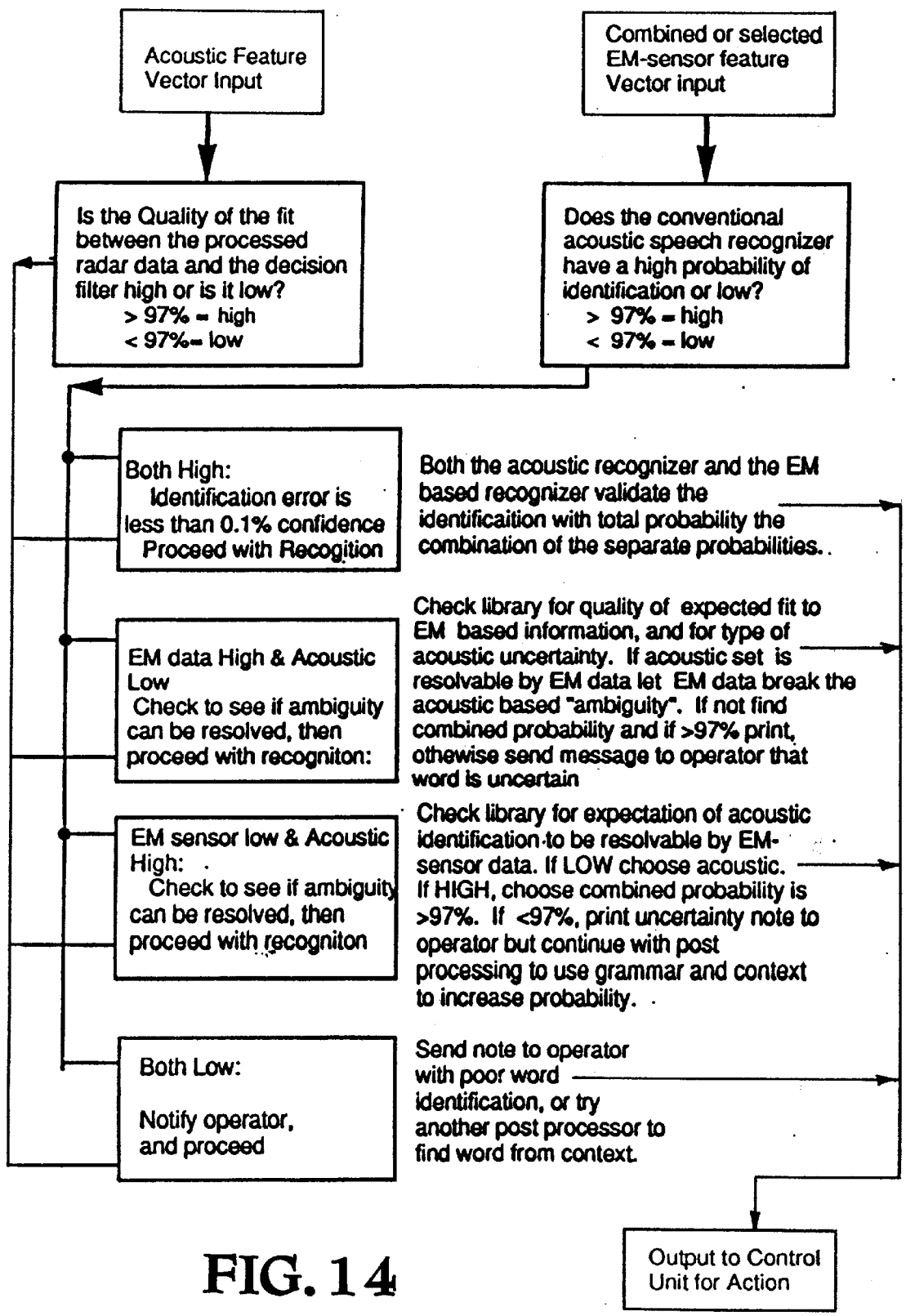
FIG. 14 shows an algorithmic decision tree joining NASR and CASR algorithms with example logical-decision values.

FIG. 14 shows an algorithmic decision tree joining one nonacoustic speech recognition (NASR) algorithm and one conventional acoustic speech recognition (CASR) algorithm. This algorithm is represented by box 67, FIG. 12 and FIG. 13. This decision tree is easily extendible to multiple NASRs if several EM sensors are used as shown in FIG. 13. The test values and resultant values of the algorithmic procedures are determined by the application and the statistical methods used.

Experimental Verification-Preferred Embodiment

FIGS. 15A–D, show the acoustic and EM sensor measured motion of vocal folds for the PLU /ah/. The data was taken using a variation of the range gated EM sensor system but with a fixed range gate. The Fourier transform of the EM signal, FIG. 15D, clearly illustrates the fundamental vocalized excitation function pitch of the speaker at 120 Hz. In this case the EM wave generator transmitted multiple waves (about 10) and the parts of these waves which reflect off the vocal folds at the time the range gate is opened, enter the EM sensor receiver and were detected and stored. The advantage of this sensor configuration is since there are so many waves, one wave is always reflecting off an organ interface at a range gate time that allows detection, thus simplifying the finding of the speech organ interfaces. This simple experiment also indicates how easily this speech organ location information can be correlated with simultaneous acoustic word signals from a microphone. The acoustic signals from a microphone sensing the same words as the EM sensor(s) were displayed on a separate trace of the oscilloscope and were sampled in an A/D converter and were stored in a memory with identical start times and with identical time bin numbers as the memory bins for the EM sensor data. The correlation between these two (or more) signals were used to validate the assignment of irreducible spoken sound units (i.e. PLUs) with the expected location or activity of the vocal organ being measured. In this example in FIG. 15B the glottal tissue motions associated with vocal fold on-off cycling, or the "voiced" activity is shown.

Figure 16:
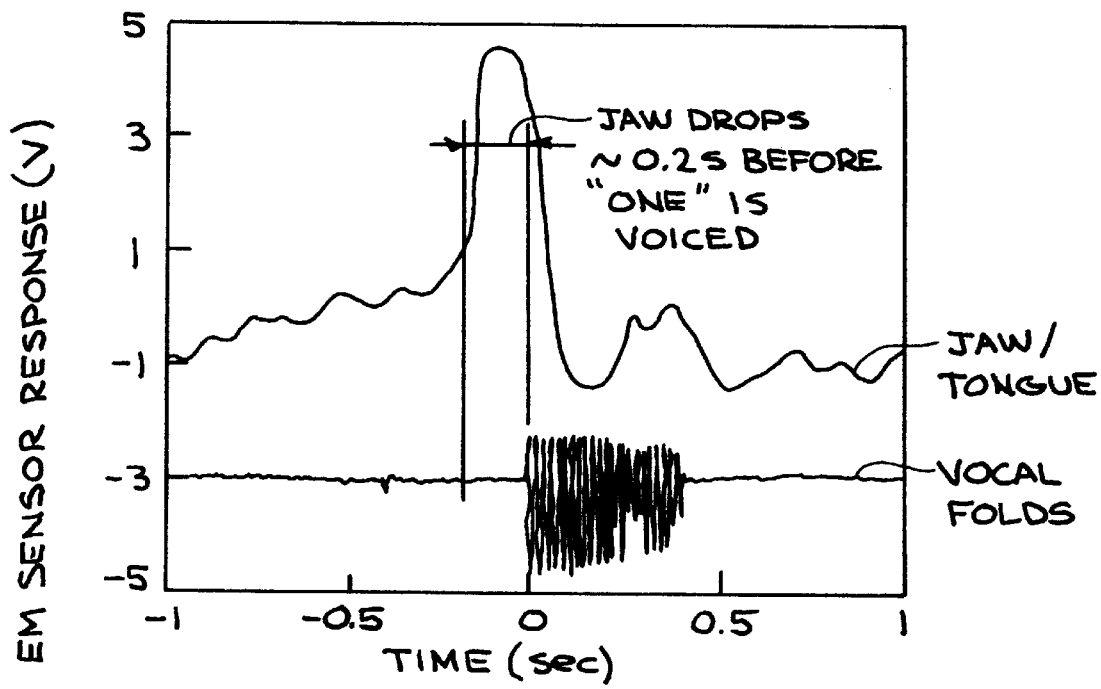
FIG. 16 shows tongue/jaw motion together with vocal fold motions for "one".

Measurements of other organs, such as the tongue and the lips, have been equally easily obtained because they move more slowly than the vocal folds and are larger so they reflect more EM wave energy back to the receiver. FIG. 16 shows the jaw/tongue and glottal tissue responses of radar modules to the word "one" having several phonemes. In particular one sees the jaw opening in preparation for voicing the diphthong /o$^w$/. The glottal tissue trace also shows a glottal tightening signal preceding vocalization, and then it shows the onset of vocalization as the dipthong is vocalized, well after the jaw/tongue motion has begun. This pattern of jaw opening is a triphone of /silence/ /o$^w$/, then the tongue lifts for /n/, then the tongue drops as the final /ae/ is sounded. These simple EM sensor produced NASR patterns are very constraining on the type of acoustic units that were used, and thus must be compatible with units simultaneously recognized by a CASR. This NASR describes the onset of speech, the opening of the jaw, the motion of a voiced diphthong, the voiced high tongue position, a tongue drop, and silence—an end of vocalization and organ motion.

The capacity to detect rapid and incomplete articulator motion can be very useful for distinguishing acoustically difficult phrase combinations such as "ana". When spoken rapidly, a speech sonogram of "ana" (see Olive ibid, p.337) often does not show the /n/, which is an example of incomplete articulation. Thus a CASR that makes a recognition decision based upon the acoustic information, will miss the /n/. However the NASR measurement will show rapid tongue motion (called a "gesture" in the speech literature) which is associated with a weak /n/ sound. It is easily detected by the motion detector system, illustrated as unit 22 in FIG. 4, whose data output in a multiple transmitted cycle, fixed range gate mode, with time filtering to remove slow motions and very fast motions is shown in FIG. 6. The algorithm will insist that an /n/ be placed between the two /a/'s in order to provide the best recognition estimate.

Algorithms

Conventional acoustic speech recognition systems (CASRs) have several major problems which lead to their nominal 2% error rates in quiet laboratory environments, and error rates which exceed 10% when used in noisy environments, on large vocabularies, by stressed speakers, or when used by dialectal speakers. These error rates are too high for most applications. What is needed is a simple, economical sensor device with a stable algorithm that provides sufficient information to reduce the error rates to below the nominal 2% error rates of the best present systems.

All of the algorithms described herein use the property of obtaining speech organ position or motion information through generating, transmitting and detecting EM waves reflected and attenuated from the speech organs. The basic ideas of these new ways of processing the EM information are usually (but not always) used in conjunction with simultaneous acoustic information, and are described as algorithmic procedures. Modifications and variations of these algorithmic building blocks can be used for a variety of applications.

Single organ methods are described first because they make up the basic units of multi-organ and multi-time algorithms. They are characterized by feature vectors describing the state of the vocal excitation function and vocal tract that are essentially constant over a defined time interval called a speech time frame. This new capacity to define constancy of condition makes is possible to compare the measured feature vectors from each time frame with ones previously stored in code books. This constancy also solves the time alignment problem that is so difficult in acoustic recognition algorithms because the vocal tract is time independent over the speech time frame. Additional methods of normalizing the measured vocal tract organ coefficients that make up the feature vector to those that would have been spoken by an average speaker over such a time frame are also described. In addition, a method to limit the number of values of the coefficients of such an organ feature can assume is described.

Such single organ feature vectors can then be combined with feature vectors from other organs taken over the same time period, or time frame to make multi-organ, single time frame feature vectors. Such multi-organ feature vectors, normalized and quantized by algorithms described below make possible either complete nonacoustic recognition (no acoustics needed) or very accurate joint nonacoustic/acoustic recognition systems for very high accuracy applications.

Single Organ Algorithms

The actions of single speech organs, such as vocal folds, can guide important decisions made by traditional acoustic speech recognition systems; however it is not normally possible to use the non-acoustic (radar) signature from a single speech organ motion to uniquely identify a word-sound. Thus single organ algorithms are used primarily in the joint speech recognition mode (where EM sensor plus acoustic sensor data and algorithms are used together). This additional information aids CASR algorithms to provide more accurate, faster, and more economical overall speech recognition. FIG. 12 shows how feature vectors are formed for both an acoustic signal and an EM sensor signal of the single organ vocal fold positions versus time and how they can be joined together for speech recognition and other purposes.

Also included in single organ motion algorithms, are methods using the time evolution of organ motion to determine the condition of various parts of a single organ. Time differentiation of organ position signals gives varying velocities associated with known organ motions (e.g. the tongue tip moves at rates faster than the tongue body). Another method is to obtain several measurements of single organ-part locations from the several interfaces of a single organ (e.g. tongue tip vs tongue back). Another single organ algorithm relies on using one or more wavelengths to detect one or more resonance reflection effects associated with organ shape or air tract-organ shape dimensions. An example is the tongue-palate dimensional opening which changes as sounds are formed.

Single Organ Normalization

The feature vectors associated with an individual's speech can be "normalized" and then mapped uniquely to a feature vector of a referenced individual or to a group of individuals (e.g. to an average speaker of the language). This method includes training an algorithm by asking a speaker to pronounce a known set of words chosen to determine the reflection signal amplitudes, the position limits, the velocity limits, and the time periods of as many of the individual's vocal articulators as needed for the given EM sensor suite for the application. Then an algorithm makes a one to one assignment from the EM sensor signal associated with each articulator position during the speech frame measurement, to the signal measured by the same type of EM sensor, but obtained earlier from the referenced speaker(s) as they spoke the same word set by using simple interpolation between the measured data. In this way a person with a small tongue that reflects less EM wave energy and that does not move as far, is normalized to an average individual who has a larger tongue and more extensive tongue motion.

Using this knowledge of organ range, and the phonetic knowledge that an organ must move a given fraction of its range to establish a detectable new sound, one can quantize organ motions by the fraction of total allowable change measured during the speech frame. In other words, there are bands of organ position over which no discernible speech sound change occurs. Thus the feature vector coefficients can be quantized, and a given organ feature vector coefficient may be described by only a few fractional values, such as the following five, 0.0, 0.25, 0.5, 0.75, and 1.0. These numbers can by multiplied by a normalized amplitude value if desired.

As an illustrative example, consider the tongue body (i.e., blade) positions which could be described by a normalized and quantized feature vector coefficient of 0.25. This value of 0.25 means that the tongue is in the second of five possible positional "bands" that describe the range of its motion as detected by the EM sensor system in use. This value would describe the tongue position until in a subsequent speech time frame, the tongue would have moved sufficiently to be detected as lying in a new "band" of the allowed positional range (and a new discernible sound might be caused by the new tongue position). The feature vector coefficient in this new speech frame, would be normalized to a new value and then quantized to a new number, e.g., 0.5, representing in this example a tongue blade in the midway position between far up and far down.

This algorithm can be extended to normalize a speaker's speech organ rate of motion velocity in several ways. One important time normalization is described below under speech period definition and pitch period normalization. A second important time normalization is to normalize the rate of change of a feature vector coefficient over one or more speech time frames. The algorithmic procedure is straightforward; one subtracts the normalized coefficient or coefficients of the desired organ locations obtained during the most recently processed speech frame from those obtained in the second most recently processed feature vector. One divides this normalized position change value by the time elapsed between the two feature vector measurements. For example, subtracting the start time of the second most recent frame from the start time of the most recently formed frame gives an elapsed time. The vector times can be used as measured, they can be normalized using well known time warping techniques from acoustic speech, or they can be normalized times for the sounds as spoken by a reference speaker and obtained via a recognition process, One can also define characteristic motion times differently; for example each organ has measured characteristic rates, and the algorithm simply divides the location coefficient difference by a previously defined time constant to obtain a characteristic motion time. Each organ can be normalized according to its known responses which are obtained from research, from training on the individual or on a referenced person or group, from mechanical models, or adaptively during the speech recognition process. Furthermore, during training, the characteristic organ motion times of the user can be associated, on a one to one basis, with the characteristic organ motion times of referenced speakers. These velocity values can then be quantized as described above for position values. An example of extreme quantization of organ motion is to form two velocity bands—slow or fast (e.g., 0.0 or 1.0). This simple quantization process, see Table III, constrains the phonetic identification of the PLU or other acoustic unit very strongly.

Using the algorithmic procedures described above, one can use one or more of the following four operations: 1) normalize an individual speaker's feature vectors to those of an average population; 2) detect the degree of incomplete articulation and coarticulation; 3) pre-normalize an individual's articulation habits; and 4) limit the number of values used to describe the condition of his speech organs. In addition, as each day starts or during the day, using adaptive techniques, the system can renormalize the speaker's use of time as he speaks to the referenced conditions obtained earlier.

The methods of using nonacoustic together with acoustic information to form speaker independent (i.e., normalized) descriptions of feature vectors make possible, for the first time (using nonobtrusive, real time means) obtaining very rapid, and very accurate identification of the obtained feature vector against libraries of preformed feature vectors that are associated with known speech units such as syllables, phonemes, PLUs, acoustic units, words, and phrases.

Single Organ Contact and Resonance Algorithms

Figure 17:
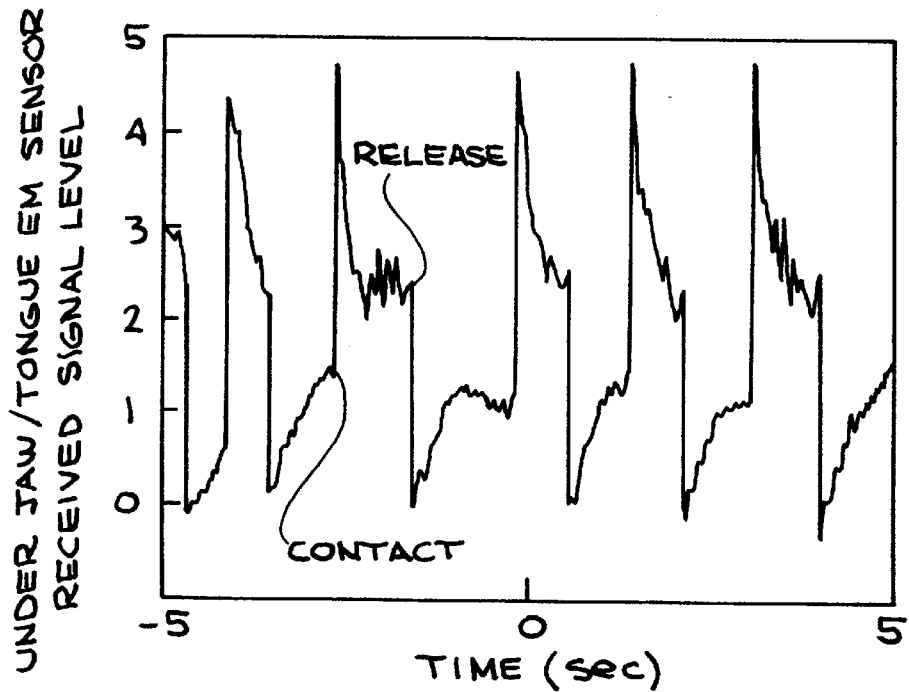
FIG. 17 shows experimental data for tongue palate "contact" detection taken using a field disturbance mode EM sensor under the jaw detecting the strong change in reflectivity of the tongue palate system when contact is made.
Figure 18:
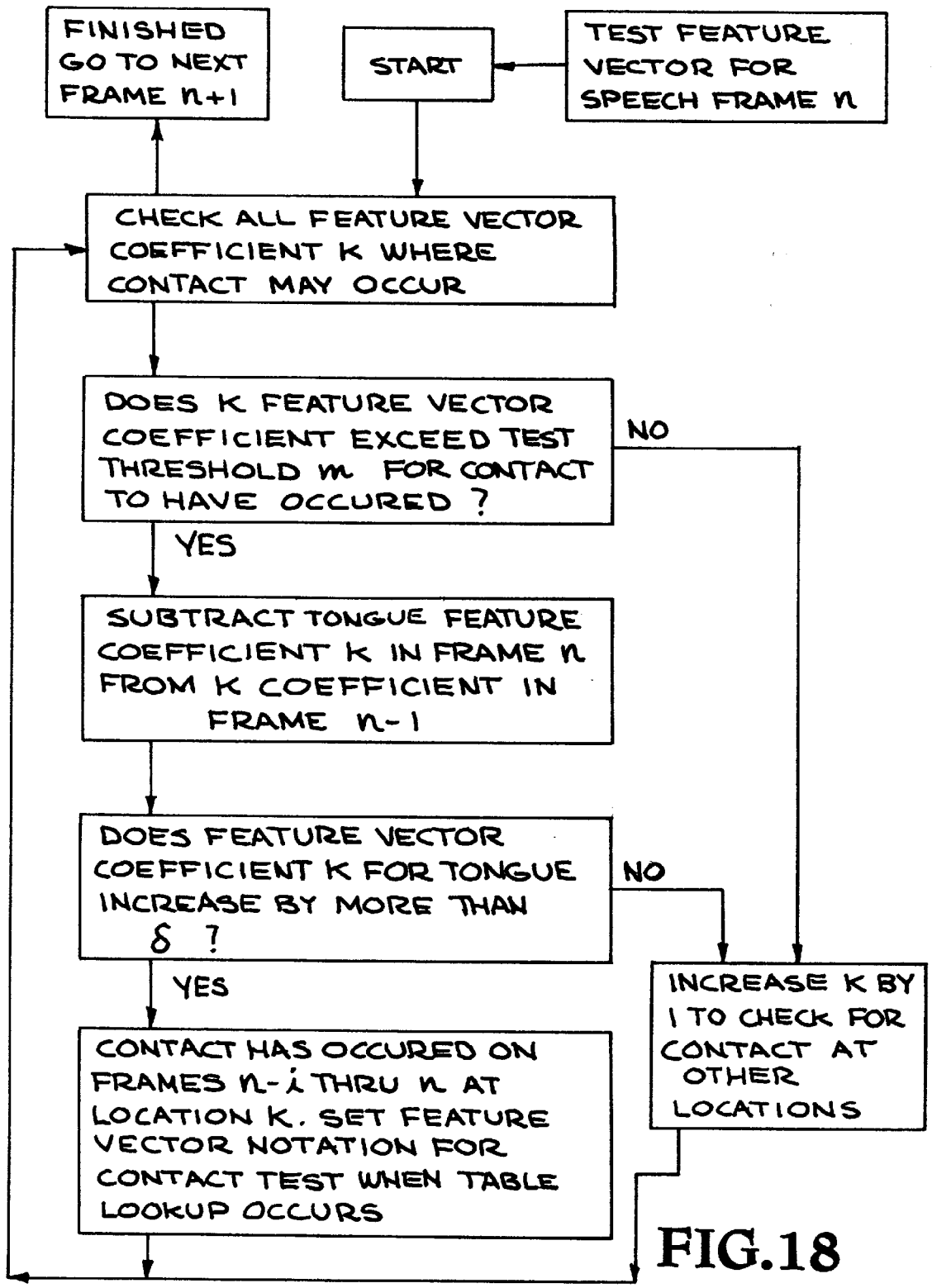
FIG. 18 is a flow chart of an algorithm for detecting and storing tongue palate contact information in a feature vector for the speech frame in which contact occurred.

A specific and important single organ algorithm is the contact of one organ against another. In speech, the presence, the location, and the rate of tongue contact against the palate shows that a "t" or "d" or similarly determined sounds are being formed by the tongue. The tongue tip to palate contact resonance has been measured and a five fold increase in reflectivity is obtained from the contact. FIG. 17 shows tongue contact data, and FIG. 18 provides an algorithmic description. Organ contact detection is a very important indicator of certain speech sound units being articulated. The use of resonances and changes in resonances from one speech frame to another provides clear evidence of such conditions. The contact of one organ against the other changes the EM standing wave structure and organ interface EM boundary conditions, and results in a large change in reflectivity. The use of range gating, time filtering, and other locating techniques allows one to locate the points of contact if desired. Thus the contact intensity, change from frame to frame, and location can be recorded, normalized, and stored in a feature vector for subsequent pattern matching, code book comparison, and other statistical techniques described below.

A strong resonance condition can be detected when the dimensions of two or more organ interfaces are resonant with a particular wavelength of the propagating EM wave from an EM sensor. When an EM wave of appropriate wavelength reflects from one interface, it can add coherently to an EM wave reflecting from another interface. The case of total constructive interference occurs when the distances between the interfaces are multiples of ¼ wavelength apart in the medium of transmission (for example, about 4 cm for 2 GHz in air or about 0.5 cm in tissue) depending upon how the interface changes the wave phase upon reflection. A very large reflection occurs because the signal intensity is the square of the sums of the wave amplitudes at the detector, or it is 4× that of single interface reflection. Similarly, reduced reflection can occur when reflected wave amplitudes destructively interfere. These conditions occur when there is a ½ wave distance between interfaces, and the detected reflection is canceled (or reduced if the phase is not perfectly destructively phased). A consequence of reduction in reflection is that a stronger, forward propagating wave beyond the interface takes place, as in anti-reflection coatings on camera lenses. In the case of tissue, the index of refraction is so large, typically 5 to 9 (in contrast to air with an index of essentially 1.0 that very large coherent effects can take place. To detect these effects, a swept frequency EM generator and complementary detector can be used to "measure" the distances of important interfaces for important conditions. The transmitted and received EM wave information, including range gate information if used, is recorded along with simultaneously measured acoustic information.

Single Organ Algorithmic Descriptions

Figure 19:
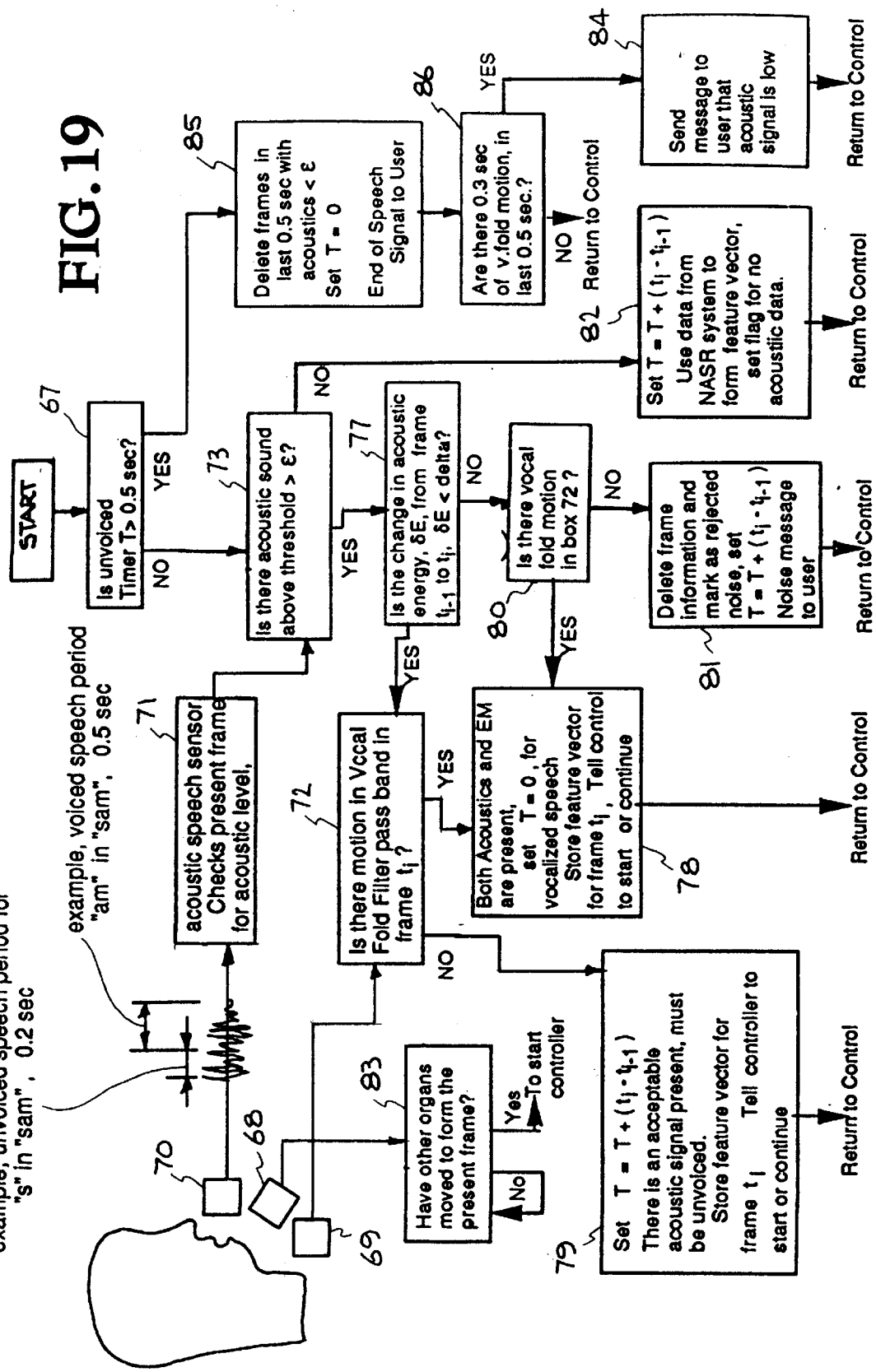
FIG. 19 is a flow chart of an algorithmic procedure for start of speech, end of speech, identification of voiced or unvoiced phoneme, presence of pause, and extraneous noise presence.

FIG. 19 illustrates one method for determining the onset of speech, noise rejection, voiced-unvoiced speech, end of speech, and pauses using acoustic and non-acoustic information together. The example is for American English with the word "sam". The times and other constants are statistical estimates and are to be adjusted for different speakers and languages. These algorithms have been tested manually.

The acoustic information from microphone 70 is inputted into an acoustic speech sensor, A/D converter and 1 sec. memory 71. Vocal fold motion information from EM sensor 69 is input into integrator and band pass filter 72. The processors make decisions as described below and as listed in Table I. The listed examples are single organ NASR algorithms which can be used as building blocks for more complex speech organ descriptions.

TABLE I

Examples of single organ FM sensor algorithms

| | |
|---|---|
| 1) onset of speech time | 6) average rate of speech |
| 2) end of speech. | 7) difficult sound differentiation |
| 3) background noise rejection | 8) multiple PLU & word coding |
| 4) presence of voiced speech | |
| 5) pitch of speech | |

Onset of Speech Time Algorithm

Onset of speech is important for speech recognition because there are many extraneous noises in a user's environment that can trick a CASR into beginning to process the sounds as if they were speech. The algorithm of FIG. 19 is based upon the statistical occurrence in a language of vocal fold motion onset, and it uses speech time frame definition and feature vector formation. In the case of whispered or nonsounded speech, additional EM sensor information is required for onset definition and is described below. Vocal fold open/close motions occur when voiced sounds are formed, as well as when the folds open for whispering or to allow air flow for unvoiced sounds. Most American English sounds are voiced and almost all words contain one or more voiced sounds within each second of speech. This speech usually contains up to ten PLUs or similar sound units per second and a non-voiced sound is statistically followed by a voiced sound or pause every 1 to 2 non-voiced PLU units. The algorithm detects the onset of speech by using both an acoustic and one or more EM sensor modules at the same time. The issue for this algorithm is that some words begin with unvoiced sounds such as "s" in "sam" or in "sixteen"; thus the algorithm must be able to back up to catch sounds that may be missed by the vocal fold motion onset detection by the EM sensor. In two speech processing systems, shown in FIGS. 12 and 13, the onset algorithm described here would be used primarily in box 66. The unvoiced duration timer T is initialized to zero at system turn-on.

Speech onset testing is begun after acoustic and EM speech time frames and feature vectors are formed. For this example, each speech frame "i" is defined by its end time $t_i$. The algorithm FIG. 19 is entered at box 67 where a test on timer T for the cumulative duration of unvoiced speech over several speech time frames is conducted (e.g., is T >0.5 sec.?). If the duration of testing is shorter than 0.5 sec, then if the acoustic microphone 70 output signal exceeds a preset threshold 73, but when it is less than a loud noise threshold 77, then the algorithm looks for vocal fold motion to occur within the same speech time period in box 79. If acoustics and vocal fold motion are present, then a voiced speech unit has occurred and the unvoiced timer, T, is set to zero in box 78, and processing on frame $t_i$ continues. If satisfactory acoustics, but no vocal fold motion occurs in box 72, the sound in frame ti is labeled as nonvoiced speech in box 79 and processing continues. If the acoustic signal is too loud in box 77, and vocal fold motion is detected at box 80, the signal is processed as loud voiced speech box 78. If acoustic speech is below a threshold box 73 (a test not used for silent or whispered speech applications), the EM sensor feature vector is processed in box 82, the acoustic signal is labeled as too weak in box 82, the non-voiced or silence counter T is increased at box 82 by the time $t_i - t_{i-1}$ of the most recent speech time frame, and the processing continues. If upon entering the algorithm at 67, the test on T shows that 0.5 sec. or longer of unvoiced or silent speech has occurred, the speech frames within the T (e.g.,. 0.5 sec) interval that have acoustic energy coefficients less than E are deleted at box 85, a test is made for low acoustics in the presence of vocal fold motion at box 86. If low sound, but vocal fold motion is occurring, the system sends a low sound message to the operator at box 84, and returns to the control unit awaiting a start condition.

Speech onset, as detected in the master control unit by direct messages from units 78 and 83 in FIG. 19, may be validated by the algorithm starting at box 67 once start has occurred. An important example is that tongue and jaw motion EM sensors as shown in FIG. 4 (modules 21 and/or 22) and in FIG. 19 (modules 68, 83) can measure precursor motions of the tongue and/or jaw motion as they move to a position in preparation for the first sound. FIG. 16 shows an example of speaking the word "one". Tongue and jaw motion are helpful indicators of speech onset, but do not guarantee speech; thus, the algorithm starting at box 67 is necessary to test for speech starting within 0.5 sec of timer T after a start condition is detected from boxes 83, 78, or 79. If after 0.5 sec, no speech is validated, the system is returned to the master control for quiescent operation, or other conditions.

In the cases of onset of whispered or unsounded speech, additional EM sensor information is required. The same single organ arguments used to describe vocal fold motions and the use of the single organ tongue (or tongue-jaw coupled motion) discussed above are used as onset indicators. This includes the vocal folds which open, but do not vibrate open and closed, during whispered and unvoiced speech. The acoustic level sensors, boxes 73 and 77, can be turned off if unsounded speech or machine control communication is being used or set for very low levels when whispering only is desired.

End-of-Speech Algorithm

If the vote from the onset of speech algorithm shows that speech has started, then the algorithm in FIG. 19 continues to test each speech time frame for continuation of speech. The main issue for the algorithm is that in American English, it is common that words end in non-voiced consonants—e.g. plural /s/'s. This algorithm uses a test time 0.5 seconds to limit search after vocalized speech stops. Processor 67 tests if T>0.5 sec., and if true, it directs the operation to processors 85 and 86, where the process is stopped and returned to the controller. If acoustic units 73, 77 show acceptable acoustics, but no vocal fold motion is detected at boxes 72, 79 within 0.5 sec (i.e., T<0.5) after the last voiced speech frame, the counter T is increased by the frame-i time duration and the next speech frame is tested starting at box 67. These tests are for excessive background noise that may "alias" as acoustic speech sound, but the statistics of the language insist that every 0.5 seconds (example only) vocal fold motion must occur. However, every speech frame that is processed within the 0.5 sec waiting period, even without voicing, is processed as a nonvoiced segment and the feature vector is appropriately defined. If after 0.5 sec of processing, no vocal fold motion is detected, the algorithm 67 defines end of speech at boxes 85, 86. The speech frames recorded during the last 0.5 sec are tested for acoustic levels above $\epsilon$, and if not, they are deleted. For very special speech technology applications where many unvoiced sounds are used by a speaker as in storytelling, acting, or simulating machines or animals, the user can change the test periods for T to emphasize the acquisition of unvoiced sounds of varying types and lengths.

Background Noise Suppression Algorithm

There are two issues in background noise suppression: noise that occurs when the speaker is not speaking but which a CASR confuses with speech onset, and noise that occurs during the speaker's ongoing speech period. In the first case, noise occurring while the speaker is not speaking is eliminated as valid speech input by an onset of speech algorithm.

The second case, the elimination of acoustic noise (from background) that enters the microphone during speech, is made possible by the use of non-acoustic data. If a constant high background acoustic level is such that it is comparable to the acoustic input by the speaker into his own microphone, then it is known by experts that CASRs will not work. However, the multi-organ NASR systems will work, because they can provide sufficient information to determine the missing speech unit information, they will continue to function by automatically defining speech time frames, and they will provide best estimates of the speech sounds as if they were operating in a whispering or nonsounded speech mode of operation.

In the case that the exterior acoustic noise is loud, but short in duration, it will appear during one or only a few speech time frames as an unusual acoustic signal in the acoustic output of speech processing algorithm illustrated in FIGS. 12 and 13. The algorithm in FIG. 19 illustrated by boxes 67, 73, 77, 80, 81 detects the unusual noise event, removes the frame information, and marks the frame as "damaged" for subsequent processing. A typical acoustic unit recognition algorithm as illustrated in FIG. 14, will detect the noise and will note that the CASR information is to be disregarded, and only the NASR feature vector coefficients will be used to obtain the best possible acoustic unit identification. As such noise events occur, the user can be notified that the data is being degraded by external noise signals.

In the case that moderate level noise degrades the information reaching the microphone from the speaker, the additional information provided by the NASR system can be used in an algorithm to recover the speakers intent. The user may chose to direct the algorithm in FIG. 14 to 1) pick the best signal from the NASR test when the CASR signal is inconsistent with the NASR data, 2) perform a further test on the continuity of CASR and/or the NASR feature vectors from the preceding speech frame to the following speech frame in order to reject feature vectors that are inconsistent with known feature vector sequences over several speech frames or that don't meet known organ motion constraints. Similarly, if a diphone or triphone library is available, the multi-frame signals from both the CASRs and the NASRs can be compared to the best fit in the library using a process substantially the same as in FIG. 14. If no match, or only a low probability match, is available from the CASR system the speech frame acoustic signal based identification is given a low probability (e.g., it was probably noise degraded), and the algorithm chooses the NASR identification as best according to the rules of the algorithm.

The capacity of the methods described above to notify the speaker that an error or uncertainty has occurred is very valuable, especially in high value speech recognition or similar situations where an error can have serious consequences. This stability is characteristic of "robust" recognition systems.

Algorithm for Identification of Voiced or Unvoiced Speech-PLU

Vocal folds do not open and close in repetitive cycles when nonvoiced sounds are spoken. They do open for whispering or nonvoiced sounds in most circumstances. Examples of 8 voiced and nonvoiced PLU pairs, which are confusing to CASRs, are shown below in Table II (from Olive et al., "Acoustics of American English Speech", ibid p. 24). They are confusing because each pair has the same vocal tract formation, but one is voiced (vocal folds vibrate) and the other is sounded by air rushing through vocal tract constrictions (frication, aspiration, etc.) such as almost closed lips as /s/ is sounded, in contrast to the vocalized version which is /z/.

TABLE II

Voiced and Non Voiced English sound pairs discernible using EM sensors

| voiced | unvoiced | voiced | unvoiced |
|---|---|---|---|
| b | p | v | f |
| d | t | th (as in then) | th (as in thin) |
| g as in g ut | k | z | s |
| j | c (as in chore) | g (as in garage) | sh (as in shore) |

If the CASR algorithm used in conjunction with the NASR decision algorithm (shown in FIG. 14) is applied to this decision, it will yield a signature for an acoustic sound that will be somewhat ambiguous between the voiced or unvoiced version. That is, its probability of certainty of identification will be confined to either one or the other PLU of the pair, but the certainty as to which one will be lower than desired. A voiced-unvoiced algorithm is accomplished two ways. The simplest, used in the sense of a speech recognizer "cue", uses FIG. 19, processor 72. Processor 72 detects vocal fold motions and notes in a control coefficient of the feature vector for the speech frame that this distinction has occurred. The second approach uses the normal algorithmic processing in FIGS. 12 and 13, where the data is measured, averaged, quantized, and processed such that the vocal fold EM sensor data is available for the acoustic sound recognition procedure in FIG. 14. The algorithm in FIG. 14 would proceed as follows to deal with a softly spoken /z/. The acoustic sound feature vector when compared with those in the CASR library will show two PLUs with relatively high probability (e.g., /s/ and /z/), but with a notation that the acoustic signal has a low probability of discrimination with these acoustic units. Next the algorithm tests the output of the NASR system to provide the probability of voiced (e.g., 100%)) or nonvoiced speech (e.g., 0%), and the joint algorithm chooses the voiced version of the PLU being tested in the speech time frame being examined.

Pitch Period and Speech Frame Determination Algorithms

The output from sensor 23 in FIG. 4 provides the fundamental open and close rate of the glottis, as measured by observing the motions of the glottal tissues, especially the vocal folds.

Figure 20A:
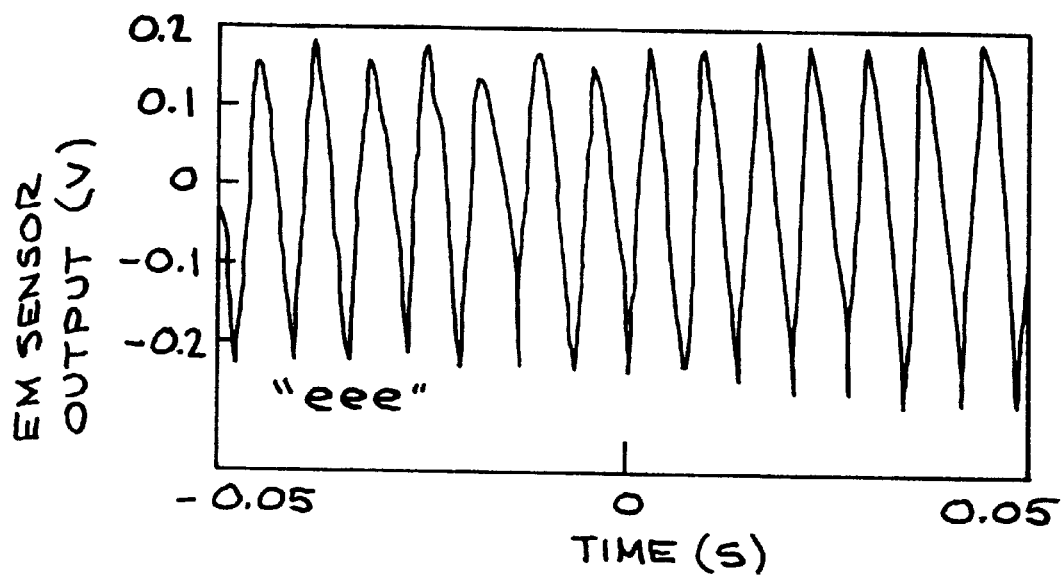
FIGS. 20A,B show experimental data using EM sensor (field disturbance mode) detecting vocal fold waveforms for the letters "e" and "u" showing large differences in pitch rate from the same speaker.
Figure 20B:
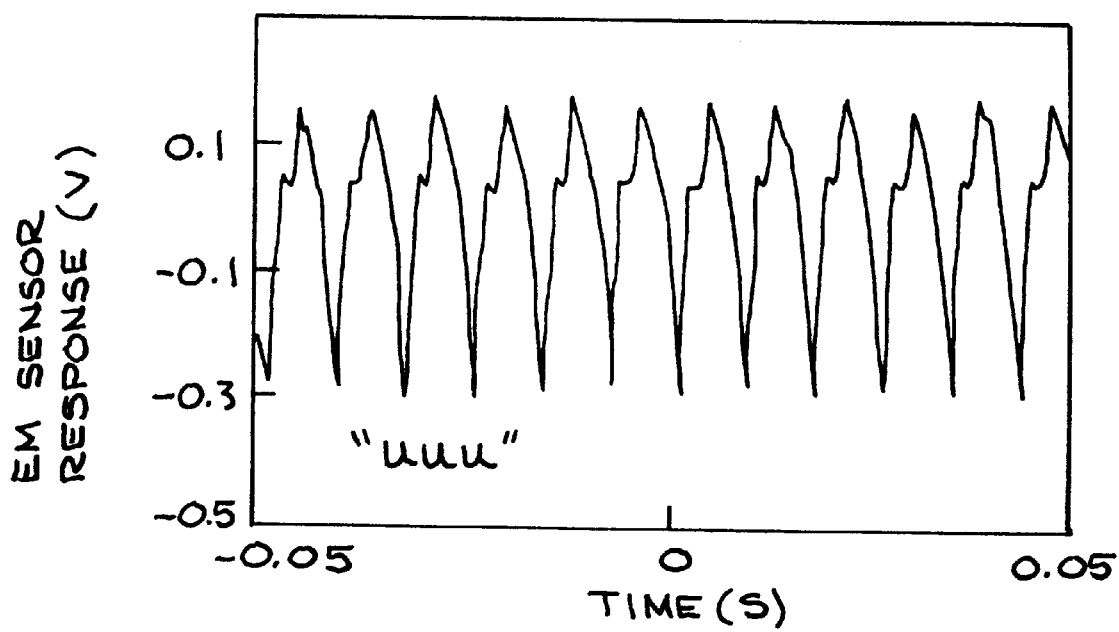

1) Algorithm 1 has been designed and tested to measure the time intervals of the glottal open/close motions as shown in FIGS. 20A,B and to automatically give the instantaneous voiced pitch period of the speaker each speech frame. This algorithm automatically defines the speech frame duration to be the time between zero crossings of the EM sensor data and the peak to peak times of the EM sensor data. The fundamental frequencies of the two data sets shown in FIGS. 20A, B differ by a factor of 20% and they show that "e" is a higher pitched sound with a vocal fold pitch period of 6.25 ms (160 Hz) than "u" with a period of 7.81 ms (128 Hz) by the speaker. The savings in computational time of this algorithm, compared to the normal all acoustic pitch tracking algorithm, is greater than a factor of 5 and is much more accurate.

Figure 15A:
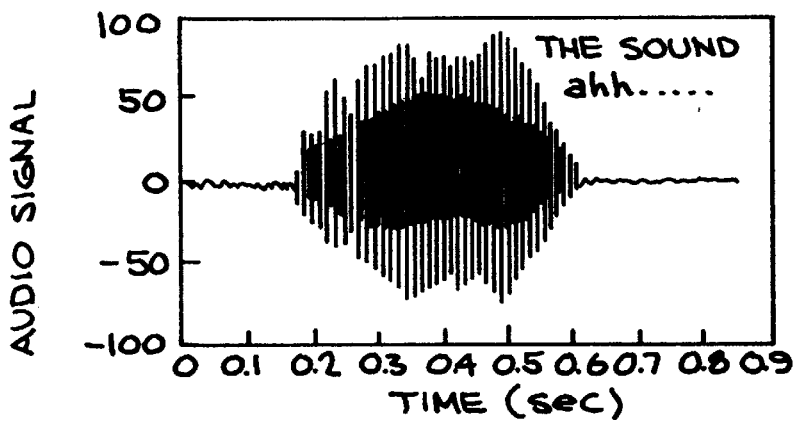
FIGS. 15A–D are the acoustic and EM vocal fold sensor data for the phoneme /ah/ as amplitude vs. time and with the Fourier power spectrum.
Figure 15B:
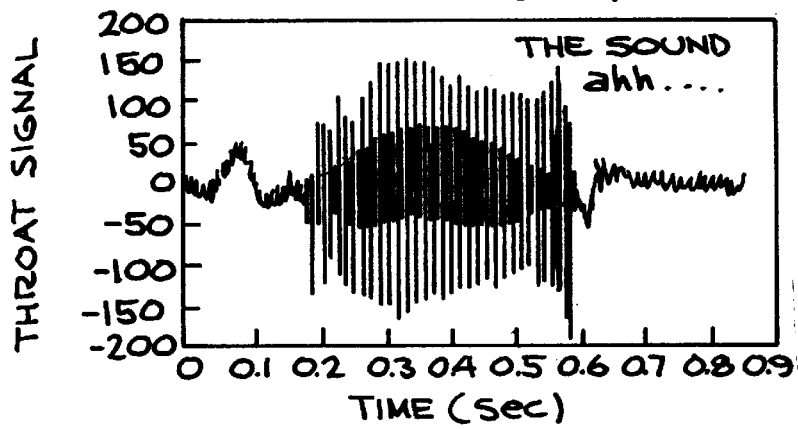
Figure 15C:
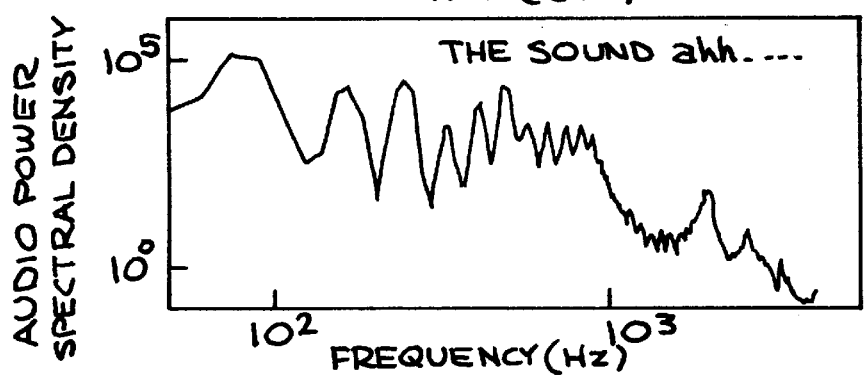
Figure 15D:
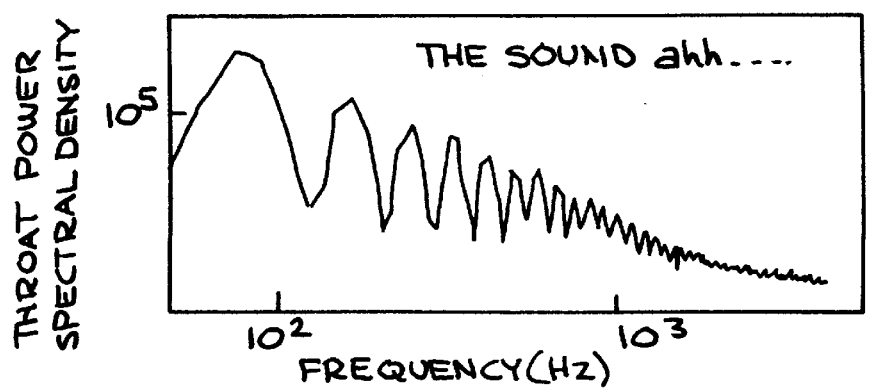

2) Algorithm 2 has been designed and tested to determine if a sequential measured pitch period, when compared to an initial pitch period measurement, has the same pitch period value (within a user defined numerical band of measurement accuracy, e.g. 5%). If so, this algorithm then increases a "counter" by 1 unit as it counts the next period as being identical; it proceeds and counts the number of sequential pitch periods that have the same value. If the next pitch period value is no longer the same, then the algorithm reports that a new initial period has started. See FIG. 9 where speech frames 3 through 15 meet such a criteria. In two experiments, one of which is shown in FIG. 15B, two male speakers spoke the phoneme /ah/, and the algorithm showed one to have a 90 Hz fundamental (11 ms pitch period) and a 120 Hz (8.3 ms pitch period) fundamental excitation frequency, and the pitch change with words was easily tracked for each speech frame.

Such a sequence of identical pitch periods as defined by algorithm 2 can be used in another algorithm to define a multiple pitch speech frame of constant feature vector value when other EM sensors and/or acoustic information are involved. The definition of constant period is extended to constant acoustic signal, or constant tongue position, etc. so that an algorithm can automatically determine the number of voiced pitch period cycles over which constancy of a sounded speech unit takes place.

3) Algorithm 3 uses transform techniques for the pitch period finder and uses data from unit 23 in FIG. 4 which appears like that shown in FIGS. 20A, B. It uses algorithm 2 to define a number of identical speech time frames. The algorithm next filters the data from the series of frames over which the data is constant, with a smoothing function (e.g. Hamming), and it next performs a Fourier transform (or Z-transform) on one or more sets of the time series of data points. The algorithm performs a search on the transformed data set(s) to find the highest amplitude signal and then chooses the frequency associated with the highest amplitude signal to be the fundamental pitch frequency.

Two variations on this algorithm to find the pitch period are: 3a) automatically measure the frequency difference between the first and second harmonic to find the fundamental frequency, and 3b) pick the location of the first peak when searching for peaks starting from zero frequency. These have the advantage of not basing the selection on the highest amplitude, and also provide redundancy in the measurements which can be averaged to find a more accurate value.

4) Non-voiced speech frame duration. In the cases where no glottal repetitive motions occur, i.e., nonvoiced speech or silence is occurring, a default method of defining speech frame duration is required.

4a) The time frame is defined as the time period during which the acoustic output is constant within predetermined bands. If the unvoiced sound changes, then a new speech frame is started and the previous time frame duration is recorded. This algorithm treats silence as no acoustic change.

4b) A default time of 50 ms is used to define the duration of sequential speech time frames.

Pitch Normalization

An algorithm is designed to be trained by a series of words which cause the speaker to speak vowels and consonants which cause the vocal folds to vibrate at the lowest, at an intermediate, and at the highest frequencies for the speech recognition or speech technology application at hand. This training, defines the pitch period range of an individual speaker over the vocabulary training sets of language sounds to be used in the application. Similarly, a single reference speaker or a group of chosen reference speakers would have been asked to speak the same word set in order to define a reference code book of normal pitch periods for known sounds. Then the algorithm makes a one to one correspondence from the user's instantaneous speech period to the pitch period of the reference speaker for the same sound. Then the algorithm maps a speaker's pitch period time to a reference speaker or speakers period every time the period is measured during normal use. This new period is used to define the pitch period of the normalized excitation function in the normalized feature vector.

Use with CASRs: The instantaneous pitch period information as obtained by NASR systems is used by conventional speech recognizers to aid in identifying the phonemes, to train a recognizer to find the natural pitch of the speaker, to normalize the speaker to an average or reference speaker, to determine the excitation function in model based recognition systems, and to assist in determining the speech rate for word alignment (i.e. time warping).

Use in NASRs: The algorithms provide a basis for defining speech time frames, fundamental pitch periods, speaker identification, and basic excitation rates for model based recognition algorithms. Most importantly, they allow the NASR system to remove enough of an individual's idiosyncratic information such as non-average pitch usage, and nonaverage number of pitch periods in acoustic unit articulation from the measured feature vectors. Therefore, these methods allow the acoustic sound unit, e.g. PLU or phoneme, to be defined by the excitation function conditions and the vocal tract conditions, not by timing information that is confusing. When timing information is useful, it can be separated from organ position information and used to best advantage. Straightforward acoustic unit identification follows.

Rate of Speech Algorithm

The rate of speech is important for conventional acoustic speech recognizers and nonacoustic recognition systems because they use time intervals derived from time rate of acoustic information flow to identify phonemes and to align speech segments for speaker normalization. The CASRs use a technique called time warping to align the rates of segments of spoken speech so they can all be recognized with the same recognizers no matter how rapidly or slowly they were spoken. The NASR algorithms use speech period length, numbers of periods used per phoneme, and statistics to determine the number of phonemes spoken per second, and to determine the time an individual takes to speak common phonemes. The general principle is first to record the numbers of vocal organ motion events that are uniquely (in a statistical sense) associated with the vocal articulation of known sounds for the vocabularies being utilized by the user. Second, measure the number of pitch periods the speaker uses to say a small number of known phonemes (during training with known word sets).

Voiced-Unvoiced Statistics Algorithm for Average Speech Rate:

By measuring the number of times the comparators 78 and 79 in FIG. 19 are used in a given segment of speech (e.g. every 4 seconds) one can measure the rate of voiced vs unvoiced PLUs in the short time (e.g., 4 second) word sets and compare this number against the number in "standard speech". In this algorithm, standard is defined to be the speech rate for which the conventional CASR is set for processing or which is obtained by the EM algorithms for pitch period duration and number of frames used on training phonemes from a reference speaker or group of speakers. This can be used to normalize the duration and number of pitch periods used by the individual speaker to the number used by the referenced speaker group.

Tongue Motion Statistics Algorithm for Average Speech Rate:

By using the tongue motion sensor 22 in FIG. 4, the number of tongue motions above a threshold can be measured for each time segment for which speech rate information is needed, see FIG. 16. This algorithm simply uses a threshold detector in processing unit 83 in FIG. 19. The number of times the tongue motions exceed the threshold each second is converted to rate of PLUs per second in the speech being spoken using training statistics. First, speech appropriate for the language-vocabulary being used is spoken into the system by both the reference group to define a library and then by the user during a training session. The number of threshold triggers are counted for the time interval exercise as shown in FIGS. 12 and 13, referring to processor 66, which contains the algorithm illustrated in FIG. 19. The two are compared and a ratio is derived that associates tongue motion threshold events of the user with a reference group. From this, knowing the number of speech frames, or the number of PLUs per second, the algorithm corrects the feature vectors of the speaker to be the same average time period of the reference group. During normal use by the speaker, the value can be adapted by examining the threshold count during any reasonable period of speech, and knowing the vocabulary, one compares the count to the expected count rate and makes the corrections. Similar statistics can be built up and used for other organ motions.

Combined Organ(s) Rate of Speech Algorithms:

It is clear from the two prior examples that more complex decision trees can be formed by using more than one NASR, each for its own statistical measurements of organ threshold triggering, which are then combined by statistical averaging to generate a final number for the speech rate signal.

Similar Sound or Difficult Sound Identifier Algorithm

Single organ motion detectors can be used to discriminate between similar spoken sounds or otherwise difficult word recognition problems because it is usually the case that the slight differences in similar sound patterns are associated with one organ motion, often incompletely articulated. As for voiced-unvoiced PLU discrimination, similar procedures are used in the more general method of differentiating between similar sounding patterns. The identification of the correct PLU using EM sensors is often made straightforward because different parts of an organ (e.g. tongue) move and thus reflect the signal at different times and with different intensities during the individual speech time frames (which define each PLU) in a given word cycle. As an example, the words "saline" and "sailing", shown in FIGS. 7A,B, are similar sounding and are distinguishable by noting that the EM sensor reflection data from the tongue tip and the tongue back, shown as position versus time, are easily distinguishable. In addition, by generating a reference library of feature vectors for triphones, which for the example above would include feature vectors for the confusing sound patterns /ine/ and /ing/, the feature vectors obtained during the speech time frames for the two different sounds can be compared to those in the library and separately identified and used to make the decision as to which is the correct identification in the algorithmic procedure in FIG. 14.

Limited Vocabulary and Word Recognition Single Organ Algorithms

Figure 23A:
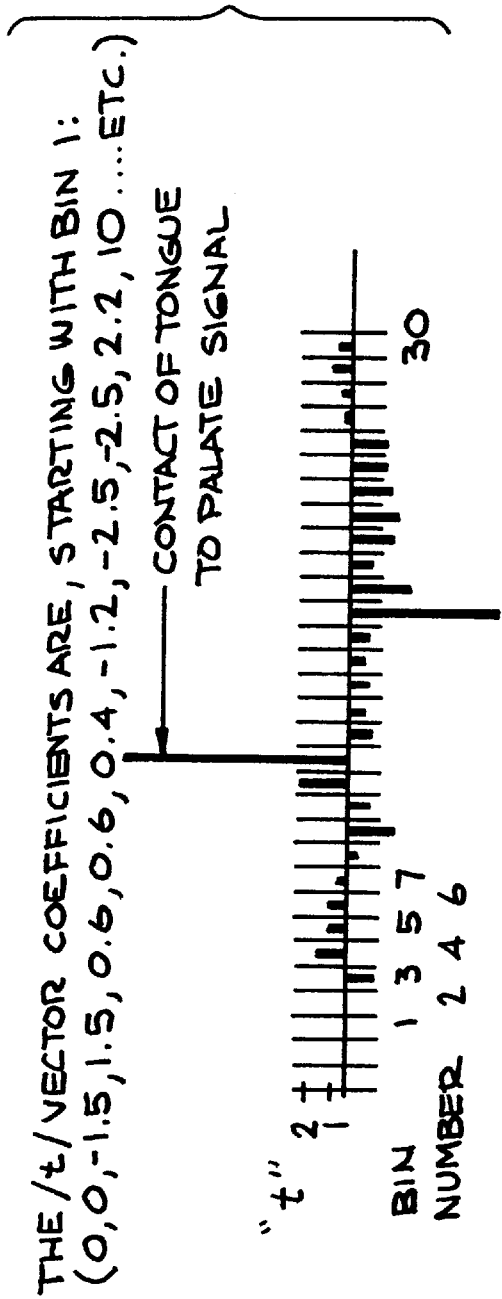
FIGS. 23 A,B illustrate graphically how the feature vector patterns for two phonemes "t" and "o" can be constructed from horizontal ranged gate EM sensor and a field disturbance vocal fold sensor, with stationary reflection artifacts removed.
Figure 23B:
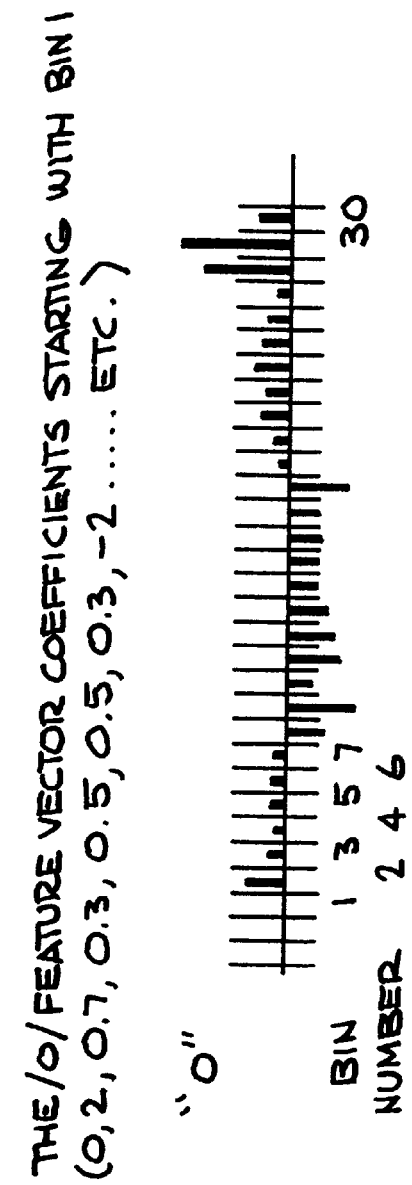

The use of a single EM sensor is especially useful for limited vocabularies used in specialized applications such as trading stocks or bonds, for banking, for catalogue ordering, for airline system reservations, where very high accuracy on limited word sets is important. Single organ EM sensors can provide very simple feature vectors to complement rather complex acoustic feature vectors for each speech frame. For example, an EM glottal pitch period sensor can have its feature vector be as simple as two coefficients, e.g., (8.2, 3) and (9.2, 2). The first vector means the EM sensor and algorithms measured 8.2 ms speech periods over 3 pitch period defined time frames during which constant pitch was measured. The second vector shows that two sequential 9.2 ms pitch periods were measured. When normalized, such pitch information constrains certain vowel identifications. A more complex vector, similar to the ones obtained from a horizontal ranged gated EM sensors for the sound /t/ and /o/ which are shown in FIGS. 23A, B and which are described by 25 feature vector coefficients describing the (non-normalized) positions of several articulators in a row from the lips to the velum. On can choose to use a subset of this data for single organ condition descriptions. For example, the three coefficients in each feature vector in bins 11, 12, 13 in FIGS. 23A, B describe the tongue tip motion.

For feature vectors designed for library storage and reference using these methods, several additional coefficients are added (e.g. ASCII symbols and time duration) that describe the sound associated with the organ condition coefficients. In addition, other coefficients that describe any recognition difficulties and system control coefficients would be added.

Another example feature vector is constructed by using the tongue jaw position data from FIG. 7 and for each vocalized pitch period (or default frame time duration value of 10 ms) form an average value of the position (i.e., the y-value from the curve). Since FIG. 7 shows no vocalized data, the vector is formed by averaging y-values for each 10 ms band along the x-axis. In this fashion, the algorithm constructs one coefficient for each time frame through the complete sounding of each of the words "saline" and "sailing". If this feature vector were to be stored in a code book, it would need additional coefficients that describe the word being coded, e.g. "sailing". In addition, one or two coefficients that describe recognition problems associated with this sound would be added. In this example, the added coefficients might describe the number of separate PLUs in the word to be 6, and the PLU for which a CASR system is known to have difficulty, the 6th, leading to a feature vector for this information (6,6). In addition, additional control coefficient locations would be added for overall system use, such as time duration of the total speech frame, information regarding onset or end of speech, and similar controls.

As an example of the process for identifying the spoken words "saline" and "sailing", the user would find that when using the algorithm described in FIG. 14, the CASR would have trouble with the differentiation because of the last three PLUs in the word which describe the sounds "ine"and "ing". The phonetician, in constructing a word library with these two words, would label that word as a problem word. The NASR recognizer for the tongue would identify the unknown feature vector with a front position to be "saline" if "ine" were spoken, and would identify the word as "sailing" if "ming" were spoken because the feature vector would describe a tongue back position, closed against the palate.

The number of extra information units to be added to the CASR library of PLU words to accommodate the information for NASR comparison is the number of organ positions being measured by each organ sensor, times the number of PLUs. In the single organ case, as few as one additional information coefficient is needed per word feature vector in the library to carry the extra information. Typical CASR feature vectors are 25 to 40 coefficients long in present systems; thus, the addition of one or a few more coefficients to interface the CASR systems with NASR systems in algorithms like FIG. 14 is not difficult nor does it place a significant burden on the memory size or processing speed of the system. On the contrary, the extra information makes the convergence much faster because the CASR does not have to resort to complex statistical techniques, or grammatical or syntactical techniques, to identify the acoustic unit spoken in the time frame.

The extra information provide by the NASR information can be used in several ways: 1) to increase the probability of correct identification, 2) to reduce the processing time of the CASR to reach a given accuracy because the NASR data more accurately distinguished many words than the CASR alone, so that the code book comparison is more accurate, and more rapid, because less statistical processing is necessary.

Multiple Organ Multiple Condition Algorithms

Multi-Organ Speech Time Frames

Nonacoustic EM sensors systems, when optimized to obtain multiple organ interface information each time frame, provide a great deal of information. See FIGS. 21A–C, 22A–B, and 23A–B. As time progresses, and as the vocal organs move to new positions for a new speech time frame, the new organ interface conditions (e.g. locations) can be recorded, processed, normalized, quantized, and new feature vectors formed. An automated algorithm for defining a new speech frame is needed to note that new speech organ condition information has become available to the recognition system and it must process and store it in a feature vector. Such an algorithm is defined as follows:

1) If voiced speech is present, the new time frame is defined as one pitch period, as described in the single organ time frame algorithm.

Figure 21A:
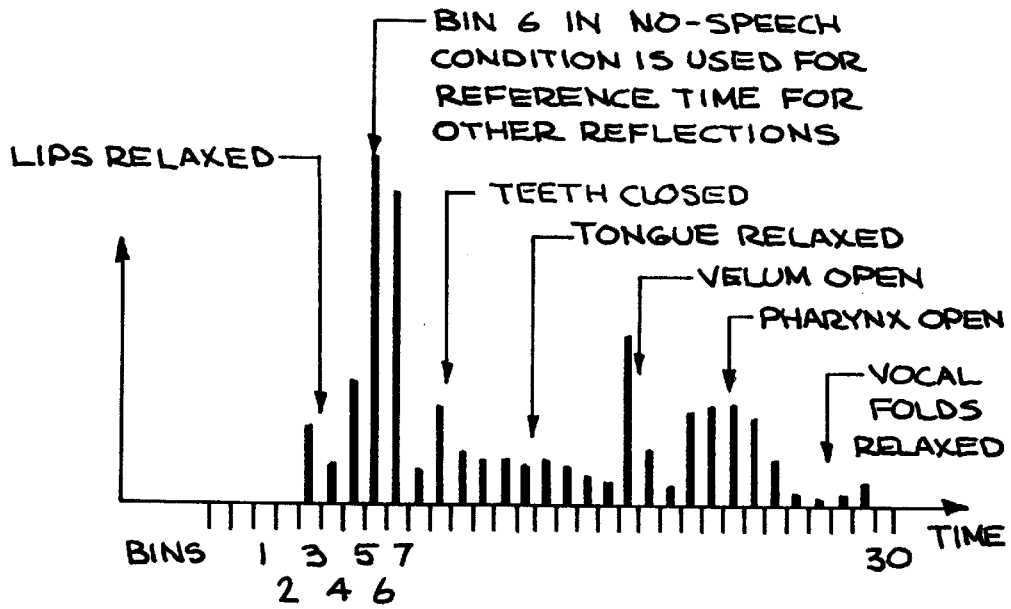
FIGS. 21A–C show digitized refection vs. position signals from joint feature vectors of horizontal range gated data and vocal fold open/close data, (A) shortly before beginning speech, (B) when the speech organs are in position to sound the phoneme /t/, and (C) the difference between (A) and (B) showing a method of removing background.
Figure 21B:
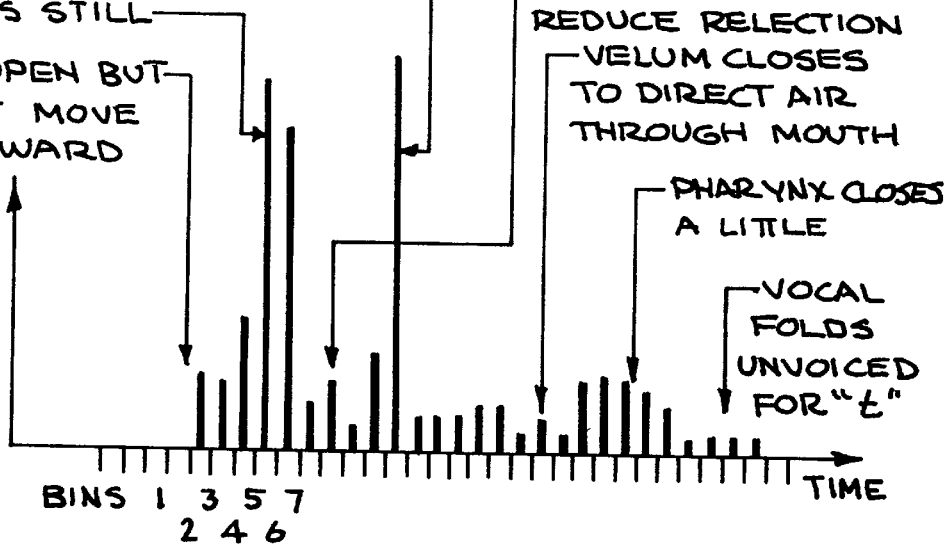
Figure 21C:
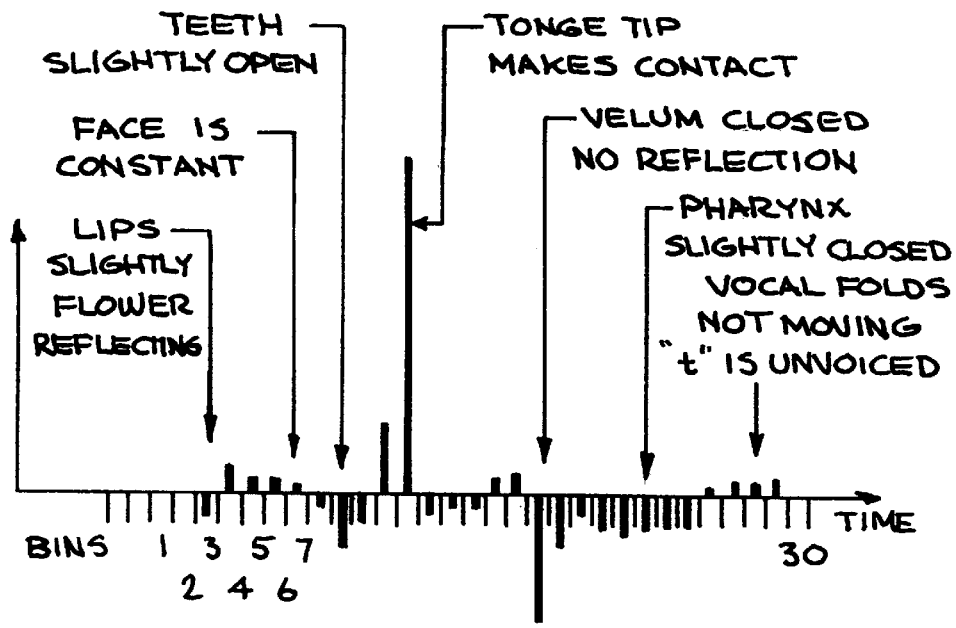
Figure 22A:
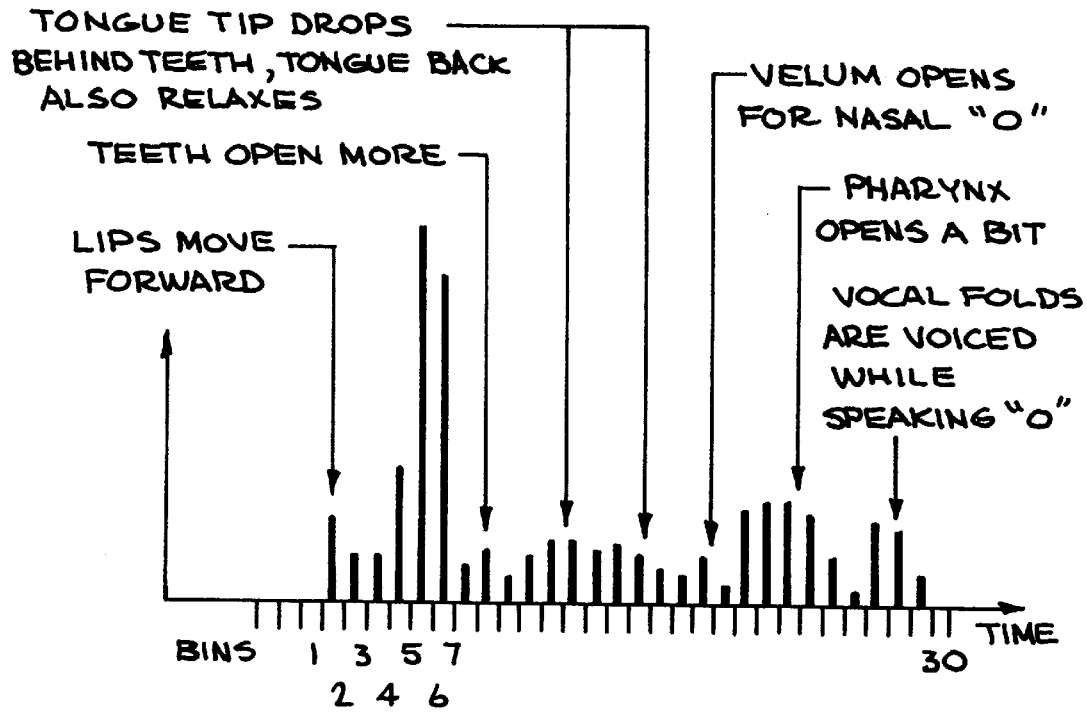
FIG. 22A shows digitized reflection signals identical to those in FIG. 21B except that the speech organs are in position to sound the phoneme /o/ in the word "to".
Figure 22B:
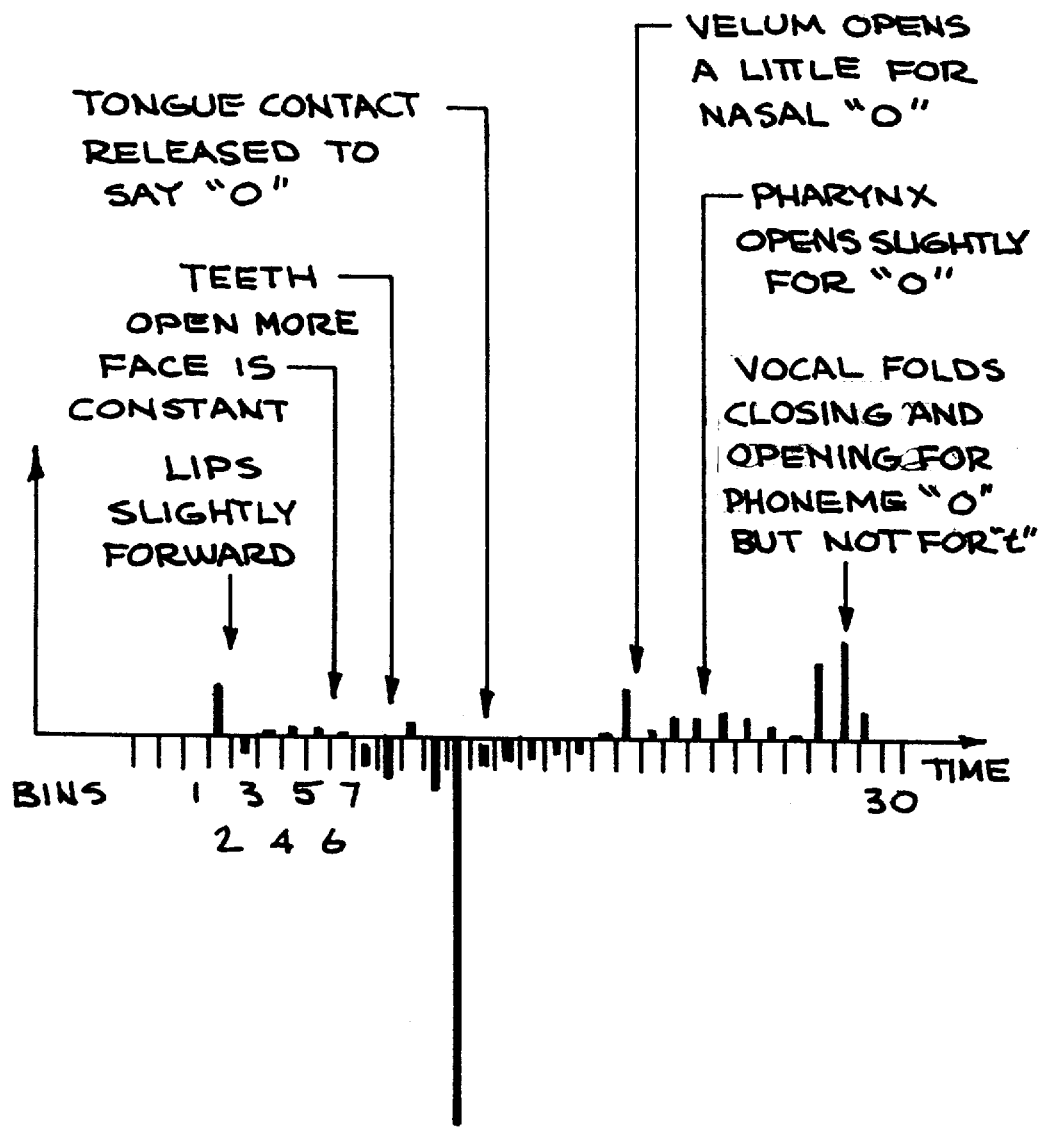
FIG. 22B shows one way of forming a diphone feature vector, by subtracting the feature vector for frame n from frame n−1, to form a velocity or motion vector between two phoneme speech frames.

2) If no speech or organ condition change (other than constant-spectrum vocal fold motion) has occurred, then a number of sequential voiced time frames can be joined together if they meet the following criteria. The algorithm compares one or more of the EM sensor feature vector coefficients and acoustic feature vector coefficients which are obtained from the newly processed speech time frame defined in 1) with those coefficients obtained from the preceding time frame. If any one of the identified organ coefficients change (i.e. the organ part moves) and if the acoustic feature vector coefficients change beyond a predefined level, the algorithm defines the termination of the existing frame and the advent of a new speech time frame. If no change is detected the length of the speech frame is increased by one speech period, and a control coefficient in the feature vector is incremented by one. FIGS. 21C and 22B illustrate how a feature vector obtained in a past speech frame can be compared to one taken in the present frame. The large changes in some coefficients of FIG. 21C, e.g., tongue contact in bin 12, show that substantial organ motion has occurred and a new speech frame is needed and was defined.

3) In conditions where no voiced speech occurs, the speech frame duration is defined as in 2), except that vocal fold condition changes are examined to determine onset of a new speech frame (e.g. a voiced PLU). This approach also describes the silence periods. The duration of such frames are recorded as a coefficient value in a feature vector control coefficient location.

4) A default value of 50 ms per speech frame is used if no other information is available, and if the "presence-of-speech" algorithms have not yet stopped system processing. Feature vector control coefficients are used to keep track of system conditions, length of speech time frame coefficients, start or stop times, etc.

Multiple Organ Condition Information

Feature vectors from many individual sensors, formed by using several EM sensor conditions of several speech organs in the same speech time frame, and using simultaneously recorded acoustic information (if needed) can be joined. together to generate a longer, more informative vector for speech unit (PLU) identification. See FIGS. 21A–C, 22A–B and 23A–B for examples of how horizontal EM sensor data feature vectors are joined with EM vocal fold motion detection to make a 30 coefficient vector that describes mouth organ conditions as well as vocal fold information. These procedures are similar to the procedures described above in Limited Vocabulary and Word Recognition Algorithms for single organ NASR systems. The organization of the larger number of coefficients of multi-organ, multi-condition vectors has to be well planned and tested ahead of time to obtain the correct constants and signal levels. One of the fundamental advantages of these methods is that they are based upon well understood fundamental physics, acoustics engineering, and mathematical principles each of which has been well tested in similar conditions. Thus, the use of feature vectors with many hundred or even many thousand coefficients is easily defined, obtained, processed using modern computers, and leads to very accurate identification of vocal organ conditions with the sounds being spoken. Only with the advent of these EM sensor based methods has it been possible to operate in real time, unobtrusively, safely, and economically.

Valuable multiple organ EM sensor measurements need not be actual position locations in a photographic sense, but may be complex convolutions of EM wave reflections from organ-air passages, from resonances of waves with organ shapes, multiple-interface interference effects, whole organ motions, or similar effects. An experimental example of this is the jaw/tongue motion data taken simultaneously with vocal fold motion, shown in FIG. 16. It provides very informative information, but the jaw/tongue condition is obtained as a complex, convoluted EM wave-organ interface reflection/attenuation signal, and is not at all a "photographic" or "tomographic" picture of the details of the tongue and jaw and all their interfaces. These less direct data nevertheless provide information that uniquely characterize important conditions of the observed organ(s) with the speech unit, e.g. PLU, being spoken. They can be normalized and quantized, and formed into a multi-organ feature vector each speech time frame for library or codebook reference. By using association techniques based on phonetic pattern matching, direct table lookup, hidden Markov models, joint or exclusive probability techniques, neural network models, and others known to experts in table look up techniques one can identify the PLU being spoken in each time frame.

Illustrative Data Acquisition and Multi-Organ Feature Vector Formation

As an example, by properly choosing a suite of EM sensors and their wavelengths, as well as pulse format, direction of propagation, receiver conditions such as sample-gate and/or homodyne phase, one can obtain a sequence of organ positional data as in FIGS. 10A–C and 11A–D. The A/D conversion, averaging, background subtraction, normalizing, quantization, and storing in short and longer term memory of the EM data is summarized in FIGS. 12, 13, and illustrative feature vectors are shown in detail in FIGS. 21A–C, 22A–B, and 23A–B. In particular, these simulated examples show lip-to-throat reflection data vs time (and thus distance) for the spoken word "to", taken (primarily) using a horizontal propagating wave as in FIG. 4, sensor 21. However, to illustrate the power of multiple-sensor multiple-organ information, vocal fold motion data is added to this set by placing digitized data from its sensor (FIG. 4, sensor 23) in time bins 25 to 28 of the horizontal digital data set illustrated in FIGS. 21A–C through 22A–B. (FIG. 22A shows that 40 ms after the simulated data for /t/, the articulators for the phoneme "o" in FIG. 21B would be positioned and ready for this sound.)

FIGS. 23A,B show a different feature vector rendition obtained by subtracting the vocal organ resting EM sensor signals from the data obtained one or more speech frames later. This processing technique removes uninteresting vocal articulator data as well as clutter from the background. The examples in FIG. 23A–B were constructed by subtracting rest articulator feature vector coefficients shown in FIG. 21A from those obtained when the organs have moved to articulate the PLU /t/ and /o/ in the word "to". This "differential" mode of description illustrates directional changes in the organ motions. When the position differences are divided by the time interval duration from the rest signal acquisition to the next organ configuration in the next time frame (see FIG. 23A) a velocity of organ condition motion is obtained. Such data provide strong constraints on organ motion or position model parameters and on acceptable phonemes that are associated with the vocal tract articulator positions. The changes in positions, over two speech time frames, strongly constrain phoneme pair representations such as those described by diphones and triphones. Examples are plosives, liquids, glides, diphthongs during which the articulators usually move continuously. Similarly, data from multiple frames can constrain multi-phoneme speech representations. More complex feature vectors than the ones illustrated above are easily formed by increasing the feature vector length by adding descriptive coefficients, in a well planned way, from the acoustic feature vector for the same speech time frame, and from other EM sensor generated feature vectors for the same time frame. Multi-speech frame feature vectors from sequential speech time frames can be joined together to make longer, more information rich vectors, and other combinations appropriate for the speech recognition or related application can be constructed. An important concept in multi-speech frame feature vector construction is the economy of information storage that occurs when one needs to only store changes in information from preceding frames.

Range Gated Multiple Interface Data

Figure 24C:
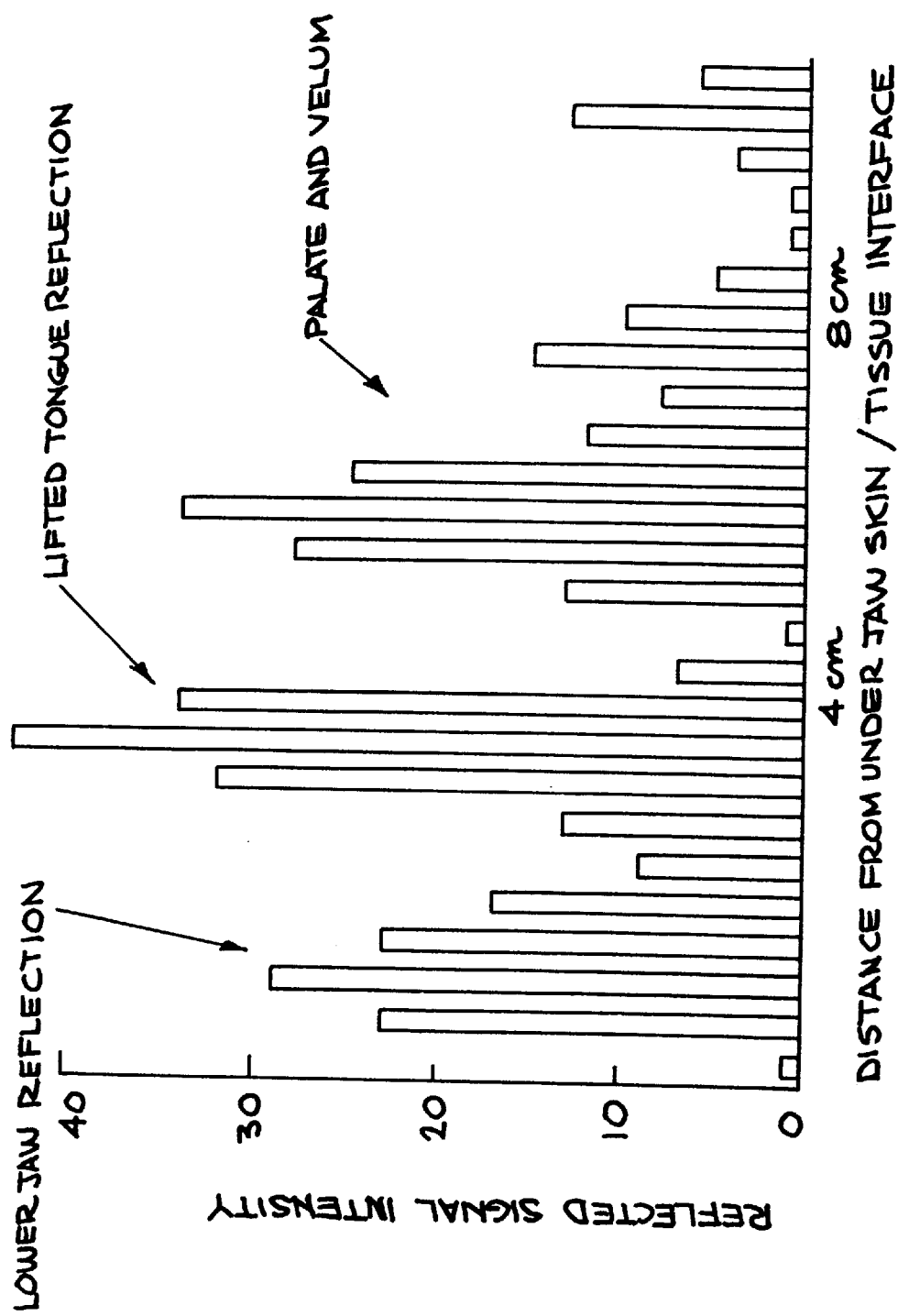
FIG. 24C shows an example of processed data with background artifacts removed and reflection signals "binned" by location from reference.

The use of range gated and other EM sensor data was illustrated in FIGS. 10A–C and 11A–D; a system for using the data in FIGS. 13 and 14, and illustrations of more complex feature vectors formed from such data are illustrated in FIGS. 21A–C, 22A–B, and 23A–B. Data of this type has been obtained by a range gated EM sensor which consisted of a 2 GHz micropower radar transmitter and receiver unit, which directed EM waves upward into the jaw, tongue, and nasal cavities. The time gating when converted to distance was accurate to a few centimeters. The reflected and detected wave patterns show a variety of signatures of reflected energy vs time (distance into the head) as a function of the positioning of the speech articulators for the sounds /uh/ in "one" and then /oo/ in "two", FIGS. 24A,B. The /uh/ signal compared to the /oo/ signal is associated with differences in a drop in the jaw, tongue body drop, the increasing of the tongue-body (blade) distance to the palate, and the nasalization in saying /uh/ in the /one/ sound. These, and similar, data clearly show the different organ reflections with different PLUs using these EM sensor conditions. The data is enhanced by subtracting the nonchanging background from the signals from each speech time frame. In addition, as shown in FIG. 24C, the data during a given distance interval are averaged and stored in "bins". These experiments and others validate the procedures illustrated in FIGS. 10A–C, 11A–D, 13, 21A–C, 22A–B, 23A–B.

Data Available—Multi-Organ Multi-Condition

An example of the information easily available (i.e., little signal processing is needed) from the multi-organ, multi-sensor methods is shown in Table III. The processing, normalizing and quantization procedures used to generate these data are described in Single Organ Normalization and Pitch Normalization.

TABLE III

Simplified Phonetic Conditions of the Vocal Organs Obtained by NASRs (i.e., EM sensor systems)

| ORGAN | ORGAN CONDITION | INFORMATION UNITS | VELOCITY or TIME RATES |
|---|---|---|---|
| vocal folds - position | voicing, not voicing, | 2 | |
| pitch rate | | 3 | hi/med/low |
| pharynx-glottis | open/nearly closed | 2 | |
| velic port | open/closed | 2 | |
| jaw | up/down | 2 | slow/fast |
| tongue - body blade) | up/down | 2 | slow |
| tip | up/down | 2 | fast |
| back | up/down | 2 | medium |
| lips | open/closed | 2 | slow/fast |

These organ position and velocity conditions, all together, provide several thousand information combinations to be applied to the description of one of the 50 PLUs, or other acoustic sound units, spoken during each speech time frame. Many PLUs require multiple time frame descriptions because they are "moving" sounds such as "plosives" (an example is /d/ in "dog" where the /d/ is sounded by the tongue and jaw rising and dropping rapidly). Moving sound PLU categories are called liquids, glides, diphthongs, and others. (see Olive ibid.) To estimate the information units available, using an average of two time frame feature vector coefficients per PLU, the amount of information from sensors and their allowed values as shown in Table III, is simplistically calculated to be in excess of several million units. However, a large number of organ conditions, described in Table III are not independent of each other in a given language and thus the combination number is reduced substantially, but exceeds many 1000s of units. This estimate on the number of EM sensor measured conditions does not include the additional information commonly obtained and described as a feature vector from the acoustic sensor each speech time frame. The acoustic feature vector can be joined to an EM feature vector to make a longer, more informative feature vector. The information available vastly exceeds the number of basic acoustic sounds in any language, e.g., English uses 50 PLU's, 256–512 acoustic units, 2000 English demi-syllables, and 10,000 syllables (Ref. Rabiner p. 437 ibid.).

Words feature vectors require that several PLU feature vectors be joined together to make the whole word feature vectors. When this is done, the information available exceeds a million units, which is greater than the number of words used in natural English speech. With accurately formed and normalized speech feature vectors for each speech frame, and when using modern table look up techniques, identifying a match to one of 10,000 code book vectors is straightforward and a match to one of 40,000 or more vectors to identify words is straightforward.

NonSounded, Whispered or "Mouthed" Speech

The consequence of having available, through suitable choices of EM sensor systems and processing algorithms, the large number of identifying parameters is that it is possible to identify the acoustic sound unit being spoken each speech frame without measuring the acoustic output. The information available on the condition of the vocal organs each time frame (including open-close motions but not repetitive cycling of the vocal folds) makes it possible to identify intended speech units from finite vocabularies that are useful in several applications. The algorithm that is used is described in FIG. 14, except that the CASR system is turned off, and the speech unit with the highest probability of identification by the NASR is defined as being recognized. In particular, this algorithm is very valuable for noisy conditions when acoustic CASRs are being used in conjunction with NASR systems.

The measurement of speech organ motions, with or without simultaneous speech, makes it possible to create synthetic languages that are optimized for special applications. For example, very small "vocabulary" tongue-language can be used to direct a wheel chair to move left or right, forward or backward, or to stay steady. The communication is accomplished by the user moving the tongue right and left, up and down, or holding steady in the middle of the mouth for the respective motions. This synthetic language is used by first forming feature vectors for the tongue conditions, and comparing those feature vectors to prestored vectors in a reference code book with associated machine control commands. Upon identification, the command is executed. Similarly, a rapidly moving tongue can be used to signal turn-on for a cellular phone. More complex vocabularies using multi-organ motions and accompanying human sounds can be generated as needed for specific applications.

The addition of whispered (i.e., low level unvoiced but sounded speech) adds additional information to the zero sound condition that can be useful in low noise applications and can increase the accuracy of intended speech unit identification. In this case, the algorithm in FIG. 14 uses the CASR information, but the feature vectors in the library of whispered speech units are labeled regarding the difficulty of their identification using whispered acoustic speech data. The algorithm in FIG. 19 is also set to assume that the acoustic speech amplitude is zero or less than a value appropriate for whispered speech.

Words

A word is a sequence of primitive acoustic sound units, e.g. PLU units, and word feature vectors describing a word (or short phrase) can be constructed by joining together the feature vectors from each PLU into longer and more complex, but still manageable, feature vectors. Such composite feature vectors are very effective when used with limited vocabularies, and they are also useful for more complex vocabularies. The added information, both in quantity and quality, afforded by the NASR systems make possible much improved definitions of word units. Methods to construct multiple acoustic unit feature vectors, e.g. 2 to 10 sequential PLUs, have been described earlier. The normalizing, quantizing of coefficients, and definitions of multiple pitch period time frames are straightforward to implement for larger, composite word feature vectors of words and phrases. These procedures work well for the definition of word units knowing, a priori, the sequence of acoustic sound units, such as PLUs. These procedures are used to make code books and libraries for referencing by speech application algorithms, including the recognition application. The inverse problem, i.e., recognition, is more difficult and is discussed below.

An example of a process for generating a composite feature vector for a word or phrase is to simply string, end to end, the coefficients from sequentially obtained feature vectors. An example would be to take the two illustrative feature vectors from the vocal fold EM sensor described in Limited Vocabulary and Word Recognition Single Organ Algorithms which have 2 coefficients each, e.g. (8.2, 3) and (9.2, 2). One makes a composite vector (8.2, 3, 9.2, 2) for a hypothetical two PLU word with 5 total speech frames of sound, and total time usage of 43 ms. A more complex example is illustrated by considering the 30 coefficient feature vectors for the separate sounds /t/ and /o/, shown in FIGS. 23A,B. One constructs a 60 coefficient feature vector for the word /to/ by joining the two 30 coefficient sequences. By adding acoustic feature vectors for the two speech frames as well, each for example 25 coefficients long, and adding 20 system control coefficients, special information coefficients, and the ASCII coefficients for the two letters and word end symbols, one has a very well defined feature vector for the word "to" that is 130 coefficients long. In a third experimentally verified example, using the EM sensor output of jaw/tongue in FIG. 7, one constructs a feature vector using the curve values each 10 ms over a period of approximately 1 sec. This makes a separate 100 coefficient vector for each of the words "saline" and "sailing". Several methods of simplifying such long vectors are available to remove redundant information, including "slow change" feature vector definitions, coefficient normalization and quantization, and time-frame to time-frame feature-vector-coefficient difference generation.

The word start and stop problem is not solved automatically by the NASR systems. The identification of word transitions requires additional information beyond the identification of the sequences of acoustic units such as PLUs. The procedures are described well in references on acoustic speech recognition such as the work by Rabiner ibid. and the references contained therein. However because of the accuracy and normalization capabilities of the NASR system, the user has many more "cues" to use in assisting in the definition of the word ending, and next word beginning events. Much of the additional information available from NASR systems is illustrated in FIGS. 25A–H which show simultaneous acoustic and vocal cord motion data, and FIGS. 26A–D showing all four sensors as illustrated in FIG. 4, both taken as a male speaker spoke the sentence: "The quick brown fox jumped over the lazy dog's back." Examples of many of the features described above are shown, including simultaneous acoustic and vocal fold stops, emphasis (i.e., prosody) changes, PLU breaks, word starts and stops, pre-speech glottal tightening, and vocal fold rate transitions. FIGS. 25A–H clearly show the effect of pitch change for differently voiced sounds, unvoiced starts for /f/, /b/, /p/, word separations, pauses, and other phenomena.

Nevertheless, nonacoustic EM sensor data clearly shows the running together of words by speakers, and such conditions are not automatically recognized by NASR systems. However a characteristic EM sensor signal change is always observed for every sound change that denotes the start or stop of a PLU. As a consequence, the user of these methods has very good markers between the acoustic units. Secondly the capacity to define each PLU change means that it is possible to sequentially analyze long strings of often run together, but clearly defined, normalized, and quantized feature vectors to use for testing against multi-word (i.e., phrases) libraries. In addition word spelling, grammar, and syntax rule generators can be used, as they are for CASR systems, for separating run together words from each other. In particular, the capacity of the NASR system to find incomplete, or co-articulated conditions and the redundancy of information provides important new procedures to identify the phonemes that are run together, but incompletely articulated.

Word Signatures in Association with Conventional Speech Recognition

There are many applications where very high accuracy recognition of limited vocabularies has great application. Examples are financial trading, and airline reservation taking. The vocabularies used in these situations typically have 1000 words or less. Present acoustic processors work on these vocabularies by demanding that the speaker speak clearly, distinctly, and be in a low noise environment. What is needed is additional information that is statistically independent of the acoustic data in a measurement sense, so that the probability of error of the new data sets can be joined with that of the acoustic information to yield an acceptable error budget. Acceptable quality is usually defined to be human speech like, which is 1 error in 10,000 words. This quality in limited vocabulary sets can be achieved by using the combinations of sensors that very strongly constrain the selected word, by using the simultaneously obtained acoustic data, and by using spelling, syntax and grammar correctors to correct minor remaining problems.

The algorithmic decision process illustrated in FIG. 14 can be used for multi-PLU word feature vectors in the same way as was described for feature vectors describing single PLUs. A library is constructed of all word feature vectors needed for the limited vocabulary by the user or a reference speaker(s) using the same set of EM sensors for the actual application. Trained phoneticians can label those words from the limited vocabulary which are known to be difficult to identify with high probability or those that are known to be improperly articulated when spoken carelessly. This means over 1000 words will be spoken into the system, then processed, normalized if desired, phonetically labeled, and stored in known locations in a library (memory). The algorithm follows as in FIG. 14; the conventional recognizer, CASR, identifies the closest word feature vector or several feature vectors from its library depending on how statistically close the incoming feature vector pattern is to those in the library. However, the library contains along with the CASR identifiers, information that certain words are difficult to identify, and need additional NASR identifying probabilities to improve the overall recognition probability. The NASR recognizer is consulted for its information from the speech time frame, and the multi-sound unit feature vector, fitting both the CASR and the NASR, (in a statistical sense) is chosen.

The algorithm, FIG. 14, used for the defined vocabulary problem is to take two sets of data, one with CASRs and the other with two or more NASRs. The word definition and identification is done first by the CASR using an expanded code book which has information in it referring to the expected NASR validation criteria. The NASR data set for each word can contain several types of information. Multi-coefficient word feature vectors, constructed from a whole series of PLU feature vectors have been described.

A very simple algorithmic procedure, is to not use the EM-sensor data to form individual PLU units and subsequent composite feature vectors. Instead, a library of NASR words are constructed as described under Words, wherein a special feature vector is formed by storing the measured organ condition versus time, using fixed time steps or time bands. This algorithm was demonstrated using the data in FIG. 7 for the sounds "sailing" and "saline". In one use of the procedure, the EM sensor data is digitized, averaged, normalized, and quantized over 10 ms speech time frame intervals (for example), and stored in a memory "bin" for each 10 ms data set. This process continues from the beginning to the end of the training word and is used to form a vector 50 components long (for a 0.5 second maximum duration word). For shorter words, many components in the standard vector will be zero; for longer words a longer standard vector length may be used.

Improvements to this algorithmic word and phrase technique include the use of automatic speech frame generation, together with organ condition and pitch period, and speech rate normalization. In addition, the vector length can be automatically defined by using the onset of speech algorithm to determine the first feature vector coefficient, and using the end of speech algorithm to define the last coefficient during the library formation phase.

Figure 27:
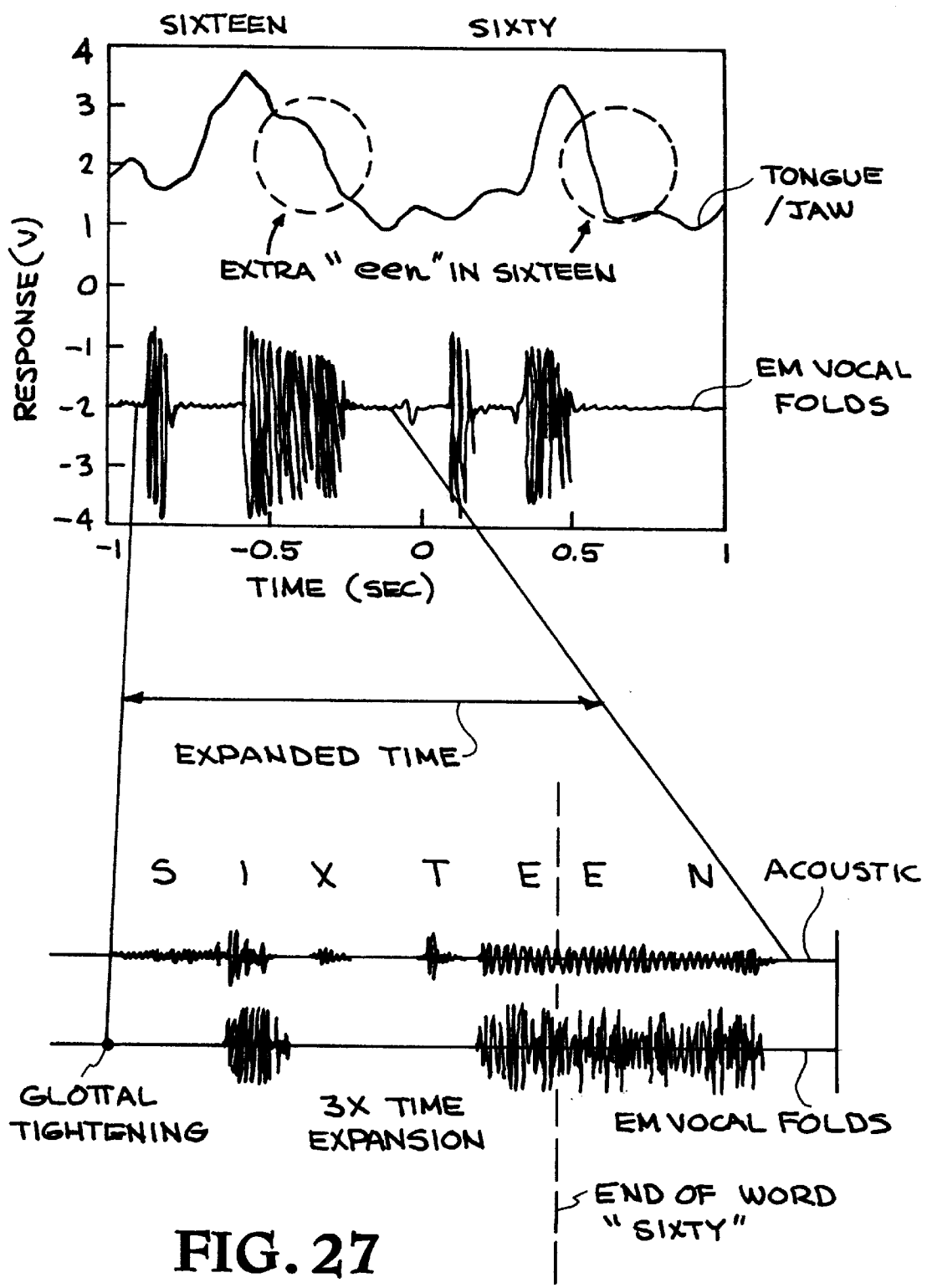
FIG. 27 shows the EM tongue/jaw and vocal fold signals for "sixteen" and "sixty".

Another example of the data that would be quantized, averaged, and stored every predefined time interval is shown in FIG. 27 which shows simultaneously sensed acoustic, tongue-jaw position, and vocal fold motion as a speaker says the two words "sixteen" and "sixty". For this example a vector for a 0.7 sec word length of 50 components is used, and the sensor data was averaged every 15 ms. The tongue-jaw sensor easily notes the differences between the words. In "sixteen" the word is longer and the tonguejaw signal stays high longer than in "sixty". The "een" sound in "sixteen" is clearly shown in contrast to what is seen in the word "sixty", and more sequential coefficients in the feature vector for "sixteen" would have similar values than in "sixty".

Distinguishing between the two words "sixty" and "sixteen" is very important in financial trading. However these two words are often confused with each other by conventional acoustic recognition systems optimized for financial trading. In contrast, the words "sixty" and "sixteen" are not confused with other words often used in this speech recognition application such as "dollars" and "bank" where the CASR does a good job. Relatively little extra information is required to "help" the CASR to distinguish between the two acoustically similar sounding words "sixty" and "sixteen", and the accuracy improves dramatically as a consequence. In similar sounding words or in "difficult words" there is usually only one relatively short information segment to distinguish them from each other, see Rabiner ibid. p. 291. The use of the feature vector coefficient normalization techniques and the speech period normalization techniques help remove individual idiosyncratic variations, so that these short segments showing differences are available for pattern matching.

In summary, whole word description vectors can be constructed from a series of feature vectors from sequential speech time frames. The composite vector can be compared, in a post processor mode, to known vectors for other words in vocabularies with word counts ranging from <100 to >10,000 words. That is, after a conventional acoustic speech recognition system makes a decision, the decision is compared against the EM sensor word data to validate the decision as illustrated in FIG. 14. If it is validated with acceptable probabilities, then the word is accepted as recognized; if not, then a best guess is made using the EM-sensor generated data set(s) to discriminate from the subset of words constrained (but not uniquely identified) by the CASR system. Because such acoustically confused words are usually only confused with one or two similar sounding sounds within the words in the constrained set, the EM data easily allows the selection of the correct word with high probability. It is straightforward to extend this algorithmic concept to usefully sized word sets of many hundred to many thousand words.

Speaker Identification

The capacity of the NASR system to accurately define speech time frames and associated feature vectors during the course of sounded speech makes it especially valuable for identification of the speaker using the system. The algorithm is the same as Single Organ Normalization and Pitch Period Normalization, with a few modifications. In the normalization algorithms, as used for speaker identification, the reference speaker is defined to be the owner, or the named person to be identified. At some previous time, the identified person was asked to speak a series of training phrases into the NASR system and a library of his feature vectors was formed. Such a library can be constructed from isolated sounds such as phonemes, but improved recognition is obtained when using higher multiphone units and phrases such as his name or password to construct the library.

The system operates by asking the user (or pretender) to speak specific passwords or to speak segments of the language that have several of the identifying multiphone units in them. Standard nonacoustic processing is conducted by the methods described above, and a standard pitch and feature vector normalization procedure (for all organ sensors used) is conducted. The algorithm diverges from normalization and mapping at this phase, and instead differences between the feature vector coefficients of each speech frame for the training set sound units and those in the reference library are formed. Next the algorithm stores the differences of each coefficient value in a second (parallel constructed) feature vector. The coefficient values of the difference feature vector will be low if the speaker is the same person whose voice was used to form the identification reference library. A measure of identity is obtained by first choosing which of the coefficients in the second feature vector are most important to be used as test values. Then the values of each of these coefficients are squared and all squared values are added together. The algorithm then takes the square root of the sum of the squared values to find a total measure of difference. If it is below a preset threshold, identification is accepted. If the value is above the threshold, the attempt to be identified is rejected. In transition cases, the system can ask for additional information to try again.

The types of feature vectors that are used for the identification vocabulary are chosen for the application. For special high security systems, special test words and phrases are chosen that measure the extension of the users vocal articulators and the time duration of the speakers speech periods, the time duration of speech units and multiphone patterns, and organ velocities between speech units are measured and stored in the feature vector as well. Much simpler systems can be used for lower value applications. The NASR speaker identification system is very valuable because the comparison procedures and process for data taking are essentially impossible to fool, especially since the EM signals can be randomly transmitted by the generator to the user and they can not be simulated with prerecorded data.

Large Word Vocabulary, Natural Speech Algorithms

In natural English speech over 60,000 words are used when names and technical words are included. Data is obtainable from multiple EM sensors and related processing algorithms (i.e., NASRs) to easily distinguish the 60,000 different words used in English and in any other language. With the over sampling, and additional information gathering time available during whole word time periods (including pauses between PLUs), and the use of acoustic recognition techniques, several times the needed information per time frame is available for word identification. These word identification vectors can be generated by combinations of EM sensor systems and algorithms, and acoustic sensors and their algorithms. The actual table look up techniques (i.e., code book or library lookup) can be accomplished using direct phonetic lookup in code book space, Hidden Markov Modeling, neural network models, and other known statistical techniques. The use of accurate, normalized, feature vectors makes it possible to use the vector coefficients as direct library look up addresses for the direct identification of the feature vectors.

CONCLUSION

The invention is a method of speech characterization that uses electromagnetic (EM) radiation scattered (i.e., reflected and or/attenuated) from human speech organs in concert with acoustic speech output for the purposes of speech recognition, speech synthesis, speaker identification, speech prosthesis, speech training, speech coding, speech synchronization, and speech telephony. The method includes applications to all human communication associated with vocal organ usage, including normal sounded speech, whispered speech, and non-sounded speech communication, e.g. zero acoustic output but "mouthed" output. The method can be used for all human acoustic languages. The method can also be used in all animal communications where motions of animal vocal structures can be used for obtaining non-acoustic information, in conjunction with acoustics, that are useful for understanding and implementing valuable and improved animal communications, e.g. dolphin speech.

The method includes the use of acoustic microphone(s) for the detection of acoustic output of a speaker through the speaker's mouth, nose, or by acoustic radiation through the throat, or other parts of the speaker's body, in combination with EM radiation organ condition detectors. The information measured includes, for each sampling time, the acoustic pressure or sound intensity. By measuring the acoustic intensity over several sample times, a measure of the frequency, the zero crossing times, the energy per time interval, the cepstral coefficients, and other well known characteristics of human acoustic speech can be obtained using frequency transform methods.

The method can use information from EM wave acoustic microphones that detect acoustic vibrations of human tissue, using EM wave sensors. Because of the indirect nature of such EM microphones, an adjustment step is required to obtain the frequency response function of the individual to the EM sensor unit. Once the received signal is corrected for this response, the methods of acoustic information processing are the same as those described herein for acoustic microphones.

The method includes, with acoustic measurements, the use of any EM wave generating, transmitting and detecting system, including RF, microwave, millimeter wave, infrared, or visible wave radar that can penetrate the first surface of the skin, as well as reflect from the first skin-air surface. It includes their use in nonradiating modes, in radiating modes (i.e., radar), or in mixed nonradiating/radiating modes. It includes the use of coherent or noncoherent generation and detection of any EM waves, and the use of timing to obtain spatial location and time varying information. Examples using radiating (i.e., radar modes) include using a range gated reception system to detect and store reflected EM radiation from body tissue-air, tissue-bone, or tissue-tissue interfaces, or from any other configuration of human body parts that scatter radiation during the speech process. This method provides information on the positions and presence or absence of speech organ interfaces by measuring the time between transmitted and received EM signals, i.e. as the EM wave travels into the body, it is attenuated and reflected from discontinuities. Changes in attenuation or reflectivity as measured by subsequent EM emissions, with or without time of flight information, provide information on interface motions. By repetitive generation and detection of EM pulses, this method provides a sequence of speech organ condition information as the speech organs progress through the speech cycle of the speaker. Such a sequence of EM pulses can be time ordered simultaneously with acoustic measurements of speech, or with other measurements of speech organ conditions, coded and processed for the purposes of recording, for recognition, telephony, and other applications. A variant on this method is to measure the reflections and attenuations from all organ interfaces reached by each transmitted pulse train (using one or zero range gates), and to use time filtering as subsequent pulses are transmitted and received. Organ reflectivity changes are separated by their time signatures of change as the organ conditions evolve (e.g. field disturbance radars).

This method does not use scattered, incoherent EM radiation, in the visible or near IR region of the EM spectrum, from only one skin-air surface which has been received by an imaging TV camera and used in speech recognition as an aid. It does not use such radation, for example, in visible lip shape analysis which is used to aid in the acoustic recognition of certain speech phonemes such as "b" which are associated with lip opening and closing. It does use EM radiation, including visible and IR spectral information, that scatters (i.e., reflects and is attenuated) off both the first skin-air surface as well as from interior surfaces by penetrating the skin and propagating through interior tissue, bone, air cavity structures, along with simultaneous acoustic information.

The method uses coherent mode EM transmit/receive systems, along with acoustic information, where the phase of the received wave is compared in a linear or nonlinear fashion to stored phase information of the transmitted wave or to other locally generated phase information, e.g. homodyne, heterodyne, or other "interferometric" coherent detection techniques. These methods are especially useful for organ condition detection systems because the target is so close, as defined by the number of EM wavelengths, to the transmitter antenna(s). These detection methods can use time gating, sequential transmissions with changes in phase or wavelength, or both simultaneously. These coherent mode methods can be implemented with EM wave sensors operating in the near field of the antenna-like structures, in the intermediate field, and/or in the radiating far field.

The method uses monostatic, bistatic, or multistatic reflected, scattered (e.g. side, forward, or backward scattered wave) systems consisting of one or more EM transmitters and receivers. They generate EM waves that reflect off dielectric and/or conducting discontinuities in the human vocal system, along with acoustic information. It includes the use of single, multiple, or swept frequency EM transmit-receive systems for the purposes of obtaining speech organ state information (including individual or relative organ positions to other organs), that provide information pertinent to the dimensions of the organs, to the relative positions of discontinuities within an organ or between organs, and to the scattering strength of the EM wave. In this method, an EM wave of appropriate wavelength reflects from one interface and adds coherently to an EM wave reflecting from another interface. In the case of constructive interference, a very large reflection associated with the square of the sums of the wave amplitudes is detected. Similarly, reduced reflection can occur when reflected wave amplitudes destructively interfere, the detected reflection is canceled (or reduced), and it leads to a stronger forward propagating wave. Such EM wave transmitted and received information is recorded along with simultaneously measured acoustic information.

The method, along with measuring acoustic information, uses special antenna structures for directing and focusing EM radiation for the purposes of determining the conditions of certain speech organs or organ interfaces; it uses impedance matching devices for minimizing reflections at the first skin-air interface; and it uses dielectric materials to slow the wave propagation before it meets the skin for purposes of increased timing accuracy and for spatial focusing. It also uses EM sensors with multiple antennas, single package EM sensors with both transmitter-receiver units, as well as EM wave transmitter units separated from receiver units which can be located along or around the head, neck, or upper body for the purposes of ascertaining the conditions of organs used in speech production from the appropriate angles. It can include the sensors attached to other structures, e.g. an auto dashboard. It also includes techniques that make use of "glints" or coherent resonances from the target organs or organ interfaces, and it includes methods to remove sensitivities associated with changing EM scattering sensitivity associated with changes in the relative positions of the transmitter-receiver antennas to the speakers head, neck, or upper body.

This method uses a control unit that determines the time of generation and detection of the EM waves, including for example on, off, quiescent state timing, and the simultaneous reception of acoustic waves (with time-of-flight corrections), or other detectors. The method of control includes setting the transmitted frequency and pulse packet duration of the EM waves, determining master timing of all components in the system, determining the received range gate timing, determining the number of transmitted pulses per reception time, averaging or other noise reduction, controlling the A/D conversion of the voltage levels of the electronically stored pulses, setting the amount of averaging and types of pre-processing of the received EM waves, placing the preprocessed information in temporary or long term storage locations for subsequent algorithmic processing and use. This control system may be analog, digital, a hybrid of the two types, and may be in one localized location on a circuit board or chip, or it may be distributed.

This method uses a data processing system to create an efficient vector of information that accurately describes the "features" of the acoustic signal as well as the "features" of the measured organ conditions during a predefined time frame of speech. These features including timing information. Initially acoustic and EM feature vectors may be separately constructed and then combined by algorithmic procedures. This method uses a means for processing the EM and acoustic information according to a prestored set of instructions or algorithms, e.g. hardwired, or placed in ROM as software stored instructions, with the purpose of generating a defining "feature vector". This method uses a means of storing such feature vector information in an electronic library during what is known in the art as "training periods" (libraries are also known as codebooks to experts in speech technologies). It uses a means of accessing such previously stored library information during the processing sequences, a means of storing processed information in longer term memory or computer storage systems, a means for transmission of the processed speech information to other systems or subsystems as time progresses, and a means for visualizing or acoustically sounding the derived or raw information as the speech process evolves in time.

The method can be carried out under conditions when the acoustic sound pressure sequence emitted by the speaker is zero, or below accurate detection levels in intensity, i.e., the organ motions of intended speech themselves are sufficiently accurate to determine a valuable level of communication by the speaker. This method can be used in a very noisy environment. Other related signals associated with speech can be present and can be used in conjunction with the EM signal data to define the speech unit from the speaker. This method includes the simultaneous recording with EM transmitted and received information, of skin potentials that are associated with speech organ motion and speech formation, the simultaneous recording and use of ultrasonic sound imaging systems providing vocal organ system data, the use of simultaneous video signal information, and the use of air flow information. It also includes the association of EM scattering with information obtained by invasive techniques such as micro-beam x-ray units (with or without metallic attachments to the vocal organs), magnetic resonance imaging units, magnetic position detectors using signals obtained from implanted or glued electrical coils or magnets attached to speech organs, as well as strain gauges, conducting materials, optical imaging devices inside the vocal system, and air pressure or flow gauges.

The method also uses, simultaneously, acoustic information and EM derived speech organ interface velocity information for determining the state of one or many vocal organ interfaces or organ bodies. To obtain velocity information, two or more measurements of organ positions must be obtained. The velocity is derived by dividing the difference in organ positions by the time difference of the measurements. Typical speech organ motion cycles are 10 ms for several mm of motion during the (male) vocal fold open and close cycle, tongue tip motions of 1 cm in 20 to 100 ms, and jaw up or down motions of 1 cm in 0.1–0.5 sec. Speech organ interface velocity information can easily be obtained at a rate that is faster than the significant motions of the organ interfaces, because the EM transmit-receive systems obtain information at up to several million times per second, more than a thousand times faster than the organ motion cycles. Average velocities of entire organs or detailed velocities of specific organ interface locations are all of value, and the method of measurement is chosen by the practitioner depending upon the application. Such information is especially valuable because speech organ velocities change sign as the organs move and retract to position themselves for phoneme sound generation or upcoming phoneme sound generation. Thus, the velocity zero crossings providing accurate and valuable timing information. The method can also measure changes in velocity over two or more time frames which yields acceleration data which are obtained and used as is velocity information.

The method uses, but is not limited to, combinations of speech organ specific interface position information, speech organ body average position information, and speech organ interface velocity and/or organ body average velocity information, together with simultaneous acoustic information, for the purposes of speech processing.

The method can use speech organ velocity information, together with speech organ position information, where the acoustic signal intensity is zero for the purposes of valuable non-acoustic communication or speech organ condition measurements. The method can use speech organ velocity information, together with position information, where the acoustic signal intensity is zero but where other (e.g. magnetic, video, air flow) simultaneously recorded speech organ descriptive information is available for the purposes of valuable communication from speaker to user or for measurements of the condition of the speech organ.

The method produces "feature" vectors for the position and/or velocity of vocal folds during a defined single speech time interval frame or for a defined multiple series of time interval speech frames. These featured vectors can be analyzed to obtain the pitch period of the speaker's excitation function over a single period and over multiple periods. This is accomplished by properly defining the direction, frequency, and dimension of the EM wave propagation path and by analyzing the reflected and or attenuated return signal using time domain techniques or frequency domain techniques over one or several similar periods.

The method "normalizes" the position and temporal feature vectors of an individual's speech and maps them uniquely to a feature vector of a referenced individual or of a group of individuals (e.g. to an average speaker of the language). This method includes training an algorithm by asking the speaker to pronounce a set of words that determine, as needed, the amplitude levels, the position-limits, the velocity-limits, and the timing-limits of the individual's vocal articulators for the EM sensor suite in use. The method then assigns a one to one correspondence from each EM sensor signal, that is associated with the speaker's articulator condition at the moment of measurement, to an EM sensor signal value from earlier measurements of reference (i.e., normal) speakers. Furthermore, the normalized signals can be quantized into bands reflecting the constancy of perceived sound when the articulator condition is within a given band. This method then stores these normalized and quanitzed signals as a normalized featured vector for the time frame or frames being measured.

The method can be used for determining whether or not voiced speech, or unvoiced speech, or speech or background noise has occurred in the defined time interval frame or over several defined time frames.

The method can be used for defining start of speech by onset of vocalized or nonvocalized phonemes, or by noting vocal fold motion, surrounding glottal tissue or other organ motion precursors during a given speech time interval frame or over several defined time frames. Similarly, this method can determine end of vocalized or nonvocalized phonemes, the presence of external noise interference, and pauses.

The method can be used for determining the presence in a speech segment of a "glottal stop" and thus the end of air flow. It shows an end of vocalization during a given speech time interval frame as repetitive glottal motions cease. Also a glottal opening at the beginning of unvoiced speech can be determined, and transitions from unvocalized to vocalized speech can be measured.

The method can be used for determining the pitch or pitch change of voiced speech by using glottal tissue position or velocity information from two or more voiced speech-period time frames by using time domain or frequency domain techniques.

The method can include using the EM system and specific EM sensors and algorithms for the glottal tissue structures (including vocal folds) to obtain basic mechanical, acoustic, and fluid flow information defining the characteristics of the individual speaker such as tension, resonance frequency, compliance, mass, spring constants, area vs. scattering strength, and other well known constants used in acoustic, mechanical, and EM scattering models of the vocal fold system.

The method can include generating a "feature vector" that describes both the change from a defined condition (including zero change) and the repetitive condition of glottal tissue position and/or velocity during several speech time interval frames using time domain or frequency domain techniques. Three ways are: (1) record the digitized position or velocity of the desired organ position (including average position of the area opening) at each time frame generate the needed coefficients, (2) approximate the motion of the organ positions over several time frames, using recorded feature vector coefficients, with a mathematical function (e.g, such as a Taylor series or LPC series) and use the coefficients from the mathematical function in a "feature vector", (3) approximate the time varying, often repetitive, motions of the coefficients over the time frames by using Fourier (or similar) coefficients over the defined number of frames to define a "feature vector".

The methods as applied to the vocal folds can also be applied to the velum. The method can be used for determining whether or not nasalized speech has occurred in the defined time interval frame by determining degree of velum closure, and for associating feature vectors of the velum with models of the jaw position and/or velocities, and for generating a feature vector that describes velum contact with the back of the nasal passage during a given time interval frame.

The methods can also be applied to the jaw. A change in the jaw, and the open mouth volume that has occurred in the defined time interval frames, can be used to define the presence of single tube or two-tube phonemes such as "eh" or "ah". The presence of "plosive" consonants such as "b", "p", or other rapid consonant-vowel patterns, such as "ma", "me", "my", "bo", "ba", can be determined by measuring changes in jaw position or velocity during the speech time frames.

The methods can also be applied to the tongue, including a change in the average location or velocity of the tongue body, and parts of the tongue separately, including in particular, the tongue tip, the central body top surface, the back top surface, and the transverse curvature of the top surface. The method can be used to determine whether tongue contact with the roof of the mouth has occurred in the defined time interval frame.

The methods also apply to the lips and other speech organs, speech cavity air volumes, and/or air passages that participate in defining the speech qualities of a speaker during a defined single speech frame or for multiple speech frames. Examples of other organ conditions include diaphragm motion that defines lung volume and rate of air flow through the glottal opening. Examples of air passage measurements include the size of lungs, the pharynx, post glottal passages, nasal volume dimensions, sinus dimensions, mouth volume with relaxed, open, or closed jaw and tongue, and velic port dimension. The method can be used for determining a change in the average location of the interfaces or interface velocities of the organs or passages, or contact of the interfaces.

The method includes using one or more of the feature vectors or speech organ states for the purposes of determining, to a degree defined by the user, the speaker's entire vocal tract structure including air passage connections, the passage dimensions, the state of vocalization and the velocity state of the surrounding interfaces and walls, and the state of closure of the orifices such as the mouth, velum, glottis, and tongue-palate condition for a given speech time frame.

The method can be used to describe a partial or total speech tract feature vector for the speech time frame interval using elements from the EM information and the acoustic information. The method can also define a new feature vector in terms of well known acoustic model parameters that describe the conditions of the speaker's vocal excitation source and tract configuration during the time frame interval or intervals under consideration for the speech element. The method can also describe a single feature vector that describes a slowly changing sound unit condition (including zero change) of the excitation function and vocal tract conditions over a sequence of speech time frame intervals.

The method includes describing a feature vector by storing differences in each vector element from a previously defined known type of speaker, e.g. an averaged or individual American man, woman, or child; a foreign speaker with typical dialect in American English; or other language speakers of different genders or ages. This method includes displaying such information for purposes of speech correction, speech assistance, and speech education.

The method includes comparing a feature vector to stored information on a known human for the purpose of speaker identification, and for providing statistics of identification, including performing such comparisons automatically over several time frame units, isolated time frame units, or on sequences of units where stored information on the desired speaker's identity is available from a preformed library. The method includes training the algorithm before routine use by recording the speaker's idiosyncratic feature vector patterns for a defined word set, or by storing his non-normalized patterns of often used words or word patterns, and storing the trained information in an identification library.

The method includes using simultaneously recorded acoustic feature vector information with the EM information to define a single speech frame feature vector which describes the condition of the elementary speech unit with sufficient information, including redundancy and model constraints, that the phoneme (or other simple speech sound unit) of speech can be defined for the time period. The method can also identify with symbols, e.g. letters, pictogram codes, ASCII computer code, or telephony code, the sound unit under consideration with very high probability. The method can be used for determining the duration (i.e., the number of speech time frame intervals) of the observed sound unit, and using the duration information, plus the feature vector, to define a speech unit feature vector that accurately defines the sound condition over several sequential speech time frame intervals. The method includes defining the series of several feature vectors from several sequential time frames, as a composite feature vector. Such a composite feature vector may be described, for example, as one or more feature vectors attached end to end to describe the desired number of speech time frames.

The method includes automatically forming feature vectors for all elementary language sound pairs (i.e. diphones), triads (i.e. triphones), or other multi-units (i.e. quadphones and higher patterns) of a language, i.e. defining feature vectors applicable to the definition of two, three, or more sound units, and generating such sets of known language sounds for the purpose of defining, through training, libraries of known feature vectors for all elementary sound pairs, triads, or other multi-units.

The method can automatically form feature vectors for all word sounds of a language, i.e. define feature vectors applicable to the varying sound unit number in each word, and automatically generate such multi-unit sets of known word sounds for the purpose of defining, through training, libraries of known word feature vectors.

The method can also be used for automatically forming feature vectors for as many word combinations as desired in a given language, i.e. defining feature vectors applicable to the varying sound unit numbers (e.g. phoneme numbers) in each series of words included in the multi-word feature vectors. Such multi-word feature vectors, or vectors of individual sound unit feature vectors can be generated by limiting the number of phonemes to be stored at one time; or by using a predetermined running series of vectors wherein for each new word vector added, the oldest word feature vector is dropped; or by dynamic feedback based upon prosody constraints.

The method can automatically generate such multi-word vectors of known multi-word sounds for the purpose of defining, through training, libraries of known multi-word feature vectors, and automatically parse the multi-word vectors by phoneme units (including the silence phoneme) into units defined by prosody constraints, e.g. prosody constraints associated with punctuation marks or associated with pauses in thought by the speaker.

The method includes using vocal articulator feature vectors to identify the phoneme being spoken in the examined time frame by matching the pattern (i.e., template) of one or more speech organ conditions (e.g. multi-organ conditions) plus acoustic output against feature vectors stored in a previously defined library.

The method can include using Hidden Markov Model techniques (HMM) on the feature vectors to statistically identify the phoneme being spoken in the examined time frame or frames by operating on the feature vectors.

The method can also use joint probability to statistically identify the phoneme being spoken in the examined time frame. First, conventional (acoustic) speech recognition techniques are used to estimate the identity of the sound unit and its probability of identification. Next, the EM defined feature vectors are used alone (with no acoustic feature information included) to estimate separately the identity of the sound unit, and to assign an estimate of the probability for the non-acoustic case. Finally, the probabilities of each estimate are combined to obtain a more accurate identification of the word unit than either an all acoustic system, or all EM feature vector system could accomplish without the additional information.

The method can also use exclusive probability to statistically differentiate between acoustically similar phonemes being spoken in the examined time frame. First, a conventional (acoustic) speech recognition technique is used to estimate the identity of one or more sound units that have similar probabilities of being defined using conventional acoustic techniques alone (i.e, there remains ambiguity in a statistical sense). Next the EM defined feature vectors of each of the one or more acoustically identified phonemes (with no acoustic feature information included) are used to estimate separately the identity of the sound units, and to assign an estimate of the probability based on EM feature vectors for each ambiguous sound unit. Acoustic identification, not consistent with the EM identifications are excluded (i.e., rejected) from further consideration. Finally, the probabilities of each estimate, of the remaining acoustic units, are compared to obtain a more accurate identification of the word unit than either an all acoustic system, or all EM feature vector system could accomplish without the additional information from the other. In this manner, one can exclude all of the acoustically identified sound units except for one that meets the criteria defined by comparison with the library of stored feature vectors.

The multi-organ or phonetic pattern matching technique, the HMM technique, the joint probability technique, and the exclusive probability technique can all be used to identify the diphones, triphones, multiphones, words, or word sequences in the examined time frames.

The method includes use of neural network algorithms to associate a pattern measured with EM sensors of one or more speech organ motions in conjunction with acoustic speech with one or more speech sound units. This method uses the usual training methods for neural networks including normalization of input EM and acoustic signals and averaging of speakers (one or more), and associating the inputs though the neural network algorithms (e.g. using the back propagation algorithm, with two or more layers) with recognized sounds. Once trained, the networks provide a rapid convergence from the accurately defined input feature vectors to an identified output speech unit, because the information from the methods herein is so accurate.

The method also uses EM sensors in conjunction with an acoustic microphone, together with system components for the purposes of processing the sensor information, storing the information, conducting the recognition of the feature vectors, presenting the information in whatever stage of processing via visualization techniques or acoustic techniques, transmitting the information (with or without encryption, foreign language translation, speaker voice modification, bandwidth minimization, or other processes), and interfaced with keyboards or handheld control units used for the purposes of aiding in voice activated controls, dictation, transcription, language translation or teaching, speaker modification, prosthesis feedback or activation of special technology systems.

The method also includes synchronizing acoustic speech with lip motion or other visual speech organ motions such as jaw motions with visual images. An example is lip synchronization of speech or music for the movie or video industry.

Changes and modifications in the specifically described embodiments can be carried out without departing from the scope of the invention which is intended to be limited only by the scope of the appended claims.

I claim:

1. A method of speech characterization of speech by a speaker, comprising:
   directing electromagnetic (EM) radiation toward speech organs of the speaker;
   detecting electromagnetic (EM) radiation scattered from the speech organs to measure speech organ conditions to obtain EM speech information;
   detecting acoustic speech output from the speaker to obtain acoustic speech information;
   combining the EM speech information with the acoustic speech information using a speech characterization algorithm.

2. The method of claim 1 wherein the speech is selected from normal sounded speech, whispered speech, and non-sounded speech.

3. The method of claim 1 wherein acoustic speech output of the speaker is detected using at least one acoustic microphone.

4. The method of claim 3 further comprising measuring acoustic pressure or sound intensity over a plurality of sampling times to obtain amplitude vs. time, frequency, zero crossing times, energy per time interval, and LPC or cepstral coefficients of acoustic speech.

5. The method of claim 1 wherein acoustic speech output of the speaker is detected using at least one EM wave microphone to detect acoustic vibrations.

6. The method of claim 1 wherein EM radiation is directed to and detected from the speech organs using an EM wave transmitting and receiving system.

7. The method of claim 6 wherein the EM wave generating, transmitting and detecting system is an RF, microwave, millimeter wave, infrared, or visible wave EM sensor.

8. The method of claim 7 wherein the EM sensor is operated in a time of flight, non-coherent mode.

9. The method of claim 8 wherein the EM sensor is range-gated.

10. The method of claim 7 wherein the EM sensor is operated in a coherent mode.

11. The method of claim 10 wherein the EM sensor is operated in a homodyne, heterodyne or other interferometric coherent detection mode.

12. The method of claim 7 where the EM sensor is operated in a field disturbance mode, with or without a range gate, with time filtered output.

13. The method of claim 1 further comprising controlling the time of generation, transmission and detection of the EM radiation and of substantially simultaneous reception of the acoustic speech output.

14. The method of claim 1 further comprising creating feature vectors describing features of the acoustic speech output and EM sensor measured speech organ conditions during a defined time frame of speech.

15. The method of claim 14 further comprising storing, in the feature vector, the start time, duration time, and end time of the defined time frame of each feature vector.

16. The method of claim 14 further comprising associating information contained in the feature vector with information from other instruments or devices for the purposes of synchronization of timing.

17. The method of claim 14 further comprising storing the feature vectors in an electronic library.

18. The method of claim 17 further comprising performing time alignment of the feature vector of a particular speaker, and comparing the time aligned feature vector of the particular speaker with feature vectors in the library.

19. The method of claim 14 further comprising producing a feature vector for one or more speakers, averaging the feature vectors of the one or more speakers, and storing the averaged feature vector in a library.

20. The method of claim 14 further comprising normalizing and quantizing the speaker's feature vectors to those of a reference speaker or group of speakers.

21. The method of claim 14 further comprising producing feature vectors for at least one of position and velocity of at least one of the velum, jaw, tongue, glottal tissue, and lips.

22. The method of claim 14 further comprising forming a single or multiple speech frame feature vector which defines a syllable like unit, a phoneme, a PLU, a diphone, a triphone, an acoustic unit, a word, or a word sequence.

23. The method of claim 14 further comprising applying a statistical technique or pattern matching technique to the feature vector to identify a syllable like unit, a phoneme, a PLU, a diphone, a triphone, an acoustic unit, a word, or a word sequence.

24. The method of claim 23 wherein the statistical technique is a Hidden Markov Model technique or a neural network technique.

25. The method of claim 23 wherein the pattern matching technique is a phonetic-template matching technique.

26. The method of claim 23 wherein the algorithm uses a joining or excluding method of identification by comparing feature vectors identified using conventional acoustic techniques to those identified using non-acoustic techniques to obtain a higher overall probability of identification.

27. The method of claim 14 further comprising forming the feature vector by first forming separate acoustic and EM feature vectors, and then combining the separate acoustic and EM feature vectors.

28. The method of claim 14 further comprising identifying sound changes and EM signal changes to define a new feature vector defined by changes from a referenced feature vector.

29. The method of claim 14 further comprising identifying acoustic changes and EM signal changes, compared to those of the last time frame, to define a new speech time frame.

30. The method of claim 14 further comprising automatically forming the feature vector.

31. The method of claim 14 further comprising creating a feature vector that describes a defined condition and change from the defined condition of position and/or velocity of at least one speech organ during a plurality of speech time frames.

32. The method of claim 14 further comprising forming a feature vector for velocity and acceleration over a plurality of time frames.

33. The method of claim 14 further comprising identifying a speaker from patterns of feature vectors formed by that speaker, over a sequential series of speech time frames.

34. The method of claim 1 further comprising obtaining organ velocity or acceleration information from the detected EM radiation.

35. The method of claim 1 further comprising measuring other speech information than the EM speech information and acoustic speech information and combining the other speech information with the EM speech information and acoustic speech information.

36. The method of claim 1 further comprising determining a set of mechanical parameters of the vocal system from the EM speech information and acoustic speech information for vocal system modeling.

37. The method of claim 1 wherein the algorithm determines the onset of speech, end of speech, speech period, pauses, speech rate, and extraneous noise.

38. The method of claim 1 wherein the algorithm determines the presence of voiced or unvoiced speech.

39. The method of claim 1 further comprising measuring organ contact as one organ touches another and strongly changes the EM wave reflecting condition because of changing resonator or boundary condition effects.

40. The method of claim 1 further comprising generating and transmitting a series of known wavelengths to detect organ interface spacings using coherent reflections and transmissions from the tissue and tissue interfaces.

41. Apparatus for speech characterization of speech by a speaker, comprising:
- at least one electromagnetic (EM) wave generating, transmitting and detecting unit for directing EM waves toward and detecting EM waves scattered from speech organs of the speaker to obtain EM speech information;
- at least one microphone for detecting acoustic speech output from the speaker to obtain acoustic speech information;
- means for combining the EM speech information with the acoustic speech information using a speech characterization algorithm.

42. The apparatus of claim 41 wherein each EM wave generating, transmitting and receiving unit is a RF, microwave, millimeter wave, infrared, or visible wave radar.

43. The apparatus of claim 41 wherein each microphone is an acoustic microphone or an EM microphone.

44. The apparatus of claim 41 further comprising a structure for mounting the at least one EM wave generating, transmitting and detecting unit and at least one microphone such that they can detect the conditions of the speech organs of the speaker.

45. The apparatus of claim 41 further comprising means for controlling the time of generation, transmission, and reception of the EM waves and of substantially simultaneous reception of the acoustic speech output.

46. The apparatus of claim 42 wherein the EM unit is a time of flight, non-coherent radar, or a field disturbance sensor, with or without a range gate, with time filtered output, or a coherent radar.

47. The apparatus of claim 42 wherein the EM unit is a range-gated radar.

48. The apparatus of claim 42 wherein the EM unit is a homodyne, heterodyne or other interferometric coherent detection EM sensor.

* * * * *